US009932575B2

(12) United States Patent
McPherson et al.

(10) Patent No.: US 9,932,575 B2
(45) Date of Patent: Apr. 3, 2018

(54) SCAFFOLD PROTEINS DERIVED FROM PLANT CYSTATINS

(71) Applicant: University of Leeds, Leeds (GB)

(72) Inventors: Michael McPherson, Leeds (GB);
Darren Tomlinson, Leeds (GB)

(73) Assignee: University of Leeds, Leeds (GB)

(*) Notice: Subject to any disclaimer, the term of this patent is extended or adjusted under 35 U.S.C. 154(b) by 0 days.

(21) Appl. No.: 14/768,032

(22) PCT Filed: Feb. 14, 2014

(86) PCT No.: PCT/GB2014/050435
§ 371 (c)(1),
(2) Date: Aug. 14, 2015

(87) PCT Pub. No.: WO2014/125290
PCT Pub. Date: Aug. 21, 2014

(65) Prior Publication Data
US 2016/0032278 A1 Feb. 4, 2016

(30) Foreign Application Priority Data
Feb. 14, 2013 (GB) .................................. 1302597.8

(51) Int. Cl.
| C07K 14/415 | (2006.01) |
| A61K 38/16 | (2006.01) |
| C12N 15/10 | (2006.01) |
| G01N 33/68 | (2006.01) |
| A61K 38/00 | (2006.01) |

(52) U.S. Cl.
CPC ........ *C12N 15/1037* (2013.01); *A61K 38/168* (2013.01); *C07K 14/415* (2013.01); *G01N 33/68* (2013.01); *A61K 38/00* (2013.01); *G01N 2333/415* (2013.01); *G01N 2500/04* (2013.01)

(58) Field of Classification Search
CPC .... A61K 38/168; A61K 38/00; C07K 14/415; C12N 15/1037; G01N 33/68; G01N 2500/04; G01N 2333/415
See application file for complete search history.

(56) References Cited

U.S. PATENT DOCUMENTS

| 5,168,062 A | 12/1992 | Stinski | |
| 2007/0162998 A1* | 7/2007 | Yeh ..................... | C12N 15/8282 800/279 |
| 2010/0095408 A1* | 4/2010 | Heath ..................... | A01N 65/00 800/301 |

FOREIGN PATENT DOCUMENTS

| CN | 101495653 | 7/2009 |
| WO | WO 00/67796 A1 | 11/2000 |
| WO | WO 2006/131749 A2 | 12/2006 |
| WO | WO 2007/095300 A2 | 8/2007 |
| WO | WO 2009/136182 A1 | 11/2009 |
| WO | WO 2010/015024 A1 | 2/2010 |
| WO | WO 2011/137319 A2 | 11/2011 |

OTHER PUBLICATIONS

C0STW6, from http://www.uniprot.org/uniprot/C0STW6, pp. 1-5, last modified on May 26, 2009, accessed Jan. 15, 2016.*
pcDNA3.1 MycHis map, from Invitrogen, p. 1, accessed Jul. 26, 2016.*
Neuteboom et al, An Extended AE-Rich N-Terminal Trunk in Secreted Pineapple Cystatin Enhances Inhibition of Fruit Bromelain and Is Posttranslationally Removed during Ripening, Plant Physiol., 2009, 151, pp. 515-527.*
Water, from http://www.biology-online.org/dictionary/Water, pp. 1-3, accessed Apr. 24, 2014.*
Glutamate dehydrogenase-Pyrococcus furiosus, from https://www.ncbi.nlm.nih.gov/protein/WP_011012748.1, p. 1, accessed Dec. 1, 2016.*
Klump et al, Glutamate Dehydrogenase from the Hyperthermophile Pyrococcus furiosus, The Journal of Biological Chemistry, 1992, 267, pp. 22681-22685.*
Catanzariti et al, An efficient system for high-level expression and easy purification of authentic recombinant proteins, Protein Science, 2004, 13, pp. 1331-1339.*
Terpe, Overview of tag protein fusions: from molecular and biochemical fundamentals to commercial systems, Appl Microbiol Biotechnol, 2003, 60, pp. 523-533.*
Abe et al. "The $NH_2$-terminal 21 Amino Acid Residues Are Not Essential for the Papain-inhibitory Activity of Oryzacystatin, a Member of the Cystatin Superfamily" *The Journal of Biological Chemistry* 263(16):7655-7659 (1988).
Altschul et al. "Gapped BLAST and PSI-BLAST: a new generation of protein database search programs" *Nucleic Acids Research* 25(17):3389-3402 (1997).
Anderson et al. "Selective Photothermolysis: Precise Microsurgery by Selective Absorption of Pulsed Radiation" *Science* 220(4596):524-527 (1983).
Ben-Bassat et al. "Processing of the Initiation Methionine from Proteins: Properties of the *Escherichia coli* Methionine Aminopeptidase and Its Gene Structure" *Journal of Bacteriology* 169(2):751-757 (1987).
Brinster et al. "Regulation of metallothionein-thymidine kinase fusion plasmids injected into mouse eggs" *Nature* 296:39-42 (1982).

(Continued)

*Primary Examiner* — Julie Ha
*Assistant Examiner* — Li N Komatsu
(74) *Attorney, Agent, or Firm* — Myers Bigel, P.A.

(57) ABSTRACT

The present invention relates to scaffold proteins derived from plant cystatins and to nucleic acids encoding them. The scaffolds are highly stable and have the ability to display peptides. The scaffolds are particularly well suited for constructing libraries, e.g., in phage display or related systems. The invention also relates to various uses of the scaffolds, including in therapy, diagnosis, environmental and security monitoring, synthetic biology and research, and to cells and cell cultures expressing the scaffold proteins.

22 Claims, 21 Drawing Sheets

(56) References Cited

OTHER PUBLICATIONS

GenBank Accession No. C95263 "Citrus unshiu Miyagawa-wase maturation stage Citrus unshiu cDNA clone pcMAIM0910-89 5-, mRNA sequence" *NCBI* (1 page) (Mar. 9, 2007).
GenBank Accession No. U54702 "*Oryza sativa* oryzacystatin mRNA, complete cds" *NCBI* (2 pages) (Aug. 11, 1997).
Goldstein et al. "Prokaryotic promoters in biotechnology" *Biotechnology Annual Review* 1:105-128 (1995) (Abstract Only).
Gorman et al. "The Rous sarcoma virus long terminal repeat is a strong promoter when introduced into a variety of eukaryotic cells by DNA-mediated transfection" *Proceedings of the National Academy of Sciences USA* 79:6777-6781 (1982).
Henikoff et al. "Amino acid substitution matrices from protein blocks" *Proceedings of the National Academy of Sciences USA* 89:10915-10919 (1992).
Hochuli et al. "Genetic Approach to Facilitate Purification of Recombinant Proteins with a Novel Metal Chelate Adsorbent" *Bio/Technology* 6:1321-1325 (1988).
O'Regan et al. "Cloning and nucleotide sequence of the phosphoenolpyruvate carboxylase-coding gene of Corynebacterium glutamicum ATCC13032" *Gene* 77(2):237-251 (1989) (Abstract Only).
Mettenleiter et al. "A glycoprotein gX-beta-galactosidase fusion gene as insertional marker for rapid identification of pseudorabies virus mutants" *Journal of Virological Methods* 30(1):55-65 (1990) (Abstract Only).
Needleman et al. "A General Method Applicable to the Search for Similarities in the Amino Acid Sequence of Two Proteins" *Journal of Molecular Biology* 48:443-453 (1970).
Sahab et al. "Quantitative Measurement of Human Papillomavirus Type 16 E5 Oncoprotein Levels in Epithelial Cell Lines by Mass Spectrometry" *Journal of Virology* 86(17):9465-9473 (2012).
Sahin-Toth et al. "Cysteine scanning mutagenesis of the N-terminal 32 amino acid residues in the lactose permease of *Escherichia coli*" *Protein Science* 3:240-247 (1994).
Skerra, Arne "Engineered protein scaffolds for molecular recognition" *Journal of Molecular Recognition* 13:167-187 (2000).
Voellmy et al. "Isolation and functional analysis of a human 70,000-dalton heat shock protein gene segment" *Proceedings of the National Academy of Sciences USA* 82:4949-4953 (1985).
Benchabane et al. "Plant cystatins" *Biochimie* 92:1657-1666 (2010).
International Search Report and the Written Opinion of the International Searching Authority corresponding to International Patent Application No. PCT/GB2014/050435 (16 pages) (dated May 9, 2014).
Kordis et al. "Phylogenomic analysis of the cystatin superfamily in eukaryotes and prokaryotes" *BMC Evolutionary Biology* 9(266):1-11 (2009).
Margis et al. "Structural and Phylogenetic Relationships among Plant and Animal Cystatins" *Archives of Biochemistry and Biophysics* 359(1):24-30 (1998).
Tajima et al. "Biochemical and molecular characterization of senescence-related cysteine protease-cystatin complex from spinach leaf" *Physiologia Plantarum* 141:97-116 (2011).
Willats, William G.T. "Phage display: practicalities and prospects" *Plant Molecular Biology* 50:837-854 (2002).
Woodman et al. "Design and Validation of a Neutral Protein Scaffold for the Presentation of Peptide Aptamers" *Journal of Molecular Biology* 362:1118-1133 (2005).
Astwood et al. "Stability of food allergens to digestion in vitro" *Nature Biotechnology* 14:1269-1273 (1996).
Atkinson et al. "Prima Facie Evidence That a Phytocystatin for Transgenic Plant Resistance to Nematodes Is Not a Toxic Risk in the Human Diet" *The Journal of Nutrition* 134:431-434 (2004).
Bendtsen et al. "Improved Prediction of Signal Peptides: SignalP 3.0" *Journal of Molecular Biology* 340:783-795 (2004).

Binz et al. "Designing Repeat Proteins: Well-expressed, Soluble and Stable Proteins from Combinatorial Libraries of Consensus Ankyrin Repeat Proteins" *Journal of Molecular Biology* 332(2):489-503 (2003).
Bode et al. "The 2.0 Å X-ray crystal structure of chicken egg white cystatin and its possible mode of interaction with cysteine proteinases" *The EMBO Journal* 7(8):2593-2599 (1988).
Carter, Paul J. "Introduction to current and future protein therapeutics: A protein engineering perspective" *Experimental Cell Research* 317:1261-1269 (2011).
Dai et al. "The creation of a novel fluorescent protein by guided consensus engineering" *Protein Engineering, Design & Selection* 20(2):69-79 (2007).
De Boer et al. "The tac promoter: A functional hybrid derived from the trp and lac promoters" *Proceedings of the National Academy of Sciences USA* 80:21-25 (1983).
Filippova et al. "L-Pyroglutamyl-L-phenylalanyl-L-leucine-p-nitroanilide—A Chromogenic Substrate for Thiol Proteinase Assay" *Analytical Biochemistry* 143:293-297 (1984).
Fitzgerald, Kevin "In vitro display technologies—new tools for drug discovery" *Drug Discovery Today* 5(6):253-258 (2000).
Forrer et al. "Consensus Design of Repeat Proteins" *ChemBioChem* 5:183-189 (2004).
Gebauer et al. "Engineered protein scaffolds as next-generation antibody therapeutics" *Current Opinion in Chemical Biology* 13:245-255 (2009).
Grebien et al. "Targeting the SH2-Kinase Interface in Bcr-Abl Inhibits Leukemogenesis" *Cell* 147:306-319 (2011).
Ho et al. "Mammalian Cell Display for Antibody Engineering" *Methods in Molecular Biology* 525:1-15 (2009).
Hoffmann et al. "Structure-function studies of an engineered scaffold protein derived from stefin A. I: Development of the SQM variant" *Protein Engineering, Design & Selection* 23(5):403-413 (2010).
Hoogenboom et al. "Multi-subunit proteins on the surface of filamentous phage: methodologies for displaying antibody (Fab) heavy and light chains" *Nucleic Acids Research* 19(15):4133-4137 (1991).
Horton et al. "Gene Splicing by Overlap Extension: Tailor-Made Genes Using the Polymerase Chain Reaction" *BioTechniques* 8(5):528-535 (1990).
Hutchison et al. "Mutagenesis at a Specific Position in a DNA Sequence" *The Journal of Biological Chemistry* 253(18):6561-6560 (1978).
Jacobs et al. "Design of novel FN3 domains with high stability by a consensus sequence approach" *Protein Engineering, Design & Selection* 25(3):107-117 (2012).
Jaeckel et al. "Consensus Protein Design Without Phylogenetic Bias" *Journal of Molecular Biology* 399(4):541-546 (2010).
Karatan et al. "Molecular Recognition Properties of FN3 Monobodies that Bind the Src SH3 Domain" *Chemistry & Biology* 11:835-844 (2004).
Kayushin et al. "A convenient approach to the synthesis of trinucleoide phosphoramidites—synthons for the generation of oligonucleotide/peptide libraries" *Nucleic Acids Research* 24(19):3748-3755 (1996).
Knappik et al. "Fully Synthetic Human Combinatorial Antibody Libraries (HuCAL) Based on Modular Consensus Frameworks and CDRs Randomized with Trinucleotides" *Journal of Molecular Biology* 296:57-86 (2000).
Kohler et al. "Continuous cultures of fused cells secreting antibody of predefined specificity" *Nature* 256:495-497 (1975).
Koide et al. "The Fibronectin Type III Domain as a Scaffold for Novel Binding Proteins" *Journal of Molecular Biology* 284:1141-1151 (1998).
Koide et al. "High-affinity single-domain binding proteins with a binary-code interface" *Proceedings of the National Academy of Sciences* 104(16):6632-6637 (2007).
Koiwa et al. "Phage display selection of hairpin loop soyacystatin variants that mediate high affinity inhibition of a cysteine proteinase" *The Plant Journal* 27(5):383-391 (2001).

(56) References Cited

OTHER PUBLICATIONS

Komor et al. "Highly thermostable fungal cellobiohydrolase I (Cel7A) engineered using predictive methods" *Protein Engineering, Design & Selection* 25(12):827-833 (2012).
Krumpe et al. "Trinucleotide cassettes increase diversity of T7 phage-displayed peptide library" *BMC Biotechnology* 7(65):1-8 (2007).
Lee et al. "Design of a binding scaffold based on variable lymphocyte receptors of jawless vertebrates by module engineering" *Proceedings of the National Academy of Sciences* 109(9):3299-3304 (2012).
Lehmann et al. "Exchanging the active site between phytases for altering the functional properties of the enzyme" *Protein Science* 9:1866-1872 (2000).
Lehmann et al. "Engineering proteins for thermostability: the use of sequence alignments versus rational design and directed evolution" *Current Opinion in Biotechnology* 12:371-375 (2001).
Lehmann et al. "The consensus concept for thermostability engineering of proteins: further proof of concept" *Protein Engineering* 15(5):403-411 (2002).
Lilley et al. "Preferential expression of a plant cystatin at nematode feeding sites confers resistance to *Meloidogyne incognita* and *Globodera pallida*" *Plant Biotechnology Journal* 2:3-12 (2004).
Lofblom, John "Bacterial display in combinatorial protein engineering" *Biotechnology Journal* 6:1-15 (2011).
Lord et al. "Cinema-MX: a modular multiple alignment editor" *Bioinformatics* 18(10):1402-1403 (2002).
Main et al. "Design of Stable α-Helical Arrays from an Idealized TPR Motif" *Structure* 11:497-508 (2003).
Main et al. "The folding and design of repeat proteins: reaching a consensus" *Current Opinion in Structural Biology* 13:482-489 (2003).
Main et al. "A recurring theme in protein engineering: the design, stability and folding of repeat proteins" *Current Opinion in Structural Biology* 15:464-471 (2005).
Makela et al. "The Baculovirus Display Technology—An Evolving Instrument for Molecular Screening and Drug Delivery" *Combinatorial Chemistry & High Throughput Screening* 11:86-98 (2008).
McPherson et al. "Engineering Plant Nematode Resistance by Anti-Feedants" *Cellular and Molecular Basis for Plant-Nematode Interactions* pp. 237-249 (1997).
Melo et al. "Use of phage display to select novel cystatins specific for *Acanthoscelides obtectus* cysteine proteinases" *Biochimica et Biophysica Acta* 1651:146-152 (2003).
Mosavi et al. "Consensus-derived structural determinants of the ankyrin repeat motif" *Proceedings of the National Academy of Sciences* 99(25):16029-16034 (2002).
Mosavi et al. "The ankyrin repeat as molecular architecture for protein recognition" *Protein Science* 13:1435-1448 (2004).
Mullis et al. "Specific Enzymatic Amplification of DNA In Vitro: The Polymerase Chain Reaction" *Cold Spring Harbor Symposia on Quantitative Biology* 51:263-273 (1986).
Nagata et al. "Three-Dimensional Solution Structure of Oryzacystatin-I, a Cysteine Proteinase Inhibitor of the Rice, *Oryza sativa* L. japonica" *Biochemistry* 39:14753-14760 (2000).
Nixon et al. "Engineered protein inhibitors of proteases" *Current Opinion in Drug Discovery & Development* 9(2):261-268 (2006).
Nord et al. "A combinatorial library of an α-helical bacterial receptor domain" *Protein Engineering* 8(6):601-608 (1995).
Odegrip et al. "CIS display: In vitro selection of peptides from libraries of protein—DNA complexes" *Proceedings of the National Academy of Sciences* 101(9):2806-2810 (2004).
Parizek et al. "Designed Ankyrin Repeat Proteins (DARPins) as Novel Isoform-Specific Intracellular Inhibitors of c-Jun N-Terminal Kinases" *ACS Chemical Biology* 7:1356-1366 (2012).
Parmeggiani et al. "Designed Armadillo Repeat Proteins as General Peptide-Binding Scaffolds: Consensus Design and Computational Optimization of the Hydrophobic Core" *Journal of Molecular Biology* 376:1282-1304 (2008).
Parry-Smith et al. "CINEMA—a novel Colour INteractive Editor for Multiple Alignments" *Gene* 221:GC57-63 (1998).
Polizzi et al. "Structure-guided consensus approach to create a more thermostable penicillin G acylase" *Biotechnology Journal* 1:531-536 (2006).
Reichert, Janice M. "Antibodies to watch in 2010" *mAbs* 2(1):84-100 (2010).
Saiki et al. "Enzymatic Amplification of β-Globin Genomic Sequences and Restriction Site Analysis for Diagnosis of Sickle Cell Anemia" *Science* 230:1350-1354 (1985).
Schlehuber et al. "Anticalins as an alternative to antibody technology" *Expert Opinion on Biological Therapy* 5(11):1453-1462 (2005).
Skerra, Arne "Alternative non-antibody scaffolds for molecular recognition" *Opinion in Biotechnology* 18:295-304 (2007).
Smith, George P. "Filamentous Fusion Phage: Novel Expression Vectors That Display Cloned Antigens on the Virion Surface" *Science* 228:1315-1317 (1985).
Song et al. "Inhibition of cysteine proteinases by *Carica papaya* cystatin produced in *Escherichia coli*" *Gene* 162:221-224 (1995).
Song et al. "Identification of a SUMO-binding motif that recognizes SUMO-modified proteins" *Proceedings of the National Academy of Sciences* 101(40):14373-14378 (2004).
Song et al. "Small Ubiquitin-like Modifier (SUMO) Recognition of a SUMO Binding Motif" *The Journal of Biological Chemistry* 280(48):40122-40129 (2005).
Stadler et al. "Structure—function studies of an engineered scaffold protein derived from Stefin A. II: Development and applications of the SQT variant" *Protein Engineering, Design & Selection* 24(9):751-763 (2011).
Steipe et al. "Sequence Statistics Reliably Predict Stabilizing Mutations in a Protein Domain" *Journal of Molecular Biology* 240:188-192 (1994).
Steipe, Boris "Consensus-Based Engineering of Protein Stability: From Intrabodies to Thermostable Enzymes" *Protein Engineering* 388:176-186 (2004).
Stubbs et al. "The refined 2.4 Å X-ray crystal structure of recombinant human stefin B in complex with the cysteine proteinase papain: a novel type of proteinase inhibitor interaction" *The EMBO Journal* 9(6):1939-1947 (1990).
Studier et al. "Use of Bacteriophage T7 RNA Polymerase to Direct Selective High-level Expression of Cloned Genes" *Journal of Molecular Biology* 189:113-130 (1986).
Theurillat et al. "Designed ankyrin repeat proteins: a novel tool for testing epidermal growth factor receptor 2 expression in breast cancer" *Modern Pathology* 23:1289-1297 (2010).
Traxlmayr et al. "Directed evolution of proteins for increased stability and expression using yeast display" *Archives of Biochemistry and Biophysics* 526:174-180 (2012).
Urwin et al. "Engineered oryzacystatin-I expressed in transgenic hairy roots confers resistance to *Globodera pallida*" *The Plant Journal* 8(1):121-131 (1995).
Urwin et al. "Resistance to both cyst and root-knot nematodes conferred by transgenic *Arabidopsis* expressing a modified plant cystatin" *The Plant Journal* 12(2):455-461 (1997).
Urwin et al. "Enhanced transgenic plant resistance to nematodes by dual proteinase inhibitor constructs" *Planta* 204:472-479 (1998).
Urwin et al. "Transgenic resistance to the nematode *Rotylenchulus reinformis* conferred by *Arabidopsis thaliana* plants expressing proteinase inhibitors" *Molecular Breeding* 6:257-264 (2000).
Urwin et al. "Effective transgenic resistance to *Globodera pallida* in potato field trials" *Molecular Breeding* 8:95-101 (2001).
Urwin et al. "Expression of a plant cystatin confers partial resistance to *Globodera*, full resistance is achieved by pyramiding a cystatin with natural resistance" *Molecular Breeding* 12:263-269 (2003).
Virnekas et al. "Trinucleotide phosphoramidites: ideal reagents for the synthesis of mixed oligonucleotides for random mutagenesis" *Nucleic Acids Research* 22(25):5600-5607 (1994).
Von Behring et al. "The mechanism of immunity in animals to diphtheria and tetanus" *Deutsche Medizinische Wochenschrift* 16:1113-1114 (1890).

(56) References Cited

OTHER PUBLICATIONS

Wojcik et al. "A potent and highly specific FN3 monobody inhibitor of the AbI SH2 domain" *Nature Structural & Molecular Biology* 17(4):519-527 (2010).

Wurch et al. "Novel protein scaffolds as emerging therapeutic proteins: from discovery to clinical proof-of-concept" *Trends in Biotechnology* 30(11):575-582 (2012).

Chinese Search Report & English Translation thereof corresponding to Chinese Patent Application No. 2014800220705 (4 pages) (dated Sep. 30, 2016).

* cited by examiner

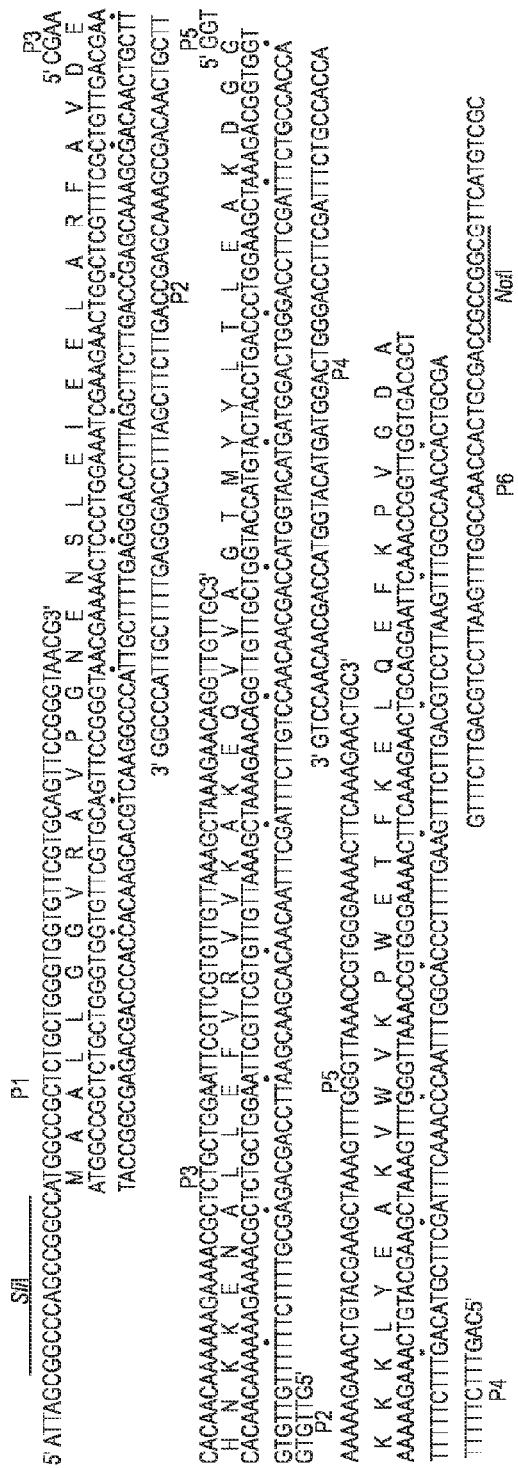
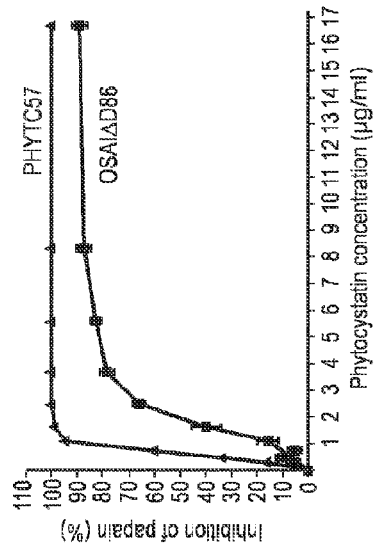
Fig. 1A
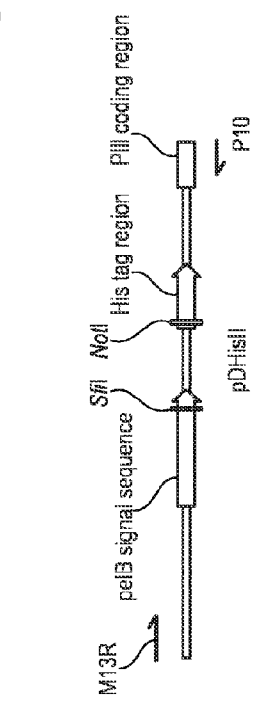
Fig. 1B
Fig. 2

A

OSAIDD86 MSSDGGPVLG GVEPV.GNEN DLHLVDLARF AVTEHNKKAN SLLEFEKLVS
PHYTC57  ....MAALLG GVRAVPGNEN SLEIEELARF AVDEHNKKEN ALLEFVRVVK

OSAIDD86 VKQQVVAGTL YYFTIEVKEG DAKKLYEAKV WEKPWM.FKE LQEFKPVDASANA
PHYTC57  AKEQVVAGTM YYLTLEAKDG GKKKLYEAKV VVKPWETFKE LQEFKPVGDA

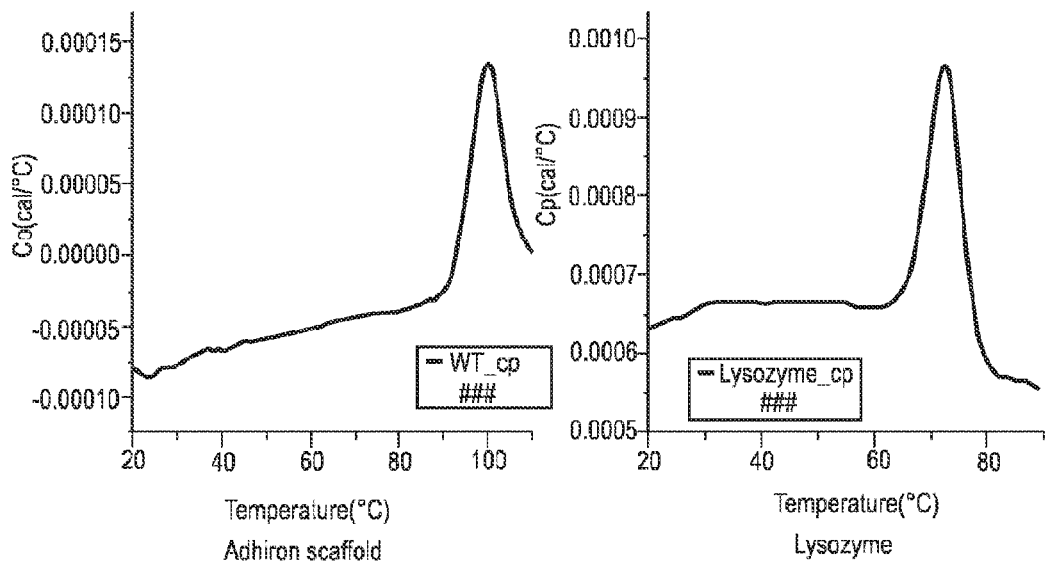
Fig. 8a
Fig. 8b
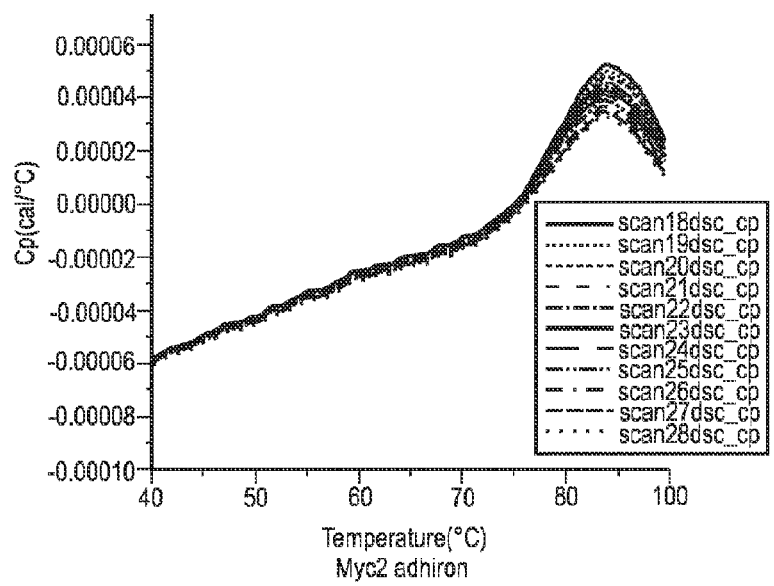
Fig. 8c

SEQUENCE LISTING

```
<160> NUMBER OF SEQ ID NOS: 241

<210> SEQ ID NO 1
<211> LENGTH: 81
<212> TYPE: PRT
<213> ORGANISM: Artificial Sequence
<220> FEATURE:
<223> OTHER INFORMATION: Synthetic Scaffold

<400> SEQUENCE: 1

Asn Ser Leu Glu Ile Glu Glu Leu Ala Arg Phe Ala Val Asp Glu His
1               5                   10                  15

Asn Lys Lys Glu Asn Ala Leu Leu Glu Phe Val Arg Val Val Lys Ala
            20                  25                  30

Lys Glu Gln Val Val Ala Gly Thr Met Tyr Tyr Leu Thr Leu Glu Ala
        35                  40                  45

Lys Asp Gly Gly Lys Lys Lys Leu Tyr Glu Ala Lys Val Trp Val Lys
    50                  55                  60
```

```
Pro Trp Glu Asn Phe Lys Glu Leu Gln Glu Phe Lys Pro Val Gly Asp
 65                  70                  75                  80

Ala

<210> SEQ ID NO 2
<211> LENGTH: 84
<212> TYPE: PRT
<213> ORGANISM: Artificial Sequence
<220> FEATURE:
<223> OTHER INFORMATION: Synthetic Scaffold

<400> SEQUENCE: 2

Gly Asn Glu Asn Ser Leu Glu Ile Glu Glu Leu Ala Arg Phe Ala Val
  1               5                  10                  15

Asp Glu His Asn Lys Lys Glu Asn Ala Leu Leu Glu Phe Val Arg Val
                 20                  25                  30

Val Lys Ala Lys Glu Gln Val Val Ala Gly Thr Met Tyr Tyr Leu Thr
             35                  40                  45

Leu Glu Ala Lys Asp Gly Gly Lys Lys Lys Leu Tyr Glu Ala Lys Val
         50                  55                  60

Trp Val Lys Pro Trp Glu Asn Phe Lys Glu Leu Gln Glu Phe Lys Pro
 65                  70                  75                  80

Val Gly Asp Ala

<210> SEQ ID NO 3
<211> LENGTH: 92
<212> TYPE: PRT
<213> ORGANISM: Artificial Sequence
<220> FEATURE:
<223> OTHER INFORMATION: Synthetic Scaffold

<400> SEQUENCE: 3

Ala Thr Gly Val Arg Ala Val Pro Gly Asn Glu Asn Ser Leu Glu Ile
  1               5                  10                  15

Glu Glu Leu Ala Arg Phe Ala Val Asp Glu His Asn Lys Lys Glu Asn
                 20                  25                  30

Ala Leu Leu Glu Phe Val Arg Val Val Lys Ala Lys Glu Gln Val Val
             35                  40                  45

Ala Gly Thr Met Tyr Tyr Leu Thr Leu Glu Ala Lys Asp Gly Gly Lys
         50                  55                  60

Lys Lys Leu Tyr Glu Ala Lys Val Trp Val Lys Pro Trp Glu Asn Phe
 65                  70                  75                  80

Lys Glu Leu Gln Glu Phe Lys Pro Val Gly Asp Ala
                 85                  90

<210> SEQ ID NO 4
<211> LENGTH: 74
<212> TYPE: PRT
<213> ORGANISM: Artificial Sequence
<220> FEATURE:
<223> OTHER INFORMATION: Synthetic Scaffold
<220> FEATURE:
<221> NAME/KEY: NON_CONS
<222> LOCATION: (35)..(36)
<223> OTHER INFORMATION: Variable region between these residues
<220> FEATURE:
<221> NAME/KEY: NON_CONS
<222> LOCATION: (60)..(61)
<223> OTHER INFORMATION: Variable region between these residues

<400> SEQUENCE: 4

Asn Ser Leu Glu Ile Glu Glu Leu Ala Arg Phe Ala Val Asp Glu His
```

```
                1               5                   10                  15
Asn Lys Lys Glu Asn Ala Leu Leu Glu Phe Val Arg Val Val Lys Ala
            20                  25                  30

Lys Glu Gln Thr Met Tyr Tyr Leu Thr Leu Glu Ala Lys Asp Gly Gly
        35                  40                  45

Lys Lys Lys Leu Tyr Glu Ala Lys Val Trp Val Lys Asn Phe Lys Glu
    50                  55                  60

Leu Gln Glu Phe Lys Pro Val Gly Asp Ala
65                  70

<210> SEQ ID NO 5
<211> LENGTH: 74
<212> TYPE: PRT
<213> ORGANISM: Artificial Sequence
<220> FEATURE:
<223> OTHER INFORMATION: Synthetic scaffold
<220> FEATURE:
<221> NAME/KEY: NON_CONS
<222> LOCATION: (35)..(36)
<223> OTHER INFORMATION: Variable region between these residues
<220> FEATURE:
<221> NAME/KEY: NON_CONS
<222> LOCATION: (60)..(61)
<223> OTHER INFORMATION: Variable region between these residues

<400> SEQUENCE: 5

Asn Ser Leu Glu Ile Glu Glu Leu Ala Arg Phe Ala Val Asp Glu His
1               5                   10                  15

Asn Lys Lys Glu Asn Ala Leu Leu Glu Phe Val Arg Val Val Lys Ala
            20                  25                  30

Lys Glu Gln Thr Met Tyr Tyr Leu Thr Leu Glu Ala Lys Asp Gly Gly
        35                  40                  45

Lys Lys Lys Leu Tyr Glu Ala Lys Val Trp Val Lys Asn Phe Lys Glu
    50                  55                  60

Leu Gln Glu Phe Lys Pro Val Gly Asp Ala
65                  70

<210> SEQ ID NO 6
<211> LENGTH: 92
<212> TYPE: PRT
<213> ORGANISM: Artificial Sequence
<220> FEATURE:
<223> OTHER INFORMATION: Synthetic Scaffold
<220> FEATURE:
<221> NAME/KEY: misc_feature
<222> LOCATION: (36)..(44)
<223> OTHER INFORMATION: Xaa can be any naturally occurring amino acid
<220> FEATURE:
<221> NAME/KEY: misc_feature
<222> LOCATION: (70)..(78)
<223> OTHER INFORMATION: Xaa can be any naturally occurring amino acid

<400> SEQUENCE: 6

Asn Ser Leu Glu Ile Glu Glu Leu Ala Arg Phe Ala Val Asp Glu His
1               5                   10                  15

Asn Lys Lys Glu Asn Ala Leu Leu Glu Phe Val Arg Val Val Lys Ala
            20                  25                  30

Lys Glu Gln Xaa Xaa Xaa Xaa Xaa Xaa Xaa Xaa Thr Met Tyr Tyr
        35                  40                  45

Leu Thr Leu Glu Ala Lys Asp Gly Gly Lys Lys Lys Leu Tyr Glu Ala
    50                  55                  60

Lys Val Trp Val Lys Xaa Xaa Xaa Xaa Xaa Xaa Xaa Xaa Asn Phe
65                  70                  75                  80
```

Lys Glu Leu Gln Glu Phe Lys Pro Val Gly Asp Ala
            85                  90

<210> SEQ ID NO 7
<211> LENGTH: 183
<212> TYPE: DNA
<213> ORGANISM: Artificial Sequence
<220> FEATURE:
<223> OTHER INFORMATION: Synthetic sequence

<400> SEQUENCE: 7
aacgctctgc tggaattcgt tcgtgttgtt aaagctaaag aacaggttgt tgctggtacc      60
atgtactacc tgaccctgga agctaaagac ggtggtaaaa agaaactgta cgaagctaaa     120
gtttgggtta accgtgggaa aacttcaaa gaactgcagg agttcaaacc ggttggtgac     180
gct                                                                   183

<210> SEQ ID NO 8
<211> LENGTH: 252
<212> TYPE: DNA
<213> ORGANISM: Artificial Sequence
<220> FEATURE:
<223> OTHER INFORMATION: Synthetic sequence

<400> SEQUENCE: 8
ggtaacgaaa actccctgga aatcgaagaa ctggctcgtt tcgctgttga cgaacacaac      60
aaaaaagaaa acgctctgct ggaattcgtt cgtgttgtta aagctaaaga acaggttgtt     120
gctggtacca tgtactacct gaccctggaa gctaaagacg gtggtaaaaa gaaactgtac     180
gaagctaaag tttgggttaa accgtgggaa aacttcaaag aactgcagga gttcaaaccg     240
gttggtgacg ct                                                         252

<210> SEQ ID NO 9
<211> LENGTH: 276
<212> TYPE: DNA
<213> ORGANISM: Artificial Sequence
<220> FEATURE:
<223> OTHER INFORMATION: Synthetic sequence

<400> SEQUENCE: 9
gctaccggtg ttcgtgcagt tccgggtaac gaaaactccc tggaaatcga agaactggct      60
cgtttcgctg ttgacgaaca caacaaaaaa gaaaacgctc tgctggaatt cgttcgtgtt     120
gttaaagcta agaacaggt tgttgctggt accatgtact acctgaccct ggaagctaaa     180
gacggtggta aaagaaact gtacgaagct aaagtttggg ttaaaccgtg gaaaaacttc     240
aaagaactgc aggagttcaa accggttggt gacgct                               276

<210> SEQ ID NO 10
<211> LENGTH: 44
<212> TYPE: DNA
<213> ORGANISM: Artificial Sequence
<220> FEATURE:
<223> OTHER INFORMATION: Primer cewcF

<400> SEQUENCE: 10
attagcggcc cagccggcca tgccagcga ggaccgctcc cggc                       44

<210> SEQ ID NO 11
<211> LENGTH: 38
<212> TYPE: DNA
<213> ORGANISM: Artificial Sequence
<220> FEATURE:
<223> OTHER INFORMATION: primer cewcR

<400> SEQUENCE: 11
cgctgtactt gcggccgccc tggcacttgc tttccagc                                38

<210> SEQ ID NO 12
<211> LENGTH: 35
<212> TYPE: DNA
<213> ORGANISM: Artificial Sequence
<220> FEATURE:
<223> OTHER INFORMATION: HisF oligonucleotide

<400> SEQUENCE: 12
ggccgcagag gatcgcatca ccatcaccat cacgg                                  35

<210> SEQ ID NO 13
<211> LENGTH: 35
<212> TYPE: DNA
<213> ORGANISM: Artificial Sequence
<220> FEATURE:
<223> OTHER INFORMATION: HisR oligonucleotide

<400> SEQUENCE: 13
ggccccgtga tggtgatggt gatgcgatcc tctgc                                  35

<210> SEQ ID NO 14
<211> LENGTH: 33
<212> TYPE: DNA
<213> ORGANISM: Artificial Sequence
<220> FEATURE:
<223> OTHER INFORMATION: XhoF primer

<400> SEQUENCE: 14
atcacgctcg agcagaacaa aaactcatct cag                                    33

<210> SEQ ID NO 15
<211> LENGTH: 35
<212> TYPE: DNA
<213> ORGANISM: Artificial Sequence
<220> FEATURE:
<223> OTHER INFORMATION: XhoR primer

<400> SEQUENCE: 15
tgttctgctc gagcgtgatg gtgatggtga tggcg                                  35

<210> SEQ ID NO 16
<211> LENGTH: 21
<212> TYPE: DNA
<213> ORGANISM: Artificial Sequence
<220> FEATURE:
<223> OTHER INFORMATION: BamHIR primer

<400> SEQUENCE: 16
tggccttgat attcacaaac g                                                 21

<210> SEQ ID NO 17
<211> LENGTH: 24
<212> TYPE: DNA
<213> ORGANISM: Artificial Sequence
<220> FEATURE:
<223> OTHER INFORMATION: M13R primer

<400> SEQUENCE: 17
agcggataac aatttcacac agga                                              24

```
<210> SEQ ID NO 18
<211> LENGTH: 25
<212> TYPE: DNA
<213> ORGANISM: Artificial Sequence
<220> FEATURE:
<223> OTHER INFORMATION: CystaSDFW primer

<400> SEQUENCE: 18
caccatgaaa tcactattgc ttacg                                             25

<210> SEQ ID NO 19
<211> LENGTH: 26
<212> TYPE: DNA
<213> ORGANISM: Artificial Sequence
<220> FEATURE:
<223> OTHER INFORMATION: CystaSDREV primer

<400> SEQUENCE: 19
ctactagtga tggtgatggt gatgcg                                            26

<210> SEQ ID NO 20
<211> LENGTH: 26
<212> TYPE: PRT
<213> ORGANISM: Artificial Sequence
<220> FEATURE:
<223> OTHER INFORMATION: HIS tag

<400> SEQUENCE: 20

Arg Gly Ser His His His His His His Ala Arg Ala Glu Gln Lys Leu
1               5                   10                  15

Ile Ser Glu Glu Asp Leu Asn Gly Ala Ala
            20                  25

<210> SEQ ID NO 21
<211> LENGTH: 18
<212> TYPE: DNA
<213> ORGANISM: Artificial Sequence
<220> FEATURE:
<223> OTHER INFORMATION: Forward primer

<400> SEQUENCE: 21
tctggcgttt tctgcgtc                                                     18

<210> SEQ ID NO 22
<211> LENGTH: 21
<212> TYPE: DNA
<213> ORGANISM: Artificial Sequence
<220> FEATURE:
<223> OTHER INFORMATION: Reverse primer

<400> SEQUENCE: 22
ctgttctttc gctttaacaa c                                                 21

<210> SEQ ID NO 23
<211> LENGTH: 69
<212> TYPE: DNA
<213> ORGANISM: Artificial Sequence
<220> FEATURE:
<223> OTHER INFORMATION: Forward loop primer
<220> FEATURE:
<221> NAME/KEY: misc_feature
<222> LOCATION: (22)..(48)
<223> OTHER INFORMATION: n is a, c, g, or t

<400> SEQUENCE: 23
gttgttaaag cgaaagaaca gnnnnnnnnn nnnnnnnnnn nnnnnnnnac catgtaccac       60
``` ttgaccctg    69

<210> SEQ ID NO 24
<211> LENGTH: 78
<212> TYPE: DNA
<213> ORGANISM: Artificial Sequence
<220> FEATURE:
<223> OTHER INFORMATION: Reverse loop primer
<220> FEATURE:
<221> NAME/KEY: misc_feature
<222> LOCATION: (30)..(56)
<223> OTHER INFORMATION: n is a, c, g, or t

<400> SEQUENCE: 24
ctgcggaact cctgcagttc tttgaagttn nnnnnnnnn nnnnnnnnn nnnnnnctta    60 acccaaactt tcgcttcg    78

<210> SEQ ID NO 25
<211> LENGTH: 9
<212> TYPE: PRT
<213> ORGANISM: Artificial Sequence
<220> FEATURE:
<223> OTHER INFORMATION: Loop peptide

<400> SEQUENCE: 25

Trp Asp Leu Thr Gly Asn Val Asp Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Loop peptide

<400> SEQUENCE: 26

Ile Asp Leu Thr Asn Ser Phe Ala Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Loop peptide

<400> SEQUENCE: 27

Ile Asn Leu Met Met Val Ser Pro Met
1               5

<210> SEQ ID NO 28
<211> LENGTH: 9
<212> TYPE: PRT
<213> ORGANISM: Artificial Sequence
<220> FEATURE:
<223> OTHER INFORMATION: Loop peptide

<400> SEQUENCE: 28

Ile Asp Leu Thr His Ser Leu Asn Tyr
1               5

<210> SEQ ID NO 29
<211> LENGTH: 9
<212> TYPE: PRT
<213> ORGANISM: Artificial Sequence
<220> FEATURE:

```
<223> OTHER INFORMATION: Loop peptide

<400> SEQUENCE: 29

Ile Asp Leu Thr His Ser Leu Asn Tyr
1               5

<210> SEQ ID NO 30
<211> LENGTH: 9
<212> TYPE: PRT
<213> ORGANISM: Artificial Sequence
<220> FEATURE:
<223> OTHER INFORMATION: Loop peptide

<400> SEQUENCE: 30

Ile Asp Leu Thr Glu Trp Gln Asp Arg
1               5

<210> SEQ ID NO 31
<211> LENGTH: 9
<212> TYPE: PRT
<213> ORGANISM: Artificial Sequence
<220> FEATURE:
<223> OTHER INFORMATION: Loop peptide

<400> SEQUENCE: 31

Trp Val Asp Met Asp Tyr Tyr Trp Arg
1               5

<210> SEQ ID NO 32
<211> LENGTH: 9
<212> TYPE: PRT
<213> ORGANISM: Artificial Sequence
<220> FEATURE:
<223> OTHER INFORMATION: Loop peptide

<400> SEQUENCE: 32

Ile Asp Leu Thr Gln Thr Glu Ile Val
1               5

<210> SEQ ID NO 33
<211> LENGTH: 9
<212> TYPE: PRT
<213> ORGANISM: Artificial Sequence
<220> FEATURE:
<223> OTHER INFORMATION: Loop peptide

<400> SEQUENCE: 33

Ile Asp Leu Thr Asp Val Trp Ile Asp
1               5

<210> SEQ ID NO 34
<211> LENGTH: 9
<212> TYPE: PRT
<213> ORGANISM: Artificial Sequence
<220> FEATURE:
<223> OTHER INFORMATION: Loop peptide

<400> SEQUENCE: 34

Ile Ile Ile His Glu Asn Asp Ala Asp
1               5

<210> SEQ ID NO 35
<211> LENGTH: 9
<212> TYPE: PRT
<213> ORGANISM: Artificial Sequence
<220> FEATURE:
<223> OTHER INFORMATION: Loop peptide
```

```
<400> SEQUENCE: 35

Trp Ile Leu Asn Asn Thr Gln Phe Ile
1               5

<210> SEQ ID NO 36
<211> LENGTH: 9
<212> TYPE: PRT
<213> ORGANISM: Artificial Sequence
<220> FEATURE:
<223> OTHER INFORMATION: Loop peptide

<400> SEQUENCE: 36

Trp Tyr Glu Arg Ser Glu Asn Trp Asp
1               5

<210> SEQ ID NO 37
<211> LENGTH: 9
<212> TYPE: PRT
<213> ORGANISM: Artificial Sequence
<220> FEATURE:
<223> OTHER INFORMATION: Loop peptide

<400> SEQUENCE: 37

Trp Asp Leu Thr Thr Pro Ile Asn Ile
1               5

<210> SEQ ID NO 38
<211> LENGTH: 9
<212> TYPE: PRT
<213> ORGANISM: Artificial Sequence
<220> FEATURE:
<223> OTHER INFORMATION: Loop peptide

<400> SEQUENCE: 38

Trp Phe Asp Asp Glu Tyr Asp Trp Ile
1               5

<210> SEQ ID NO 39
<211> LENGTH: 9
<212> TYPE: PRT
<213> ORGANISM: Artificial Sequence
<220> FEATURE:
<223> OTHER INFORMATION: Loop peptide

<400> SEQUENCE: 39

Ile Asp Leu Thr Gln Pro His Asp Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Loop peptide

<400> SEQUENCE: 40

Ile Asp Leu Thr Gln Ser Phe Asp Met
1               5

<210> SEQ ID NO 41
<211> LENGTH: 9
<212> TYPE: PRT
<213> ORGANISM: Artificial Sequence
<220> FEATURE:
<223> OTHER INFORMATION: Loop peptide
```

```
<400> SEQUENCE: 41

Trp Tyr Leu Leu Asp Val Met Asp Asp
1               5

<210> SEQ ID NO 42
<211> LENGTH: 9
<212> TYPE: PRT
<213> ORGANISM: Artificial Sequence
<220> FEATURE:
<223> OTHER INFORMATION: Loop peptide

<400> SEQUENCE: 42

Trp Ile Asp Arg Gly Gln Tyr Trp Asp
1               5

<210> SEQ ID NO 43
<211> LENGTH: 9
<212> TYPE: PRT
<213> ORGANISM: Artificial Sequence
<220> FEATURE:
<223> OTHER INFORMATION: Loop peptide

<400> SEQUENCE: 43

Trp Ser Glu Ala Asp Asn Asp Trp His
1               5

<210> SEQ ID NO 44
<211> LENGTH: 9
<212> TYPE: PRT
<213> ORGANISM: Artificial Sequence
<220> FEATURE:
<223> OTHER INFORMATION: Loop peptide

<400> SEQUENCE: 44

Ile Asp Leu Thr Gly Gln Trp Leu Phe
1               5

<210> SEQ ID NO 45
<211> LENGTH: 9
<212> TYPE: PRT
<213> ORGANISM: Artificial Sequence
<220> FEATURE:
<223> OTHER INFORMATION: Loop peptide

<400> SEQUENCE: 45

Ile Asp Leu Thr Gln Ser Phe Asp Met
1               5

<210> SEQ ID NO 46
<211> LENGTH: 9
<212> TYPE: PRT
<213> ORGANISM: Artificial Sequence
<220> FEATURE:
<223> OTHER INFORMATION: Loop peptide

<400> SEQUENCE: 46

Ile Asp Leu Thr Gln Ser Phe Asp Met
1               5

<210> SEQ ID NO 47
<211> LENGTH: 9
<212> TYPE: PRT
<213> ORGANISM: Artificial Sequence
<220> FEATURE:
<223> OTHER INFORMATION: Loop peptide

<400> SEQUENCE: 47
```

```
Ile Asp Leu Thr Gln Pro His Asp Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Loop peptide

<400> SEQUENCE: 48

Trp Glu Asp Phe Gln Thr His Trp Glu
1               5

<210> SEQ ID NO 49
<211> LENGTH: 9
<212> TYPE: PRT
<213> ORGANISM: Artificial Sequence
<220> FEATURE:
<223> OTHER INFORMATION: Loop peptide

<400> SEQUENCE: 49

Trp Asp Asp Trp Gly Glu Arg Phe Trp
1               5

<210> SEQ ID NO 50
<211> LENGTH: 9
<212> TYPE: PRT
<213> ORGANISM: Artificial Sequence
<220> FEATURE:
<223> OTHER INFORMATION: Loop peptide

<400> SEQUENCE: 50

Asp Ile Asn Gln Tyr Trp His Ser Met
1               5

<210> SEQ ID NO 51
<211> LENGTH: 9
<212> TYPE: PRT
<213> ORGANISM: Artificial Sequence
<220> FEATURE:
<223> OTHER INFORMATION: Loop peptide

<400> SEQUENCE: 51

Gly Ile Gln Gln Asn Pro Ser His Ala
1               5

<210> SEQ ID NO 52
<211> LENGTH: 9
<212> TYPE: PRT
<213> ORGANISM: Artificial Sequence
<220> FEATURE:
<223> OTHER INFORMATION: Loop peptide

<400> SEQUENCE: 52

Gly Leu Thr Asn Glu Ile Gln Lys Met
1               5

<210> SEQ ID NO 53
<211> LENGTH: 9
<212> TYPE: PRT
<213> ORGANISM: Artificial Sequence
<220> FEATURE:
<223> OTHER INFORMATION: Loop peptide

<400> SEQUENCE: 53
```

Gly Leu Thr Asn Glu Ile Gln Lys Met
1               5

<210> SEQ ID NO 54
<211> LENGTH: 9
<212> TYPE: PRT
<213> ORGANISM: Artificial Sequence
<220> FEATURE:
<223> OTHER INFORMATION: Loop peptide

<400> SEQUENCE: 54

Pro Glu Pro Ile His Ser His His Ser
1               5

<210> SEQ ID NO 55
<211> LENGTH: 9
<212> TYPE: PRT
<213> ORGANISM: Artificial Sequence
<220> FEATURE:
<223> OTHER INFORMATION: Loop peptide

<400> SEQUENCE: 55

Met Asp Glu Ile Trp Ala Glu Tyr Ala
1               5

<210> SEQ ID NO 56
<211> LENGTH: 9
<212> TYPE: PRT
<213> ORGANISM: Artificial Sequence
<220> FEATURE:
<223> OTHER INFORMATION: Loop peptide

<400> SEQUENCE: 56

Glu Pro Gly Ile Ile Pro Ile Val His
1               5

<210> SEQ ID NO 57
<211> LENGTH: 9
<212> TYPE: PRT
<213> ORGANISM: Artificial Sequence
<220> FEATURE:
<223> OTHER INFORMATION: Loop peptide

<400> SEQUENCE: 57

Gly Leu Met Thr Gln Thr Asn Ser Met
1               5

<210> SEQ ID NO 58
<211> LENGTH: 9
<212> TYPE: PRT
<213> ORGANISM: Artificial Sequence
<220> FEATURE:
<223> OTHER INFORMATION: Loop peptide

<400> SEQUENCE: 58

Gly Ile Met Asp Gly Leu Asn Lys Tyr
1               5

<210> SEQ ID NO 59
<211> LENGTH: 10
<212> TYPE: PRT
<213> ORGANISM: Artificial Sequence
<220> FEATURE:
<223> OTHER INFORMATION: Loop peptide

<400> SEQUENCE: 59

Val Leu Glu Gly Pro Asp Arg Trp Thr Val

<210> SEQ ID NO 60
<211> LENGTH: 9
<212> TYPE: PRT
<213> ORGANISM: Artificial Sequence
<220> FEATURE:
<223> OTHER INFORMATION: Loop peptide

<400> SEQUENCE: 60

Arg Asp Tyr Gly Phe Thr Leu Val Pro
1               5

<210> SEQ ID NO 61
<211> LENGTH: 9
<212> TYPE: PRT
<213> ORGANISM: Artificial Sequence
<220> FEATURE:
<223> OTHER INFORMATION: Loop peptide

<400> SEQUENCE: 61

Tyr Glu Asp Tyr Gln Thr Pro Met Tyr
1               5

<210> SEQ ID NO 62
<211> LENGTH: 9
<212> TYPE: PRT
<213> ORGANISM: Artificial Sequence
<220> FEATURE:
<223> OTHER INFORMATION: Loop peptide

<400> SEQUENCE: 62

Asp Tyr Ala Ala Thr Asp Leu Tyr Trp
1               5

<210> SEQ ID NO 63
<211> LENGTH: 9
<212> TYPE: PRT
<213> ORGANISM: Artificial Sequence
<220> FEATURE:
<223> OTHER INFORMATION: Loop peptide

<400> SEQUENCE: 63

Tyr Glu Glu Asp Glu Tyr Trp Arg Met
1               5

<210> SEQ ID NO 64
<211> LENGTH: 9
<212> TYPE: PRT
<213> ORGANISM: Artificial Sequence
<220> FEATURE:
<223> OTHER INFORMATION: Loop peptide

<400> SEQUENCE: 64

Pro Ile Asp Ser Asn Phe Thr Gly Thr
1               5

<210> SEQ ID NO 65
<211> LENGTH: 9
<212> TYPE: PRT
<213> ORGANISM: Artificial Sequence
<220> FEATURE:
<223> OTHER INFORMATION: Loop peptide

<400> SEQUENCE: 65

His Asp Arg Arg Tyr Lys Gln Ala Glu
1               5

<210> SEQ ID NO 66
<211> LENGTH: 9
<212> TYPE: PRT
<213> ORGANISM: Artificial Sequence
<220> FEATURE:
<223> OTHER INFORMATION: Loop peptide

<400> SEQUENCE: 66

Ile His Asn Gly Tyr Thr Ile Met Asp
1               5

<210> SEQ ID NO 67
<211> LENGTH: 9
<212> TYPE: PRT
<213> ORGANISM: Artificial Sequence
<220> FEATURE:
<223> OTHER INFORMATION: Loop peptide

<400> SEQUENCE: 67

Leu Asp Leu Glu Thr Trp Gln His Phe
1               5

<210> SEQ ID NO 68
<211> LENGTH: 9
<212> TYPE: PRT
<213> ORGANISM: Artificial Sequence
<220> FEATURE:
<223> OTHER INFORMATION: Loop peptide

<400> SEQUENCE: 68

Pro Leu Trp Gln Tyr Asp Ala Gln Tyr
1               5

<210> SEQ ID NO 69
<211> LENGTH: 9
<212> TYPE: PRT
<213> ORGANISM: Artificial Sequence
<220> FEATURE:
<223> OTHER INFORMATION: Loop peptide

<400> SEQUENCE: 69

Pro Leu Trp Gln Tyr Asp Ala Gln Tyr
1               5

<210> SEQ ID NO 70
<211> LENGTH: 9
<212> TYPE: PRT
<213> ORGANISM: Artificial Sequence
<220> FEATURE:
<223> OTHER INFORMATION: Loop peptide

<400> SEQUENCE: 70

Pro Ile Asp Ser Asn Phe Thr Gly Thr
1               5

<210> SEQ ID NO 71
<211> LENGTH: 9
<212> TYPE: PRT
<213> ORGANISM: Artificial Sequence
<220> FEATURE:
<223> OTHER INFORMATION: Loop peptide

<400> SEQUENCE: 71

Pro His Asp Glu Leu Asn Trp Asn Met
1               5

```
<210> SEQ ID NO 72
<211> LENGTH: 9
<212> TYPE: PRT
<213> ORGANISM: Artificial Sequence
<220> FEATURE:
<223> OTHER INFORMATION: Loop peptide

<400> SEQUENCE: 72

Asp Val Gly Gln Leu Leu Ser Gly Ile
1               5

<210> SEQ ID NO 73
<211> LENGTH: 7
<212> TYPE: PRT
<213> ORGANISM: Artificial Sequence
<220> FEATURE:
<223> OTHER INFORMATION: SUMO1 binding site

<400> SEQUENCE: 73

Val Asp Val Ile Asp Leu Thr
1               5

<210> SEQ ID NO 74
<211> LENGTH: 101
<212> TYPE: PRT
<213> ORGANISM: Artificial Sequence
<220> FEATURE:
<223> OTHER INFORMATION: Synthetic Scaffold

<400> SEQUENCE: 74

Ala Thr Gly Val Arg Ala Val Pro Gly Asn Glu Asn Ser Leu Glu Ile
1               5                   10                  15

Glu Glu Leu Ala Arg Phe Ala Val Asp Glu His Asn Lys Lys Glu Asn
            20                  25                  30

Ala Leu Leu Glu Phe Val Arg Val Val Lys Ala Lys Glu Gln Val Val
        35                  40                  45

Ala Gly Thr Met Tyr Tyr Leu Thr Leu Glu Ala Lys Asp Gly Gly Lys
    50                  55                  60

Lys Lys Leu Tyr Glu Ala Lys Val Trp Val Lys Pro Trp Glu Asn Phe
65                  70                  75                  80

Lys Glu Leu Gln Glu Phe Lys Pro Val Gly Asp Ala Ala Ala His
                85                  90                  95

His His His His His
            100

<210> SEQ ID NO 75
<211> LENGTH: 93
<212> TYPE: PRT
<213> ORGANISM: Artificial Sequence
<220> FEATURE:
<223> OTHER INFORMATION: Synthetic scaffold

<400> SEQUENCE: 75

Gly Asn Glu Asn Ser Leu Glu Ile Glu Glu Leu Ala Arg Phe Ala Val
1               5                   10                  15

Asp Glu His Asn Lys Lys Glu Asn Ala Leu Leu Glu Phe Val Arg Val
            20                  25                  30

Val Lys Ala Lys Glu Gln Val Val Ala Gly Thr Met Tyr Tyr Leu Thr
        35                  40                  45

Leu Glu Ala Lys Asp Gly Gly Lys Lys Lys Leu Tyr Glu Ala Lys Val
    50                  55                  60
```

Trp Val Lys Pro Trp Glu Asn Phe Lys Glu Leu Gln Glu Phe Lys Pro
65                  70                  75                  80

Val Gly Asp Ala Ala Ala Ala His His His His His His
                85                  90

<210> SEQ ID NO 76
<211> LENGTH: 90
<212> TYPE: PRT
<213> ORGANISM: Artificial Sequence
<220> FEATURE:
<223> OTHER INFORMATION: Synthetic scaffold

<400> SEQUENCE: 76

Asn Ser Leu Glu Ile Glu Glu Leu Ala Arg Phe Ala Val Asp Glu His
1               5                   10                  15

Asn Lys Lys Glu Asn Ala Leu Leu Glu Phe Val Arg Val Lys Ala
                20                  25                  30

Lys Glu Gln Val Val Ala Gly Thr Met Tyr Tyr Leu Thr Leu Glu Ala
            35                  40                  45

Lys Asp Gly Gly Lys Lys Leu Tyr Glu Ala Lys Val Trp Val Lys
        50                  55                  60

Pro Trp Glu Asn Phe Lys Glu Leu Gln Glu Phe Lys Pro Val Gly Asp
65                  70                  75                  80

Ala Ala Ala Ala His His His His His His
                85                  90

<210> SEQ ID NO 77
<211> LENGTH: 102
<212> TYPE: PRT
<213> ORGANISM: Artificial Sequence
<220> FEATURE:
<223> OTHER INFORMATION: Synthetic scaffold

<400> SEQUENCE: 77

Met Ala Thr Gly Val Arg Ala Val Pro Gly Asn Glu Asn Ser Leu Glu
1               5                   10                  15

Ile Glu Glu Leu Ala Arg Phe Ala Val Asp Glu His Asn Lys Lys Glu
                20                  25                  30

Asn Ala Leu Leu Glu Phe Val Arg Val Val Lys Ala Lys Glu Gln Val
            35                  40                  45

Val Ala Gly Thr Met Tyr Tyr Leu Thr Leu Glu Ala Lys Asp Gly Gly
        50                  55                  60

Lys Lys Leu Tyr Glu Ala Lys Val Trp Val Lys Pro Trp Glu Asn
65                  70                  75                  80

Phe Lys Glu Leu Gln Glu Phe Lys Pro Val Gly Asp Ala Ala Ala Ala
                85                  90                  95

His His His His His His
            100

<210> SEQ ID NO 78
<211> LENGTH: 94
<212> TYPE: PRT
<213> ORGANISM: Artificial Sequence
<220> FEATURE:
<223> OTHER INFORMATION: Synthetic scaffold

<400> SEQUENCE: 78

Met Gly Asn Glu Asn Ser Leu Glu Ile Glu Glu Leu Ala Arg Phe Ala
1               5                   10                  15

Val Asp Glu His Asn Lys Lys Glu Asn Ala Leu Leu Glu Phe Val Arg

```
                    20                  25                  30

Val Val Lys Ala Lys Glu Gln Val Ala Gly Thr Met Tyr Tyr Leu
        35                  40                  45

Thr Leu Glu Ala Lys Asp Gly Gly Lys Lys Lys Leu Tyr Glu Ala Lys
50                      55                  60

Val Trp Val Lys Pro Trp Glu Asn Phe Lys Glu Leu Gln Glu Phe Lys
65                  70                  75                  80

Pro Val Gly Asp Ala Ala Ala His His His His His His
                85                  90

<210> SEQ ID NO 79
<211> LENGTH: 116
<212> TYPE: PRT
<213> ORGANISM: Artificial Sequence
<220> FEATURE:
<223> OTHER INFORMATION: Synthetic scaffold
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (51)..(59)
<223> OTHER INFORMATION: Xaa can be any naturally occurring amino acid
<220> FEATURE:
<221> NAME/KEY: misc_feature
<222> LOCATION: (85)..(93)
<223> OTHER INFORMATION: Xaa can be any naturally occurring amino acid

<400> SEQUENCE: 79

Met Xaa Xaa Xaa Xaa Xaa Xaa Val Arg Ala Val Pro Gly Asn Glu Asn
1               5                   10                  15

Ser Leu Glu Ile Glu Glu Leu Ala Arg Phe Ala Val Asp Glu His Asn
            20                  25                  30

Lys Lys Glu Asn Ala Leu Leu Glu Phe Val Arg Val Val Lys Ala Lys
        35                  40                  45

Glu Gln Xaa Xaa Xaa Xaa Xaa Xaa Xaa Xaa Thr Met Tyr Tyr Leu
    50                  55                  60

Thr Leu Glu Ala Lys Asp Gly Gly Lys Lys Lys Leu Tyr Glu Ala Lys
65                  70                  75                  80

Val Trp Val Lys Xaa Xaa Xaa Xaa Xaa Xaa Xaa Xaa Asn Phe Lys
                85                  90                  95

Glu Leu Gln Glu Phe Lys Pro Val Gly Asp Ala Ala Ala His His
                100                 105                 110

His His His His
        115

<210> SEQ ID NO 80
<211> LENGTH: 12
<212> TYPE: PRT
<213> ORGANISM: Artificial Sequence
<220> FEATURE:
<223> OTHER INFORMATION: Synthetic protein

<400> SEQUENCE: 80

Met Ala Thr Gly Val Arg Ala Val Pro Gly Asn Glu
1               5                   10

<210> SEQ ID NO 81
<211> LENGTH: 10
<212> TYPE: PRT
<213> ORGANISM: Artificial Sequence
<220> FEATURE:
```

```
<223> OTHER INFORMATION: Consensus sequence
<220> FEATURE:
<221> NAME/KEY: VARIANT
<222> LOCATION: (1)..(1)
<223> OTHER INFORMATION: Leu, Val or Ile
<220> FEATURE:
<221> NAME/KEY: VARIANT
<222> LOCATION: (2)..(2)
<223> OTHER INFORMATION: Ala, Gly or Tyr
<220> FEATURE:
<221> NAME/KEY: VARIANT
<222> LOCATION: (3)..(3)
<223> OTHER INFORMATION: Arg, Lys or Glu
<220> FEATURE:
<221> NAME/KEY: VARIANT
<222> LOCATION: (4)..(4)
<223> OTHER INFORMATION: Phe or Tyr
<220> FEATURE:
<221> NAME/KEY: VARIANT
<222> LOCATION: (5)..(5)
<223> OTHER INFORMATION: Ala or Ser
<220> FEATURE:
<221> NAME/KEY: VARIANT
<222> LOCATION: (6)..(6)
<223> OTHER INFORMATION: Val or Ile
<220> FEATURE:
<221> NAME/KEY: VARIANT
<222> LOCATION: (7)..(7)
<223> OTHER INFORMATION: Any amino acid
<220> FEATURE:
<221> NAME/KEY: VARIANT
<222> LOCATION: (8)..(8)
<223> OTHER INFORMATION: Glu, Asp, Gln or Val
<220> FEATURE:
<221> NAME/KEY: VARIANT
<222> LOCATION: (9)..(9)
<223> OTHER INFORMATION: His, Tyr, Phe or Gln

<400> SEQUENCE: 81

Xaa Xaa Xaa Xaa Xaa Xaa Xaa Xaa Xaa Asn
1               5                   10

<210> SEQ ID NO 82
<211> LENGTH: 4
<212> TYPE: PRT
<213> ORGANISM: Artificial Sequence
<220> FEATURE:
<223> OTHER INFORMATION: 'loop' amino acids

<400> SEQUENCE: 82

Val Val Ala Gly
1

<210> SEQ ID NO 83
<211> LENGTH: 5
<212> TYPE: PRT
<213> ORGANISM: Artificial Sequence
<220> FEATURE:
<223> OTHER INFORMATION: Region

<400> SEQUENCE: 83

Gln Val Val Ala Gly
1               5

<210> SEQ ID NO 84
<211> LENGTH: 11
<212> TYPE: PRT
<213> ORGANISM: Artificial Sequence
<220> FEATURE:
<223> OTHER INFORMATION: 10 amino acid peptide with a cysteine on the
      N-terminus for thiol linkage to biotin

<400> SEQUENCE: 84
```

Cys Thr His Asp Leu Tyr Met Ile Met Arg Glu
1               5                   10

<210> SEQ ID NO 85
<211> LENGTH: 62
<212> TYPE: DNA
<213> ORGANISM: Artificial Sequence
<220> FEATURE:
<223> OTHER INFORMATION: P1

<400> SEQUENCE: 85
attagcggcc cagccggcca tggccgctct gctgggtggt gttcgtgcag ttccgggtaa    60
cg                                                                  62

<210> SEQ ID NO 86
<211> LENGTH: 63
<212> TYPE: DNA
<213> ORGANISM: Artificial Sequence
<220> FEATURE:
<223> OTHER INFORMATION: P2

<400> SEQUENCE: 86
gttgtgttcg tcaacagcga acgagccac ttcttcgatt tccagggagt tttcgttacc    60
cgg                                                                 63

<210> SEQ ID NO 87
<211> LENGTH: 72
<212> TYPE: DNA
<213> ORGANISM: Artificial Sequence
<220> FEATURE:
<223> OTHER INFORMATION: P3

<400> SEQUENCE: 87
cgaacacaac aaaaaagaaa acgctctgct ggaattcgtt cgtgttgtta agctaaaga    60 acaggttgtt gc                                                       72

<210> SEQ ID NO 88
<211> LENGTH: 66
<212> TYPE: DNA
<213> ORGANISM: Artificial Sequence
<220> FEATURE:
<223> OTHER INFORMATION: P4

<400> SEQUENCE: 88
cagtttcttt ttaccaccgt ctttagcttc cagggtcagg tagtacatgg taccagcaac    60
aacctg                                                              66

<210> SEQ ID NO 89
<211> LENGTH: 64
<212> TYPE: DNA
<213> ORGANISM: Artificial Sequence
<220> FEATURE:
<223> OTHER INFORMATION: P5

<400> SEQUENCE: 89
ggtaaaaaga aactgtacga agctaaagtt tgggttaaac cgtgggaaaa cttcaaagaa    60
ctgc                                                                64

<210> SEQ ID NO 90
<211> LENGTH: 56
<212> TYPE: DNA
<213> ORGANISM: Artificial Sequence

```
<220> FEATURE:
<223> OTHER INFORMATION: P6

<400> SEQUENCE: 90
cgctgtactt gcggccgcca gcgtcaccaa ccggtttgaa ttcctgcagt tctttg          56

<210> SEQ ID NO 91
<211> LENGTH: 288
<212> TYPE: DNA
<213> ORGANISM: Artificial Sequence
<220> FEATURE:
<223> OTHER INFORMATION: PHYTC57 genetic sequence

<400> SEQUENCE: 91
atggccgctc tgctgggtgg tgttcgtgca gttccgggta acgaaaactc cctggaaatc      60
gaagaactgg ctcgtttcgc tgttgacgaa cacaacaaaa aagaaaacgc tctgctggaa     120
ttcgttcgtg ttgttaaagc taagaacag gttgttgctg gtaccatgta ctacctgacc      180
ctggaagcta agacggtgg taaaagaaa ctgtacgaag ctaaagtttg ggttaaaccg       240
tgggaaaact tcaaagaact gcaggaattc aaaccggttg gtgacgct                  288

<210> SEQ ID NO 92
<211> LENGTH: 288
<212> TYPE: DNA
<213> ORGANISM: Artificial Sequence
<220> FEATURE:
<223> OTHER INFORMATION: PHYTC57 Genetic sequence

<400> SEQUENCE: 92
agcgtcacca accggtttga attcctgcag ttctttgaag tttcccacg gtttaaccca      60 aactttagct tcgtacagtt tctttttacc accgtcttta gcttccaggg tcaggtagta     120
catggtacca gcaacaacct gttctttagc tttaacaaca cgaacgaatt ccagcagagc     180
gtttcttttt ttgttgtgtt cgtcaacagc gaaacgagcc acttcttcga tttccaggga    240
gttttcgtta cccggaactg cacgaacacc acccagcaga gcggccat                 288

<210> SEQ ID NO 93
<211> LENGTH: 101
<212> TYPE: PRT
<213> ORGANISM: Artificial Sequence
<220> FEATURE:
<223> OTHER INFORMATION: OSAIDD86

<400> SEQUENCE: 93

Met Ser Ser Asp Gly Gly Pro Val Leu Gly Gly Val Glu Pro Val Gly
1               5                   10                  15

Asn Glu Asn Asp Leu His Leu Val Asp Leu Ala Arg Phe Ala Val Thr
            20                  25                  30

Glu His Asn Lys Lys Ala Asn Ser Leu Leu Glu Phe Glu Lys Leu Val
        35                  40                  45

Ser Val Lys Gln Gln Val Val Ala Gly Thr Leu Tyr Tyr Phe Thr Ile
    50                  55                  60

Glu Val Lys Glu Gly Asp Ala Lys Lys Leu Tyr Glu Ala Lys Val Trp
65                  70                  75                  80

Glu Lys Pro Trp Met Phe Lys Glu Leu Gln Glu Phe Lys Pro Val Asp
                85                  90                  95

Ala Ser Ala Asn Ala
            100
```

<210> SEQ ID NO 94
<211> LENGTH: 96
<212> TYPE: PRT
<213> ORGANISM: Artificial Sequence
<220> FEATURE:
<223> OTHER INFORMATION: PHYTC57 genetic sequence

<400> SEQUENCE: 94

Met Ala Ala Leu Leu Gly Gly Val Arg Ala Val Pro Gly Asn Glu Asn
1               5                   10                  15

Ser Leu Glu Ile Glu Glu Leu Ala Arg Phe Ala Val Asp Glu His Asn
            20                  25                  30

Lys Lys Glu Asn Ala Leu Leu Glu Phe Val Arg Val Val Lys Ala Lys
        35                  40                  45

Glu Gln Val Val Ala Gly Thr Met Tyr Tyr Leu Thr Leu Glu Ala Lys
    50                  55                  60

Asp Gly Gly Lys Lys Leu Tyr Glu Ala Lys Val Trp Val Lys Pro
65                  70                  75                  80

Trp Glu Thr Phe Lys Glu Leu Gln Glu Phe Lys Pro Val Gly Asp Ala
                85                  90                  95

<210> SEQ ID NO 95
<211> LENGTH: 96
<212> TYPE: PRT
<213> ORGANISM: Artificial Sequence
<220> FEATURE:
<223> OTHER INFORMATION: PHYTC57

<400> SEQUENCE: 95

Met Ala Ala Leu Leu Gly Gly Val Arg Ala Val Pro Gly Asn Glu Asn
1               5                   10                  15

Ser Leu Glu Ile Glu Glu Leu Ala Arg Phe Ala Val Asp Glu His Asn
            20                  25                  30

Lys Lys Glu Asn Ala Leu Leu Glu Phe Val Arg Val Val Lys Ala Lys
        35                  40                  45

Glu Gln Val Val Ala Gly Thr Met Tyr Tyr Leu Thr Leu Glu Ala Lys
    50                  55                  60

Asp Gly Gly Lys Lys Leu Tyr Glu Ala Lys Val Trp Val Lys Pro
65                  70                  75                  80

Trp Glu Asn Phe Lys Glu Leu Gln Glu Phe Lys Pro Val Gly Asp Ala
                85                  90                  95

<210> SEQ ID NO 96
<211> LENGTH: 243
<212> TYPE: DNA
<213> ORGANISM: Artificial Sequence
<220> FEATURE:
<223> OTHER INFORMATION: Adherin 81 amino acid scaffold

<400> SEQUENCE: 96
aactccctgg aaatcgaaga actggctcgt ttcgctgttg acgaacacaa caaaaaagaa      60
aacgctctgc tggaattcgt tcgtgttgtt aaagctaaag aacaggttgt tgctggtacc     120
atgtactacc tgaccctgga agctaaagac ggtggtaaaa agaaactgta cgaagctaaa     180
gtttgggtta accgtgggaa aaacttcaaa gaactgcagg agttcaaacc ggttggtgac     240
gct                                                                   243

<210> SEQ ID NO 97
<211> LENGTH: 81
<212> TYPE: PRT

<213> ORGANISM: Artificial Sequence
<220> FEATURE:
<223> OTHER INFORMATION: Adherin 81 scaffold

<400> SEQUENCE: 97

Asn Ser Leu Glu Ile Glu Glu Leu Ala Arg Phe Ala Val Asp Glu His
1               5                   10                  15

Asn Lys Lys Glu Asn Ala Leu Leu Glu Phe Val Arg Val Val Lys Ala
                20                  25                  30

Lys Glu Gln Val Val Ala Gly Thr Met Tyr Tyr Leu Thr Leu Glu Ala
            35                  40                  45

Lys Asp Gly Gly Lys Lys Leu Tyr Glu Ala Lys Val Trp Val Lys
        50                  55                  60

Pro Trp Glu Asn Phe Lys Glu Leu Gln Glu Phe Lys Pro Val Gly Asp
65                  70                  75                  80

Ala

<210> SEQ ID NO 98
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds
      to Lectin-like oxidized LDL receptor-1 (LOX)

<400> SEQUENCE: 98

Glu Gln Thr Ala His Leu Asp Pro Leu Met Asp Thr Met Tyr Tyr Leu
1               5                   10                  15

Thr Leu Glu Ala Lys Asp Gly Gly Lys Lys Leu Tyr Glu Ala Lys
            20                  25                  30

Val Trp Val Lys Phe Trp Met Ile Ser Asp Leu Ile Phe Asn Phe Lys
            35                  40                  45

Glu Leu
    50

<210> SEQ ID NO 99
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      Lectin-like oxidized LDL receptor-1 (LOX)

<400> SEQUENCE: 99

Glu Gln Thr Ala His Leu Asp Pro Leu Met Asp Thr Met Tyr Tyr Leu
1               5                   10                  15

Thr Leu Glu Ala Lys Asp Gly Gly Lys Lys Leu Tyr Glu Ala Lys
            20                  25                  30

Val Trp Val Lys Phe Trp Met Ile Ser Asp Leu Ile Phe Asn Phe Lys
            35                  40                  45

Glu Leu
    50

<210> SEQ ID NO 100
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      Lectin-like oxidized LDL receptor-1 (LOX)

<400> SEQUENCE: 100

```
Glu Gln Thr Ala His Leu Asp Pro Leu Met Asp Thr Met Tyr Tyr Leu
1               5                   10                  15

Thr Leu Glu Ala Lys Asp Gly Gly Lys Lys Lys Leu Tyr Glu Ala Lys
            20                  25                  30

Val Trp Val Lys Phe Trp Met Ile Ser Asp Leu Ile Phe Asn Phe Lys
        35                  40                  45

Glu Leu
    50

<210> SEQ ID NO 101
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      Lectin-like oxidized LDL receptor-1 (LOX)

<400> SEQUENCE: 101

Glu Gln Thr Ala His Leu Asp Pro Leu Met Asp Thr Met Tyr Tyr Leu
1               5                   10                  15

Thr Leu Glu Ala Lys Asp Gly Gly Lys Lys Lys Leu Tyr Glu Ala Lys
            20                  25                  30

Val Trp Val Lys Phe Trp Met Ile Ser Asp Leu Ile Phe Asn Phe Lys
        35                  40                  45

Glu Leu
    50

<210> SEQ ID NO 102
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      Lectin-like oxidized LDL receptor-1 (LOX)

<400> SEQUENCE: 102

Glu Gln Thr Ala His Leu Asp Pro Leu Met Asp Thr Met Tyr Tyr Leu
1               5                   10                  15

Thr Leu Glu Ala Lys Asp Gly Gly Lys Lys Lys Leu Tyr Glu Ala Lys
            20                  25                  30

Val Trp Val Lys Phe Trp Met Ile Ser Asp Leu Ile Phe Asn Phe Lys
        35                  40                  45

Glu Leu
    50

<210> SEQ ID NO 103
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      Lectin-like oxidized LDL receptor-1 (LOX)

<400> SEQUENCE: 103

Glu Gln Thr Ala His Leu Asp Pro Leu Met Asp Thr Met Tyr Tyr Leu
1               5                   10                  15

Thr Leu Glu Ala Lys Asp Gly Gly Lys Lys Lys Leu Tyr Glu Ala Lys
            20                  25                  30

Val Trp Val Lys Phe Trp Met Ile Ser Asp Leu Ile Phe Asn Phe Lys
        35                  40                  45
```

Glu Leu
    50

<210> SEQ ID NO 104
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      Lectin-like oxidized LDL receptor-1 (LOX)

<400> SEQUENCE: 104

Glu Gln Thr Ala His Leu Asp Pro Leu Met Asp Thr Met Tyr Tyr Leu
1               5                   10                  15

Thr Leu Glu Ala Lys Asp Gly Gly Lys Lys Lys Leu Tyr Glu Ala Lys
            20                  25                  30

Val Trp Val Lys Phe Trp Met Ile Ser Asp Leu Ile Phe Asn Phe Lys
        35                  40                  45

Glu Leu
    50

<210> SEQ ID NO 105
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      Lectin-like oxidized LDL receptor-1 (LOX)

<400> SEQUENCE: 105

Glu Gln Thr His Leu Gly Met Leu Pro Pro Ile Thr Met Tyr Tyr Leu
1               5                   10                  15

Thr Leu Glu Ala Lys Asp Gly Gly Lys Lys Lys Leu Tyr Glu Ala Lys
            20                  25                  30

Val Trp Val Lys Trp Glu Asn Met Tyr Asp Phe Lys Leu Asn Phe Lys
        35                  40                  45

Glu Leu
    50

<210> SEQ ID NO 106
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      Lectin-like oxidized LDL receptor-1 (LOX)

<400> SEQUENCE: 106

Glu Gln Thr Phe Gly Arg Glu Phe Leu Gly Asp Thr Met Tyr Tyr Leu
1               5                   10                  15

Thr Leu Glu Ala Lys Asp Gly Gly Lys Lys Lys Leu Tyr Glu Ala Lys
            20                  25                  30

Val Trp Val Lys Ser Trp Leu Gln Ser Asn Lys Gln Phe Asn Phe Lys
        35                  40                  45

Glu Leu
    50

<210> SEQ ID NO 107
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to Lectin-like oxidized LDL receptor-1 (LOX)

<400> SEQUENCE: 107

Glu Gln Pro Ile Gly Glu His Pro Val Asn Asp Thr Met Tyr Tyr Leu
1               5                   10                  15

Thr Leu Glu Ala Lys Asp Gly Gly Lys Lys Lys Leu Tyr Glu Ala Lys
            20                  25                  30

Val Trp Val Lys Arg Trp Leu Arg Phe Thr Glu Ile Tyr Asn Phe Lys
        35                  40                  45

Glu Leu
    50

<210> SEQ ID NO 108
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      Lectin-like oxidized LDL receptor-1 (LOX)

<400> SEQUENCE: 108

Glu Gln Pro Ile Gly Glu His Pro Val Asn Asp Thr Met Tyr Tyr Leu
1               5                   10                  15

Thr Leu Glu Ala Lys Asp Gly Gly Lys Lys Lys Leu Tyr Glu Ala Lys
            20                  25                  30

Val Trp Val Lys Arg Trp Leu Arg Phe Thr Glu Ile Tyr Asn Phe Lys
        35                  40                  45

Glu Leu
    50

<210> SEQ ID NO 109
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      Lectin-like oxidized LDL receptor-1 (LOX)

<400> SEQUENCE: 109

Glu Gln Pro Ile Gly Glu His Pro Val Asn Asp Thr Met Tyr Tyr Leu
1               5                   10                  15

Thr Leu Glu Ala Lys Asp Gly Gly Lys Lys Lys Leu Tyr Glu Ala Lys
            20                  25                  30

Val Trp Val Lys Arg Trp Leu Arg Phe Thr Glu Ile Tyr Asn Phe Lys
        35                  40                  45

Glu Leu
    50

<210> SEQ ID NO 110
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      Lectin-like oxidized LDL receptor-1 (LOX)

<400> SEQUENCE: 110

Glu Gln Trp Asp Thr Gln Val Ser Pro Arg Asp Thr Met Tyr Tyr Leu
1               5                   10                  15

Thr Leu Glu Ala Lys Asp Gly Gly Lys Lys Lys Leu Tyr Glu Ala Lys
            20                  25                  30

Val Trp Val Lys Ser Trp Ile Tyr Ser Gly Ala Thr Tyr Asn Phe Lys
            35                  40                  45

Glu Leu
    50

<210> SEQ ID NO 111
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      Lectin-like oxidized LDL receptor-1 (LOX)

<400> SEQUENCE: 111

Glu Gln Arg Trp Gly Val Trp Glu Thr Met Asp Thr Met Tyr Tyr Leu
1               5                   10                  15

Thr Leu Glu Ala Lys Asp Gly Gly Lys Lys Leu Tyr Glu Ala Lys
            20                  25                  30

Val

```
<213> ORGANISM: Artificial Sequence
<220> FEATURE:
<223> OTHER INFORMATION: LOOP1 and LOOP2 region of Adherin that binds to
      Lectin-like oxidized LDL receptor-1 (LOX)

<400> SEQUENCE: 114

Glu Gln Trp Gly Val Arg Pro Met Pro Val Asp Thr Met Tyr Tyr Leu
1               5                   10                  15

Thr Leu Glu Ala Lys Asp Gly Gly Lys Lys Lys Leu Tyr Glu Ala Lys
            20                  25                  30

Val Trp Val Lys Trp Trp Val Tyr Ala Gly His Tyr Arg Asn Phe Lys
        35                  40                  45

Glu Leu
    50

<210> SEQ ID NO 115
<211> LENGTH: 39
<212> TYPE: PRT
<213> ORGANISM: Artificial Sequence
<220> FEATURE:
<223> OTHER INFORMATION: LOOP1 and LOOP2 region of Adherin that binds to
      Lectin-like oxidized LDL receptor-1 (LOX)

<400> SEQUENCE: 115

Glu Gln Thr Pro Asp Thr Met Tyr Tyr Leu Thr Leu Glu Ala Lys Asp
1               5                   10                  15

Gly Gly Lys Lys Lys Leu Tyr Glu Ala Lys Val Trp Val Lys Trp Ile
            20                  25                  30

Ser Ile Asn Phe Lys Glu Leu
        35

<210> SEQ ID NO 116
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 116

Lys Glu Gln Ala Thr Asp Ser Glu His Trp Trp Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Asn Ile Gly Leu Glu Met Leu Pro His Asn Phe
        35                  40                  45

Lys Glu Leu Gln
    50

<210> SEQ ID NO 117
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 117

Lys Glu Gln Ile Thr Asp Ser Ser Pro Trp Trp Trp Thr Met Tyr Tyr
1               5                   10                  15

Leu Thr Leu Glu Ala Lys Asp Gly Gly Lys Lys Lys Leu Tyr Glu Ala
            20                  25                  30
```

```
Lys Val Trp Val Lys Pro Ala Asp Leu Thr Gly Asp Lys Arg Asn Phe
            35                  40                  45

Lys Glu Leu Gln
    50

<210> SEQ ID NO 118
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 118

Lys Glu Gln Trp Ala Arg Pro Pro Asn Trp Trp Trp Thr Met Tyr Tyr
1               5                  10                  15

Leu Thr Leu Glu Ala Lys Asp Gly Gly Lys Lys Lys Leu Tyr Glu Ala
            20                  25                  30

Lys Val Trp Val Lys Gly Phe Asn Asn Asp Ser Leu Phe Arg Asn Phe
            35                  40                  45

Lys Glu Leu Gln
    50

<210> SEQ ID NO 119
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 119

Lys Glu Gln Gly His Ala Arg Ala Asp Trp Trp Trp Thr Met Tyr Tyr
1               5                  10                  15

Leu Thr Leu Glu Ala Lys Asp Gly Gly Lys Lys Lys Leu Tyr Glu Ala
            20                  25                  30

Lys Val Trp Val Lys Asp Gly Ile Trp Thr Gly Gly Arg Ala Asn Phe
            35                  40                  45

Lys Glu Leu Gln
    50

<210> SEQ ID NO 120
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 120

Lys Glu Gln Asp Val Lys Pro Asn Glu Trp Trp Trp Thr Met Tyr Tyr
1               5                  10                  15

Leu Thr Leu Glu Ala Lys Asp Gly Gly Lys Lys Lys Leu Tyr Glu Ala
            20                  25                  30

Lys Val Trp Val Lys Asp Gln Trp Tyr Thr Arg Pro Tyr Thr Asn Phe
            35                  40                  45

Lys Glu Leu Gln
    50

<210> SEQ ID NO 121
<211> LENGTH: 52
<212> TYPE: PRT
```

```
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 121

Lys Glu Gln Arg Ser Asp Gln Pro Met Trp Trp Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Asp Arg Met Gly Ser Tyr Tyr Phe Ala Asn Phe
        35                  40                  45

Lys Glu Leu Gln
    50

<210> SEQ ID NO 122
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 122

Lys Glu Gln Asp Asn Asp Asp Trp Leu Trp Trp Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Asp Arg Arg Trp Thr Tyr Asp Asn Thr Asn Phe
        35                  40                  45

Lys Glu Leu Gln
    50

<210> SEQ ID NO 123
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 123

Lys Glu Gln Gly Phe Asp Lys Asp Thr Trp Pro Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Trp Met Gly Trp Asn Trp Ser Ser Thr Asn Phe
        35                  40                  45

Lys Glu Leu Gln
    50

<210> SEQ ID NO 124
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 124

Lys Glu Gln Asp Asp Gly Ser Val Tyr Trp Pro Trp Thr Met Tyr Tyr
1               5                   10                  15
```

Leu Thr Leu Glu Ala Lys Asp Gly Gly Lys Lys Leu Tyr Glu Ala
            20                  25                  30

Lys Val Trp Val Lys Ser Ile Tyr Pro Asn Thr Met Gly Trp Asn Phe
        35                  40                  45

Lys Glu Leu Gln
        50

<210> SEQ ID NO 125
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 125

Lys Glu Gln Pro Asp Val His Glu Trp Trp Pro Trp Thr Met Tyr Tyr
1               5                   10                  15

Leu Thr Leu Glu Ala Lys Asp Gly Gly Lys Lys Leu Tyr Glu Ala
            20                  25                  30

Lys Val Trp Val Lys Asp His Gly Tyr Gln Arg Gly Trp Arg Asn Phe
        35                  40                  45

Lys Glu Leu Gln
        50

<210> SEQ ID NO 126
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 126

Lys Glu Gln Thr Asp His Ser Glu Met Trp Pro Trp Thr Met Tyr Tyr
1               5                   10                  15

Leu Thr Leu Glu Ala Lys Asp Gly Gly Lys Lys Leu Tyr Glu Ala
            20                  25                  30

Lys Val Trp Val Lys Asp Leu Lys Tyr Lys Trp Ser Met Met Asn Phe
        35                  40                  45

Lys Glu Leu Gln
        50

<210> SEQ ID NO 127
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 127

Lys Glu Gln Met Thr Asn Thr Glu Tyr Trp Met Trp Thr Met Tyr Tyr
1               5                   10                  15

Leu Thr Leu Glu Ala Lys Asp Gly Gly Lys Lys Leu Tyr Glu Ala
            20                  25                  30

Lys Val Trp Val Lys Lys Pro Glu Tyr Thr His Asp Trp Arg Asn Phe
        35                  40                  45

Lys Glu Leu Gln
        50

```
<210> SEQ ID NO 128
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)
<220> FEATURE:
<221> NAME/KEY: misc_feature
<222> LOCATION: (52)..(52)
<223> OTHER INFORMATION: Xaa can be any naturally occurring amino acid

<400> SEQUENCE: 128

Lys Glu Gln Pro Glu Gln Asp Arg Met Trp Met Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys His Pro Arg Tyr Ser Pro Gln Pro Trp Asn Phe
        35                  40                  45

Lys Glu Leu Xaa
    50

<210> SEQ ID NO 129
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 129

Lys Glu Gln Val Arg Thr Met Gln Tyr Thr Asp Glu Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Lys Asn Trp Leu Trp Leu Leu Thr Asn Phe Lys
        35                  40                  45

Glu Leu Gln
    50

<210> SEQ ID NO 130
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid

<400> SEQUENCE: 130

Lys Glu Gln Asp Val Ala Gly Leu Pro Pro Leu Trp Thr Met Tyr Tyr
1               5                   10                  15
```

```
Leu Thr Leu Xaa Ala Lys Asp Xaa Gly Lys Lys Leu Tyr Xaa Ala
            20                  25                  30

Lys Xaa Trp Val Lys Asp Leu Leu Gly Trp His Lys Ile His Asn Phe
        35                  40                  45

Lys Glu Leu Phe
    50

<210> SEQ ID NO 131
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)
<220> FEATURE:
<221> NAME/KEY: misc_feature
<222> LOCATION: (43)..(43)
<223> OTHER INFORMATION: Xaa can be any naturally occurring amino acid

<400> SEQUENCE: 131

Lys Glu Gln Gly Tyr Asp Gly Trp Leu Ala Arg Ile Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Ala Gly Thr Glu Val Xaa Asp Pro Trp Asn Phe
        35                  40                  45

Lys Glu Leu Gln
    50

<210> SEQ ID NO 132
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 132

Lys Glu Gln Thr Glu Pro Pro His Pro Leu Met Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Trp Ser Trp Asn Pro Thr Ser Met Pro Asn Phe
        35                  40                  45

Lys Glu Leu Gln
    50

<210> SEQ ID NO 133
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 133

Lys Glu Gln Thr Glu Asp Val Arg Leu Met Phe Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Asp Leu Met His Ser Glu Leu Arg Tyr Asn Phe
        35                  40                  45
```

-continued

Lys Glu Leu Gln
    50

<210> SEQ ID NO 134
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 134

Lys Glu Gln Thr Glu Asp Val Arg Leu Met Phe Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Asp Leu Met His Ser Glu Leu Arg Tyr Asn Phe
        35                  40                  45

Lys Glu Leu Gln
    50

<210> SEQ ID NO 135
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 135

Lys Glu Gln Thr Pro Asn Ser Ala Ala Ile Phe Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Asp Met Gly Ile Asp Leu His Arg Phe Asn Phe
        35                  40                  45

Lys Glu Leu Gln
    50

<210> SEQ ID NO 136
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 136

Lys Glu Gln Thr Pro Asn Ser Ala Ala Ile Phe Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Asp Met Gly Gly Asp Leu His Arg Phe Asn Phe
        35                  40                  45

Lys Glu Leu Gln
    50

<210> SEQ ID NO 137
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to -continued Human Growth Hormone (HGH)

<400> SEQUENCE: 137

Lys Glu Gln Pro Arg Leu Gly Tyr Ile Tyr Trp Thr Met Tyr Tyr Leu
1               5                   10                  15

Thr Leu Glu Ala Lys Asp Gly Gly Lys Lys Lys Leu Tyr Glu Ala Lys
            20                  25                  30

Val Trp Val Lys Ala Met Tyr Arg Met Asn Asp Asn Arg Asn Phe Lys
        35                  40                  45

Glu Leu Gln
    50

<210> SEQ ID NO 138
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 138

Lys Glu Gln Ala Asp Trp Gly Gly Trp Pro Tyr Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Glu Leu Ala Met Lys Arg Thr Val Asn Asn Phe
        35                  40                  45

Lys Glu Leu Gln
    50

<210> SEQ ID NO 139
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 139

Lys Glu Gln Asp Asp Pro Tyr Gly Trp Ile Tyr Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Ser Asn Pro Pro Ile Phe Asp Met Pro Asn Phe
        35                  40                  45

Lys Glu Leu Gln
    50

<210> SEQ ID NO 140
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 140

Lys Glu Gln Gln Asp Phe Gly Gly Trp Val Tyr Trp Thr Met Tyr Tyr
1               5                   10                  15

Leu Thr Leu Glu Ala Lys Asp Gly Gly Lys Lys Lys Leu Tyr Glu Ala
            20                  25                  30

```
Lys Val Trp Val Lys Asp Ser Ser Trp Gln Arg Gly Phe Pro Asn Phe
            35                  40                  45

Lys Glu Leu Gln
    50

<210> SEQ ID NO 141
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 141

Lys Glu Gln Asn Asp Phe Asp Tyr Trp Leu Met Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Arg Leu Tyr Asn Asp Ser Met Gln Arg Asn Phe
            35                  40                  45

Lys Glu Leu Gln
    50

<210> SEQ ID NO 142
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 142

Lys Glu Gln Gly Pro Asn Glu Tyr His Trp Met Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Asp Gln His Tyr Thr Ser Ala Phe Gly Asn Phe
            35                  40                  45

Lys Glu Leu Gln
    50

<210> SEQ ID NO 143
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 143

Lys Glu Gln Asp Lys Thr Gln Thr Tyr Met Tyr Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Val Met Gly Asn Ser Thr Lys Phe Arg Asn Phe
            35                  40                  45

Lys Glu Leu Gln
    50

<210> SEQ ID NO 144
<211> LENGTH: 52
<212> TYPE: PRT
```

```
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 144

Lys Glu Gln Ser Val Thr Gly Gln Val Val Pro Ala Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Pro Gln Ile Gly Val Met Val Leu Tyr Asn Phe
        35                  40                  45

Lys Glu Leu Gln
    50

<210> SEQ ID NO 145
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 145

Lys Glu Gln Asp Glu Thr Asn Tyr Thr Ile Gly Trp Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Asn Trp Pro Phe Ala Thr Thr Pro Trp Asn Phe
        35                  40                  45

Lys Glu Leu Gln
    50

<210> SEQ ID NO 146
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 146

Lys Glu Gln Asp Asn Glu Trp Met Pro Met Phe His Thr Met Tyr Tyr
1               5                   10                  15

Leu Thr Leu Glu Ala Lys Asp Gly Gly Lys Lys Lys Leu Tyr Glu Ala
            20                  25                  30

Lys Val Trp Val Lys Asp Leu Arg Asp Arg Asn Thr Tyr Tyr Asn Phe
        35                  40                  45

Lys Glu Leu Gln
    50

<210> SEQ ID NO 147
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 147

Lys Glu Gln Pro Glu His Ala Ala Pro Leu Met Trp Thr Met Tyr Tyr
1               5                   10                  15
```

```
Leu Thr Leu Glu Ala Lys Asp Gly Gly Lys Lys Leu Tyr Glu Ala
            20                  25                  30

Lys Val Trp Val Lys Pro Leu Tyr Pro Met Gly Pro Tyr Arg Asn Phe
        35                  40                  45

Lys Glu Leu Gln
    50

<210> SEQ ID NO 148
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 148

Lys Glu Gln Ala Asp Leu Gly Tyr Leu Glu Leu Asn Thr Met Tyr Tyr
1               5                   10                  15

Leu Thr Leu Glu Ala Lys Asp Gly Gly Lys Lys Leu Tyr Glu Ala
            20                  25                  30

Lys Val Trp Val Lys Arg Leu Thr Asn Trp Thr Arg Leu Leu Asn Phe
        35                  40                  45

Lys Glu Leu Gln
    50

<210> SEQ ID NO 149
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 149

Lys Glu Gln Glu Glu Asn Ser Ala Met Leu Met Trp Thr Met Tyr Tyr
1               5                   10                  15

Leu Thr Leu Glu Ala Lys Asp Gly Gly Lys Lys Leu Tyr Glu Ala
            20                  25                  30

Lys Val Trp Val Lys Phe Thr Ser Met Trp Gly Gly Trp His Asn Phe
        35                  40                  45

Lys Glu Leu Gln
    50

<210> SEQ ID NO 150
<211> LENGTH: 52
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 150

Lys Glu Gln Arg Tyr Ser Gln Tyr Leu Met Trp Lys Thr Met Tyr Tyr
1               5                   10                  15

Leu Thr Leu Glu Ala Lys Asp Gly Gly Lys Lys Leu Tyr Glu Ala
            20                  25                  30

Lys Val Trp Val Lys Asp Phe Asn Asp Trp Gln Pro Ser Trp Asn Phe
        35                  40                  45

Lys Glu Leu Gln
    50
```

```
<210> SEQ ID NO 151
<211> LENGTH: 35
<212> TYPE: PRT
<213> ORGANISM: Artificial Sequence
<220> FEATURE:
<223> OTHER INFORMATION: LOOP1 and LOOP2 region of Adherin that binds to
      Human Growth Hormone (HGH)

<400> SEQUENCE: 151

Lys Glu Gln Trp Thr Met Tyr Tyr Leu Thr Leu Glu Ala Lys Asp Gly
1               5                   10                  15

Gly Lys Lys Lys Leu Tyr Glu Ala Lys Val Trp Val Lys Asn Phe Lys
            20                  25                  30

Glu Leu Gln
        35

<210> SEQ ID NO 152
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 152

Lys Glu Gln Trp Asp Leu Thr Gly Asn Val Asp Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Trp Asp Asp Trp Gly Glu Lys Phe Trp Asn Phe
        35                  40                  45

Lys Glu
    50

<210> SEQ ID NO 153
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 153

Lys Glu Gln Ile Asp Leu Thr Asn Ser Phe Ala Ser Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Asp Ile Asn Gln Tyr Trp Met Ser Met Asn Phe
        35                  40                  45

Lys Glu
    50

<210> SEQ ID NO 154
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 154

Lys Glu Gln Ile Met Leu Met Met Val Ser Pro Met Thr Met Tyr Tyr
1               5                   10                  15
```

```
Leu Thr Leu Glu Ala Lys Asp Gly Gly Trp Lys Lys Leu Tyr Glu Ala
            20                  25                  30

Lys Val Trp Val Lys Gly Ile Gln Gln Asn Pro Ser Met Ala Asn Phe
        35                  40                  45

Lys Glu
    50

<210> SEQ ID NO 155
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 155

Lys Glu Gln Ile Asp Leu Thr Lys Ser Leu Asn Tyr Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Gly Leu Thr Asn Glu Ile Gln Lys Met Asn Phe
        35                  40                  45

Lys Glu
    50

<210> SEQ ID NO 156
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 156

Lys Glu Gln Ile Asp Leu Thr Lys Ser Leu Asn Tyr Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Gly Leu Thr Asn Glu Ile Gln Lys Met Asn Phe
        35                  40                  45

Lys Glu
    50

<210> SEQ ID NO 157
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds
      to yeast small ubiquitin-like modifier (SUMO)

<400> SEQUENCE: 157

Lys Glu Gln Ile Asp Leu Thr Phe Trp Gln Asp Lys Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Pro Glu Pro Ile Lys Ser Met Met Ser Asn Phe
        35                  40                  45

Lys Glu
    50
```

<210> SEQ ID NO 158
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 158

Lys Gln Gln Trp Val Asp Met Asp Tyr Tyr Trp Lys Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Met Asp Glu Ile Trp Ala Glu Tyr Ala Asn Phe
        35                  40                  45

Lys Glu
    50

<210> SEQ ID NO 159
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 159

Lys Glu Gln Ile Asp Leu Thr Gln Thr Glu Ile Val Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Glu Pro Gly Ile Ile Pro Ile Val Met Asn Phe
        35                  40                  45

Lys Glu
    50

<210> SEQ ID NO 160
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 160

Lys Glu Gln Ile Asp Leu Thr Asp Val Trp Ile Asp Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Gly Leu Met Thr Gln Thr Asn Ser Met Asn Phe
        35                  40                  45

Lys Glu
    50

<210> SEQ ID NO 161
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 161

```
Lys Glu Gln Ile Ile Leu Lys Glu Asn Asp Ala Asp Thr Met Tyr Tyr
1               5                   10                  15

Leu Thr Leu Glu Ala Lys Asp Gly Gly Trp Lys Lys Leu Tyr Glu Ala
                20                  25                  30

Lys Val Trp Val Lys Gly Ile Met Asp Gly Leu Asn Lys Tyr Asn Phe
                35                  40                  45

Lys Glu
    50
```

<210> SEQ ID NO 162
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to yeast small ubiquitin-like modifier (SUMO)

<400> SEQUENCE: 162

```
Lys Glu Gln Trp Ile Leu Asn Asn Thr Gln Phe Ile Thr Met Tyr Tyr
1               5                   10                  15

Leu Thr Leu Glu Ala Lys Asp Gly Gly Trp Lys Lys Leu Tyr Glu Ala
                20                  25                  30

Lys Val Trp Val Lys Gly Leu Glu Gly Pro Asp Lys Trp Val Asn Phe
                35                  40                  45

Lys Glu
    50
```

<210> SEQ ID NO 163
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to yeast small ubiquitin-like modifier (SUMO)

<400> SEQUENCE: 163

```
Lys Glu Gln Trp Tyr Glu Lys Ser Glu Asn Trp Asp Thr Met Tyr Tyr
1               5                   10                  15

Leu Thr Leu Glu Ala Lys Asp Gly Gly Trp Lys Lys Leu Tyr Glu Ala
                20                  25                  30

Lys Val Trp Val Lys Lys Asp Tyr Gly Phe Thr Leu Val Pro Asn Phe
                35                  40                  45

Lys Glu
    50
```

<210> SEQ ID NO 164
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to yeast small ubiquitin-like modifier (SUMO)

<400> SEQUENCE: 164

```
Lys Glu Gln Trp Asp Leu Thr Thr Pro Ile Asn Ile Thr Met Tyr Tyr
1               5                   10                  15

Leu Thr Leu Glu Ala Lys Asp Gly Gly Trp Lys Lys Leu Tyr Glu Ala
                20                  25                  30

Lys Val Trp Val Lys Tyr Glu Asp Tyr Gln Thr Pro Met Tyr Asn Phe
                35                  40                  45

Lys Glu
```

<210> SEQ ID NO 165
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 165

Lys Glu Gln Trp Phe Asp Asp Glu Tyr Asp Trp Ile Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Asp Tyr Ala Ala Thr Asp Leu Tyr Trp Asn Phe
        35                  40                  45

Lys Glu
    50

<210> SEQ ID NO 166
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 166

Lys Glu Gln Ile Asp Leu Thr Gln Pro Lys Asp Ser Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Tyr Glu Glu Asp Glu Tyr Trp Lys Met Asn Phe
        35                  40                  45

Lys Glu
    50

<210> SEQ ID NO 167
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 167

Lys Glu Gln Ile Asp Leu Thr Gln Ser Phe Asp Met Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Pro Ile Asp Ser Asn Phe Thr Gly Thr Asn Phe
        35                  40                  45

Lys Glu
    50

<210> SEQ ID NO 168
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

```
<400> SEQUENCE: 168

Lys Glu Gln Trp Tyr Leu Leu Asp Val Met Asp Asp Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys His Asp Arg Arg Tyr Arg Gln Ala Glu Asn Phe
        35                  40                  45

Lys Glu
    50

<210> SEQ ID NO 169
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 169

Lys Glu Gln Trp Ile Asp Lys Gly Gln Tyr Trp Asp Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Ile His Asn Gly Tyr Thr Ile Met Asp Asn Phe
        35                  40                  45

Lys Glu
    50

<210> SEQ ID NO 170
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 170

Lys Glu Gln Trp Ser Glu Ala Asp Asn Asp Trp Met Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Leu Asp Leu Glu Thr Trp Gln Trp Phe Asn Phe
        35                  40                  45

Lys Glu
    50

<210> SEQ ID NO 171
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 171

Lys Glu Gln Ile Asp Leu Thr Gly Gln Trp Leu Phe Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Pro Leu Trp Gln Tyr Asp Ala Gln Tyr Asn Phe
```

-continued

```
                  35                  40                  45

Lys Glu
    50

<210> SEQ ID NO 172
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 172

Lys Glu Gln Ile Asp Leu Thr Gln Ser Phe Asp Met Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Pro Ser Arg Arg Asn Tyr Gln Thr Met Asn Phe
        35                  40                  45

Lys Glu
    50

<210> SEQ ID NO 173
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 173

Lys Glu Gln Ile Asp Leu Thr Gln Ser Phe Asp Met Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Pro Ile Asp Ser Asn Phe Thr Gly Thr Asn Phe
        35                  40                  45

Lys Glu
    50

<210> SEQ ID NO 174
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 174

Lys Glu Gln Ile Asp Leu Thr Gln Pro Lys Asp Ser Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Pro His Asp Glu Leu Asn Trp Asn Met Asn Phe
        35                  40                  45

Lys Glu
    50

<210> SEQ ID NO 175
<211> LENGTH: 50
<212> TYPE: PRT
<213> ORGANISM: Artificial Sequence
```

```
<220> FEATURE:
<223> OTHER INFORMATION: LOOP1 and LOOP2 region of Adherin that binds to
      yeast small ubiquitin-like modifier (SUMO)

<400> SEQUENCE: 175

Lys Glu Gln Trp Glu Asp Phe Gln Thr Lys Trp Glu Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Asp Val Gly Gln Leu Leu Ser Gly Ile Asn Phe
        35                  40                  45

Lys Glu
    50

<210> SEQ ID NO 176
<211> LENGTH: 36
<212> TYPE: PRT
<213> ORGANISM: Artificial Sequence
<220> FEATURE:
<223> OTHER INFORMATION: LOOP1 and LOOP2 region of Adherin that binds to
      yeast small ubiquitin-like modifier (SUMO)

<400> SEQUENCE: 176

Lys Glu Gln Ile Asp Leu Thr Thr Met Tyr Tyr Leu Thr Leu Glu Ala
1               5                   10                  15

Lys Asp Gly Gly Trp Lys Lys Leu Tyr Glu Ala Lys Val Trp Val Lys
            20                  25                  30

Asn Phe Lys Glu
        35

<210> SEQ ID NO 177
<211> LENGTH: 49
<212> TYPE: PRT
<213> ORGANISM: Artificial Sequence
<220> FEATURE:
<223> OTHER INFORMATION: LOOP1 and LOOP2 region of Adherin that binds to
      penicillin binding protein 2a (PBP2a)

<400> SEQUENCE: 177

Lys Glu Gln Asp Phe Gly Lys Glu Val Asn Met Tyr Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Thr Ile Arg Gly Lys Asn Phe Met Phe Asn Phe
        35                  40                  45

Lys

<210> SEQ ID NO 178
<211> LENGTH: 49
<212> TYPE: PRT
<213> ORGANISM: Artificial Sequence
<220> FEATURE:
<223> OTHER INFORMATION: LOOP1 and LOOP2 region of Adherin that binds to
      penicillin binding protein 2a (PBP2a)

<400> SEQUENCE: 178

Lys Glu Gln Asp Phe Gly Lys Glu Val Asn Met Tyr Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Thr Ile Arg Gly Lys Asn Phe Met Phe Asn Phe
        35                  40                  45
```

Lys

<210> SEQ ID NO 179
<211> LENGTH: 49
<212> TYPE: PRT
<213> ORGANISM: Artificial Sequence
<220> FEATURE:
<223> OTHER INFORMATION: LOOP1 and LOOP2 region of Adherin that binds to
      penicillin binding protein 2a (PBP2a)

<400> SEQUENCE: 179

Lys Glu Gln Thr Lys Ser Thr Val Ser Asp Met Glu Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Lys Tyr Trp Ile Ser His Phe Ala Leu Asn Phe
        35                  40                  45

Lys

<210> SEQ ID NO 180
<211> LENGTH: 49
<212> TYPE: PRT
<213> ORGANISM: Artificial Sequence
<220> FEATURE:
<223> OTHER INFORMATION: LOOP1 and LOOP2 region of Adherin that binds to
      penicillin binding protein 2a (PBP2a)

<400> SEQUENCE: 180

```
Lys Glu Gln Thr Lys Ser Thr Val Ser Asp Met Glu Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Lys Tyr Trp Ile Ser His Phe Ala Leu Asn Phe
        35                  40                  45

Lys
```

<210> SEQ ID NO 181
<211> LENGTH: 49
<212> TYPE: PRT
<213> ORGANISM: Artificial Sequence
<220> FEATURE:
<223> OTHER INFORMATION: LOOP1 and LOOP2 region of Adherin that binds to penicillin binding protein 2a (PBP2a)

<400> SEQUENCE: 181

```
Lys Glu Gln Tyr Tyr Asp Met Pro Glu His Leu Tyr Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Thr Phe Arg Phe Glu His Met Val Leu Asn Phe
        35                  40                  45

Lys
```

<210> SEQ ID NO 182
<211> LENGTH: 49
<212> TYPE: PRT
<213> ORGANISM: Artificial Sequence
<220> FEATURE:
<223> OTHER INFORMATION: LOOP1 and LOOP2 region of Adherin that binds to penicillin binding protein 2a (PBP2a)

<400> SEQUENCE: 182

```
Lys Glu Gln Tyr Tyr Glu Gln Leu Pro Asp Ser Pro Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Glu Met Arg Phe Gln His Phe Gln Leu Asn Phe
        35                  40                  45

Lys

<210> SEQ ID NO 183
<211> LENGTH: 49
<212> TYPE: PRT
<213> ORGANISM: Artificial Sequence
<220> FEATURE:
<223> OTHER INFORMATION: LOOP1 and LOOP2 region of Adherin that binds to
      penicillin binding protein 2a (PBP2a)

<400> SEQUENCE: 183

Lys Glu Gln Met Glu Gln His Val Asp Ile Leu Pro Thr Met Tyr Tyr
1               5                   10                  15

Leu Thr Leu Glu Ala Lys As

```
<210> SEQ ID NO 186
<211> LENGTH: 49
<212> TYPE: PRT
<213> ORGANISM: Artificial Sequence
<220> FEATURE:
<223> OTHER INFORMATION: LOOP1 and LOOP2 region of Adherin that binds to
      penicillin binding protein 2a (PBP2a)

<400> SEQUENCE: 186

Lys Glu Gln His Ala Glu Ala Tyr Pro Phe Thr Met Thr Met Tyr Tyr
1               5                   10                  15

Leu Thr Leu Glu Ala Lys Asp Gly Gly Trp Lys Lys Leu Tyr Glu Ala
            20                  25                  30

Lys Val Trp Val Lys Val Tyr Ile Phe Asn Trp Gly Gln Met Asn Phe
        35                  40                  45

Lys

<210> SEQ ID NO 187
<211> LENGTH: 49
<212> TYPE: PRT
<213> ORGANISM: Artificial Sequence
<220> FEATURE:
<223> OTHER INFORMATION: LOOP1 and LOOP2 region of Adherin that binds to
      penicillin binding protein 2a (PBP2a)

<400> SEQUENCE: 187

Lys Glu Gln Lys Thr Leu Asp Thr Phe Asp Gly Phe Thr Met Tyr Tyr
1               5                   10                  15

Leu Thr Leu Glu Ala Lys Asp Gly Gly Trp Lys Lys Leu Tyr Glu Ala
            20                  25                  30

Lys Val

```
Leu Thr Leu Glu Ala Lys Asp Gly Gly Trp Lys Lys Leu Tyr Glu Ala
            20                  25                  30

Lys Val Trp Val Lys Gln Met Tyr Phe Thr Tyr Phe Thr Met Asn Phe
        35                  40                  45

Lys
```

<210> SEQ ID NO 190
<211> LENGTH: 49
<212> TYPE: PRT
<213> ORGANISM: Artificial Sequence
<220> FEATURE:
<223> OTHER INFORMATION: LOOP1 and LOOP2 region of Adherin that binds to
      penicillin binding protein 2a (PBP2a)

<400> SEQUENCE: 190

```
Lys Glu Gln Arg Val Asp Gln Glu Ile Asp Glu Trp Thr Met Tyr Tyr
1               5                  10                  15

Leu Thr Leu Glu Ala Lys Asp Gly Gly Trp Lys Lys Leu Tyr Glu Ala
            20                  25                  30

Lys Val Trp Val Lys Ile Phe Val Phe Arg Trp Gly Ala Met Asn Phe
        35                  40                  45

Lys
```

<210> SEQ ID NO 191
<211> LENGTH: 31
<212> TYPE: PRT
<213> ORGANISM: Artificial Sequence
<220> FEATURE:
<223> OTHER INFORMATION: LOOP1 and LOOP2 region of Adherin that binds to
      penicillin binding protein 2a (PBP2a)

<400> SEQUENCE: 191

```
Lys Glu Gln Thr Met Tyr Tyr Leu Thr Leu Glu Ala Lys Asp Gly Gly
1               5                  10                  15

Trp Lys Lys Leu Tyr Glu Ala Lys Val Trp Val Lys Asn Phe Lys
            20                  25                  30
```

<210> SEQ ID NO 192
<211> LENGTH: 49
<212> TYPE: PRT
<213> ORGANISM: Artificial Sequence
<220> FEATURE:
<223> OTHER INFORMATION: LOOP1 and LOOP2 region of Adherin that binds to
      a peptide target

<400> SEQUENCE: 192

```
Glu Gln Lys Pro Thr Tyr Ala Tyr Met Glu Val Thr Met Tyr Tyr Leu
1               5                  10                  15

Thr Leu Glu Ala Lys Asp Gly Gly Lys Lys Lys Leu Tyr Glu Ala Lys
            20                  25                  30

Val Trp Val Lys Asn Trp Asp Pro Tyr Gly Met Ser Pro Asn Phe Lys
        35                  40                  45

Glu
```

<210> SEQ ID NO 193
<211> LENGTH: 49
<212> TYPE: PRT
<213> ORGANISM: Artificial Sequence
<220> FEATURE:
<223> OTHER INFORMATION: LOOP1 and LOOP2 region of Adherin that binds to
      a peptide target

<400> SEQUENCE: 193

```
Glu Gln Leu Ile Ile Asp Lys Phe His Ile Arg Thr Met Tyr Tyr Leu
1               5                   10                  15

Thr Leu Glu Ala Lys Asp Gly Gly Lys Lys Leu Tyr Glu Ala Lys
            20                  25                  30

Val Trp Val Lys Glu Glu Asp Pro Tyr Asn Met Leu Trp Asn Phe Lys
        35                  40                  45

Glu

<210> SEQ ID NO 194
<211> LENGTH: 35
<212> TYPE: PRT
<213> ORGANISM: Artificial Sequence
<220> FEATURE:
<223> OTHER INFORMATION: LOOP1 and LOOP2 region of Adherin that binds to
      a peptide target

<400> SEQUENCE: 194

Glu Gln Thr Met Tyr Tyr Leu Thr Leu Glu Ala Lys Asp Gly Gly Lys
1               5                   10                  15

Lys Lys Leu Tyr Glu Ala Lys Val Trp Val Lys Asp Pro Tyr Met Asn
            20                  25                  30

Phe Lys Glu
        35

<210> SEQ ID NO 195
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 195

Lys Ala Lys Glu Gln Arg Trp Tyr Val Asn Val Ser Leu Pro Thr Met
1               5                   10                  15

Tyr Tyr Leu Thr Leu Glu Ala Lys Asp Gly Gly Lys Lys Lys Leu Tyr
            20                  25                  30

Glu Ala Lys Val Trp Val Lys Asp Asn Met Asp Asn Met Asn Lys Ile
        35                  40                  45

Asn Phe Lys Glu Leu Gln Glu Phe
    50                  55

<210> SEQ ID NO 196
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 196

Lys Ala Lys Glu Gln Arg Trp Tyr Val Asn Val Ser Leu Pro Thr Met
1               5                   10                  15

Tyr Tyr Leu Thr Leu Glu Ala Lys Asp Gly Gly Lys Lys Lys Leu Tyr
            20                  25                  30

Glu Ala Lys Val Trp Val Lys Asp Asn Met Asp Asn Met Asn Lys Ile
        35                  40                  45

Asn Phe Lys Glu Leu Gln Glu Phe
    50                  55
```

<210> SEQ ID NO 197
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
     Growth factor receptor bound protein 2 (Grb2) Src homology 2
     domain

<400> SEQUENCE: 197

```
Lys Ala Lys Glu Gln Arg Trp Tyr Val Asn Ile Lys Phe Pro Thr Met
1               5                   10                  15

Tyr Tyr Leu Thr Leu Glu Ala Lys Asp Gly Gly Lys Lys Lys Leu Tyr
            20                  25                  30

Glu Ala Lys Val Trp Val Lys Asn Trp Thr Glu Phe Asn Ser Lys Thr
        35                  40                  45

Asn Phe Lys Glu Leu Gln Glu Phe
    50                  55
```

<210> SEQ ID NO 198
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
     Growth factor receptor bound protein 2 (Grb2) Src homology 2
     domain

<400> SEQUENCE: 198

```
Lys Ala Lys Glu Gln Lys Trp Tyr Met Asn Thr Met Phe Pro Thr Met
1               5                   10                  15

Tyr Tyr Leu Thr Leu Glu Ala Lys Asp Gly Gly Lys Lys Lys Leu Tyr
            20                  25                  30

Glu Ala Lys Val Trp Val Lys Glu Pro Gly Arg Phe Asn Glu Met Leu
        35                  40                  45

Asn Phe Lys Glu Leu Gln Glu Phe
    50                  55
```

<210> SEQ ID NO 199
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
     Growth factor receptor bound protein 2 (Grb2) Src homology 2
     domain

<400> SEQUENCE: 199

```
Lys Ala Lys Glu Gln Lys Trp Tyr Met Asn Thr Met Phe Pro Thr Met
1               5                   10                  15

Tyr Tyr Leu Thr Leu Glu Ala Lys Asp Gly Gly Lys Lys Lys Leu Tyr
            20                  25                  30

Glu Ala Lys Val Trp Val Lys Glu Pro Gly Arg Phe Asn Glu Met Leu
        35                  40                  45

Asn Phe Lys Glu Leu Gln Glu Phe
    50                  55
```

<210> SEQ ID NO 200
<211> LENGTH: 56
<212> TYPE: PRT
<213> ORGANISM: Artificial Sequence
<220> FEATURE:

-continued

<223> OTHER INFORMATION: LOOP1 and LOOP2 region of Adherin that binds to
     Growth factor receptor bound protein 2 (Grb2) Src homology 2
     domain

<400> SEQUENCE: 200

Lys Ala Lys Glu Gln Lys Trp Tyr Met Asn Thr Met Phe Pro Thr Met
1               5                   10                  15

Tyr Tyr Leu Thr Leu Glu Ala Lys Asp Gly Gly Lys Lys Lys Leu Tyr
            20                  25                  30

Glu Ala Lys Val Trp Val Lys Glu Pro Gly Arg Phe Asn Glu Met Leu
        35                  40                  45

Asn Phe Lys Glu Leu Gln Glu Phe
    50                  55

<210> SEQ ID NO 201
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
     Growth factor receptor bound protein 2 (Grb2) Src homology 2
     domain

<400> SEQUENCE: 201

Lys Ala Lys Glu Gln Lys Trp Tyr Gln Asn Val Met Phe Pro Thr Met
1               5                   10                  15

Tyr Tyr Leu Thr Leu Glu Ala Lys Asp Gly Gly Lys Lys Lys Leu Tyr
            20                  25                  30

Glu Ala Lys Val Trp Val Lys Glu Ser Ile Asp Tyr Pro Asp His Glu
        35                  40                  45

Asn Phe Lys Glu Leu Gln Glu Phe
    50                  55

<210> SEQ ID NO 202
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
     Growth factor receptor bound protein 2 (Grb2) Src homology 2
     domain

<400> SEQUENCE: 202

Lys Ala Lys Glu Gln Pro Trp Tyr Gln Asn Val Pro Tyr Pro Thr Met
1               5                   10                  15

Tyr Tyr Leu Thr Leu Glu Ala Lys Asp Gly Gly Lys Lys Lys Leu Tyr
            20                  25                  30

Glu Ala Lys Val Trp Val Lys Arg Glu Glu Arg Asn Met Asn Ala Met
        35                  40                  45

Asn Phe Lys Glu Leu Gln Glu Phe
    50                  55

<210> SEQ ID NO 203
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
     Growth factor receptor bound protein 2 (Grb2) Src homology 2
     domain

<400> SEQUENCE: 203

Lys Ala Lys Glu Gln Pro Trp Tyr Glu Asn Val Pro Tyr Pro Thr Met

```
                1               5                   10                  15
Tyr Tyr Leu Thr Leu Glu Ala Lys Asp Gly Gly Lys Lys Leu Tyr
                    20                  25                  30

Glu Ala Lys Val Trp Val Lys Asn Glu Arg Tyr Asn Val Leu His Gly
            35                  40                  45

Asn Phe Lys Glu Leu Gln Glu Phe
        50                  55

<210> SEQ ID NO 204
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 204

Lys Ala Lys Glu Gln His Trp Tyr Gln Asn Val Val Met Pro Thr Met
1               5                   10                  15

Tyr Tyr Leu Thr Leu Glu Ala Lys Asp Gly Gly Lys Lys Leu Tyr
                    20                  25                  30

Glu Ala Lys Val Trp Val Lys Ala Ile His Pro Ile Asp Ala Gln Trp
            35                  40                  45

Asn Phe Lys Glu Leu Gln Glu Phe
        50                  55

<210> SEQ ID NO 205
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 205

Lys Ala Lys Glu Gln Arg His Trp Val Asn Val Pro Phe Pro Thr Met
1               5                   10                  15

Tyr Tyr Leu Thr Leu Glu Ala Lys Asp Gly Gly Lys Lys Leu Tyr
                    20                  25                  30

Glu Ala Lys Val Trp Val Lys Gly Asp Gly Phe Asp Asn Ala Leu His
            35                  40                  45

Asn Phe Lys Glu Leu Gln Glu Phe
        50                  55

<210> SEQ ID NO 206
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 206

Lys Ala Lys Glu Gln Arg His Trp Val Asn Val Pro Phe Pro Thr Met
1               5                   10                  15

Tyr Tyr Leu Thr Leu Glu Ala Lys Asp Gly Gly Lys Lys Leu Tyr
                    20                  25                  30

Glu Ala Lys Val Trp Val Lys Gly Asp Gly Phe Asp Asn Ala Leu His
            35                  40                  45
```

```
Asn Phe Lys Glu Leu Gln Glu Phe
    50                  55

<210> SEQ ID NO 207
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 207

Lys Ala Lys Glu Gln Arg His Trp Val Asn Val Pro Phe Pro Thr Met
1               5                   10                  15

Tyr Tyr Leu Thr Leu Glu Ala Lys Asp Gly Gly Lys Lys Lys Leu Tyr
            20                  25                  30

Glu Ala Lys Val Trp Val Lys Gly Asp Gly Phe Asp Asn Ala Leu His
        35                  40                  45

Asn Phe Lys Glu Leu Gln Glu Phe
    50                  55

<210> SEQ ID NO 208
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 208

Lys Ala Lys Glu Gln Asp Trp Trp Glu Ala Gly Val Phe Met Thr Met
1               5                   10                  15

Tyr Tyr Leu Thr Leu Glu Ala Lys Asp Gly Gly Lys Lys Lys Leu Tyr
            20                  25                  30

Glu Ala Lys Val Trp Val Lys Trp Asn Glu Ile Asn Tyr Met Phe Asp
        35                  40                  45

Asn Phe Lys Glu Leu Gln Glu Phe
    50                  55

<210> SEQ ID NO 209
<211> LENGTH: 49
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 209

Lys Ala Lys Glu Gln Phe Ser His Ala Tyr Met Asn Val Val Thr Met
1               5                   10                  15

Tyr Tyr Leu Thr Leu Glu Ala Lys Asp Gly Gly Lys Lys Lys Leu Tyr
            20                  25                  30

Glu Ala Lys Val Trp Val Lys Val Gly Gly Gly Gly Asn Leu Gln Glu
        35                  40                  45

Phe

<210> SEQ ID NO 210
<211> LENGTH: 55
<212> TYPE: PRT
```

```
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 210

Lys Ala Lys Glu Gln Asp Pro Lys Lys Tyr Val Asn Val Thr Met Tyr
1               5                   10                  15

Tyr Leu Thr Leu Glu Ala Lys Asp Gly Gly Lys Lys Lys Leu Tyr Glu
            20                  25                  30

Ala Lys Val Trp Val Lys Asn Pro Val Asp Lys Phe Asp Lys Ile Asn
        35                  40                  45

Phe Lys Glu Leu Gln Glu Phe
    50                  55

<210> SEQ ID NO 211
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 211

Lys Ala Lys Glu Gln Gln Trp Tyr Trp Gln Asn Ala Val Asp Thr Met
1               5                   10                  15

Tyr Tyr Leu Thr Leu Glu Ala Lys Asp Gly Gly Lys Lys Lys Leu Tyr
            20                  25                  30

Glu Ala Lys Val Trp Val Lys Val Arg Pro Arg Gly Leu Phe Trp Asp
        35                  40                  45

Asn Phe Lys Glu Leu Gln Glu Phe
    50                  55

<210> SEQ ID NO 212
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 212

Lys Ala Lys Glu Gln Gln Trp Tyr Val Asn Thr His Ser Pro Thr Met
1               5                   10                  15

Tyr Tyr Leu Thr Leu Glu Ala Lys Asp Gly Gly Lys Lys Lys Leu Tyr
            20                  25                  30

Glu Ala Lys Val Trp Val Lys Glu Val Tyr His Ile Lys Asn Lys Arg
        35                  40                  45

Asn Phe Lys Glu Leu Gln Glu Phe
    50                  55

<210> SEQ ID NO 213
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 213
```

```
Lys Ala Lys Glu Gln Asn Lys Glu Gln Arg His Trp Ser Glu Thr Met
  1               5                  10                  15

Tyr Tyr Leu Thr Leu Glu Ala Lys Asp Gly Gly Lys Lys Lys Leu Tyr
             20                  25                  30

Glu Ala Lys Val Trp Val Lys Phe Gln Tyr Val Asn Trp Pro Val Pro
         35                  40                  45

Asn Phe Lys Glu Leu Gln Glu Phe
     50                  55

<210> SEQ ID NO 214
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 214

Lys Ala Lys Glu Gln His Glu Tyr Pro Met His Gln His Asn Thr Met
  1               5                  10                  15

Tyr Tyr Leu Thr Leu Glu Ala Lys Asp Gly Gly Lys Lys Lys Leu Tyr
             20                  25                  30

Glu Ala Lys Val Trp Val Lys Pro Leu Phe Met Asn Val Pro Leu Pro
         35                  40                  45

Asn Phe Lys Glu Leu Gln Glu Phe
     50                  55

<210> SEQ ID NO 215
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 215

Lys Ala Lys Glu Gln His Val Leu Trp Glu Asn Ala Gly Pro Thr Met
  1               5                  10                  15

Tyr Tyr Leu Thr Leu Glu Ala Lys Asp Gly Gly Lys Lys Lys Leu Tyr
             20                  25                  30

Glu Ala Lys Val Trp Val Lys His Thr Arg Tyr Glu Tyr Phe Val Tyr
         35                  40                  45

Asn Phe Lys Glu Leu Gln Glu Phe
     50                  55

<210> SEQ ID NO 216
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 216

Lys Ala Lys Glu Gln Arg Lys Leu Trp Glu Asn Tyr Lys Glu Thr Met
  1               5                  10                  15

Tyr Tyr Leu Thr Leu Glu Ala Lys Asp Gly Gly Lys Lys Lys Leu Tyr
             20                  25                  30
```

Glu Ala Lys Val Trp Val Lys Ala Met Arg Met Tyr Tyr Pro Glu Trp
            35                  40                  45

Asn Phe Lys Glu Leu Gln Glu Phe
    50                  55

<210> SEQ ID NO 217
<211> LENGTH: 56
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 217

Lys Ala Lys Glu Gln Gln Trp Ser Trp Gln Asn Ala Val Asp Thr Met
1               5                   10                  15

Tyr Tyr Leu Thr Leu Glu Ala Lys Asp Gly Gly Lys Lys Lys Leu Tyr
            20                  25                  30

Glu Ala Lys Val Trp Val Lys Val Arg Pro Arg Gly Leu Phe Trp Asp
            35                  40                  45

Asn Phe Lys Glu Leu Gln Glu Phe
    50                  55

<210> SEQ ID NO 218
<211> LENGTH: 42
<212> TYPE: PRT
<213> ORGANISM: Artificial Sequence
<220> FEATURE:
<223> OTHER INFORMATION: LOOP1 and LOOP2 region of Adherin that binds to
      Growth factor receptor bound protein 2 (Grb2) Src homology 2
      domain

<400> SEQUENCE: 218

Lys Ala Lys Glu Gln Trp Tyr Asn Pro Thr Met Tyr Tyr Leu Thr Leu
1               5                   10                  15

Glu Ala Lys Asp Gly Gly Lys Lys Lys Leu Tyr Glu Ala Lys Val Trp
            20                  25                  30

Val Lys Asn Phe Lys Glu Leu Gln Glu Phe
            35                  40

<210> SEQ ID NO 219
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 219

Ala Lys Glu Gln Thr Asp Glu Phe Asn Gln Pro Trp Asn Thr Met Tyr
1               5                   10                  15

Tyr Leu Thr Leu Glu Ala Lys Asp Gly Gly Lys Lys Lys Leu Tyr Glu
            20                  25                  30

Ala Lys Val Trp Val Lys Thr Ile Tyr Ile Asn Ser Phe Ile Met Asn
            35                  40                  45

Phe Lys Glu
    50

<210> SEQ ID NO 220
<211> LENGTH: 51
<212> TYPE: PRT

```
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 220

Ala Lys Glu Gln Thr Asp Gln Gln Lys Pro Trp Asn Thr Met Tyr
1               5                   10                  15

Tyr Leu Thr Leu Glu Ala Lys Asp Gly Gly Lys Lys Lys Leu Tyr Glu
            20                  25                  30

Ala Lys Val Trp Val Lys Lys Leu Phe Val Asn Arg Asn Pro Trp Asn
        35                  40                  45

Phe Lys Glu
    50

<210> SEQ ID NO 221
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 221

Ala Lys Glu Gln Val Met Glu Val Pro Tyr Phe Trp Gln Thr Met Tyr
1               5                   10                  15

Tyr Leu Thr Leu Glu Ala Lys Asp Gly Gly Lys Lys Lys Leu Tyr Glu
            20                  25                  30

Ala Lys Val Trp Val Lys Trp Ile Leu Val Ala Asn Glu Gln Ala Asn
        35                  40                  45

Phe Lys Glu
    50

<210> SEQ ID NO 222
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 222

Ala Lys Glu Gln Asn Asp Gln Asp His Tyr Ile His Glu Thr Met Tyr
1               5                   10                  15

Tyr Leu Thr Leu Glu Ala Lys Asp Gly Gly Lys Lys Lys Leu Tyr Glu
            20                  25                  30

Ala Lys Val Trp Val Lys Leu Leu Ile Leu Thr Asn Ile Ser Phe Asn
        35                  40                  45

Phe Lys Glu
    50

<210> SEQ ID NO 223
<211> LENGTH: 50
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 223
```

-continued

Ala Lys Glu Gln Pro Val Pro Ile Lys Ala Trp Glu Thr Met Tyr Tyr
1               5                   10                  15

Leu Thr Leu Glu Ala Lys Asp Gly Gly Lys Lys Leu Tyr Glu Ala
            20                  25                  30

Lys Val Trp Val Lys Lys Ile Ile Tyr Asn Asn Lys Ile Asn Phe
        35                  40                  45

Lys Glu
    50

<210> SEQ ID NO 224
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 224

Ala Lys Glu Gln Ser Lys Gln Val Asn Trp Lys Ala His Thr Met Tyr
1               5                   10                  15

Tyr Leu Thr Leu Glu Ala Lys Asp Gly Gly Lys Lys Leu Tyr Glu
            20                  25                  30

Ala Lys Val Trp Val Lys Ser Ile Leu Met Ala His Glu Thr Phe Asn
        35                  40                  45

Phe Lys Glu
    50

<210> SEQ ID NO 225
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 225

Ala Lys Glu Gln Ser Lys Asp Pro Trp Thr Arg Leu Gly Thr Met Tyr
1               5                   10                  15

Tyr Leu Thr Leu Glu Ala Lys Asp Gly Gly Lys Lys Leu Tyr Glu
            20                  25                  30

Ala Lys Val Trp Val Lys Glu Asp Pro Trp Ile Trp Phe Leu Ala Asn
        35                  40                  45

Phe Lys Glu
    50

<210> SEQ ID NO 226
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 226

Ala Lys Glu Gln Trp Leu Arg Ile Tyr Gln Asp Trp Phe Thr Met Tyr
1               5                   10                  15

Tyr Leu Thr Leu Glu Ala Lys Asp Gly Gly Lys Lys Leu Tyr Glu
            20                  25                  30

Ala Lys Val Trp Val Lys Asp Thr Lys Ser Pro Asp Tyr Gly Val Asn
            35                  40                  45

Phe Lys Glu
    50

<210> SEQ ID NO 227
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 227

Ala Lys Glu Gln Met Thr Lys Pro Lys Pro Gly His Ser Thr Met Tyr
1               5                   10                  15

Tyr Leu Thr Leu Glu Ala Lys Asp Gly Gly Lys Lys Lys Leu Tyr Glu
            20                  25                  30

Ala Lys Val Trp Val Lys Pro Glu Ala Asp Ile Ala Phe Leu Trp Asn
            35                  40                  45

Phe Lys Glu
    50

<210> SEQ ID NO 228
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 228

Ala Lys Glu Gln Ile Ile Glu Val Ala Ser Pro Trp Asn Thr Met Tyr
1               5                   10                  15

Tyr Leu Thr Leu Glu Ala Lys Asp Gly Gly Lys Lys Lys Leu Tyr Glu
            20                  25                  30

Ala Lys Val Trp Val Lys Lys Ile Arg Trp Asp Gly Asp Trp Tyr Asn
            35                  40                  45

Phe Lys Glu
    50

<210> SEQ ID NO 229
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 229

Ala Lys Glu Gln Ser Glu Gly His Thr Phe Ile Gln Glu Thr Met Tyr
1               5                   10                  15

Tyr Leu Thr Leu Glu Ala Lys Asp Gly Gly Lys Lys Lys Leu Tyr Glu
            20                  25                  30

Ala Lys Val Trp Val Lys Ser Leu Met Leu Thr Ser Gly Ala Phe Asn
            35                  40                  45

Phe Lys Glu
    50

```
<210> SEQ ID NO 230
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 230

Ala Lys Glu Gln Thr Leu Val Thr Glu Asp Pro Gln Tyr Thr Met Tyr
1               5                   10                  15

Tyr Leu Thr Leu Glu Ala Lys Asp Gly Gly Lys Lys Lys Leu Tyr Glu
            20                  25                  30

Ala Lys Val Trp Val Lys Trp Asp Met Ser Ile Met Phe Met Trp Asn
        35                  40                  45

Phe Lys Glu
    50

<210> SEQ ID NO 231
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 231

Ala Lys Glu Gln Trp Leu Met Pro Met Ser Pro Trp Ser Thr Met Tyr
1               5                   10                  15

Tyr Leu Thr Leu Glu Ala Lys Asp Gly Gly Lys Lys Lys Leu Tyr Glu
            20                  25                  30

Ala Lys Val Trp Val Lys Ser Ile Thr Tyr Arg Lys Gln Asp Val Asn
        35                  40                  45

Phe Lys Glu
    50

<210> SEQ ID NO 232
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 232

Ala Lys Glu Gln Glu Pro His Met Gly Ile Pro Trp Met Thr Met Tyr
1               5                   10                  15

Tyr Leu Thr Leu Glu Ala Lys Asp Gly Gly Lys Lys Lys Leu Tyr Glu
            20                  25                  30

Ala Lys Val Trp Val Lys Glu Ile Tyr Met Glu Thr His Ile Val Asn
        35                  40                  45

Phe Lys Glu
    50

<210> SEQ ID NO 233
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
``` homology domain 2

<400> SEQUENCE: 233

```
Ala Lys Glu Gln Trp Pro Phe Asn Thr Gln Thr Trp Asn Thr Met Tyr
1               5                   10                  15

Tyr Leu Thr Leu Glu Ala Lys Asp Gly Gly Lys Lys Leu Tyr Glu
            20                  25                  30

Ala Lys Val Trp Val Lys Tyr Phe Lys Phe Tyr Gly Asn Asn Met Asn
        35                  40                  45

Phe Lys Glu
    50
```

<210> SEQ ID NO 234
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 234

```
Ala Lys Glu Gln Phe Pro Leu Asp Ala Met Pro Trp Val Thr Met Tyr
1               5                   10                  15

Tyr Leu Thr Leu Glu Ala Lys Asp Gly Gly Lys Lys Leu Tyr Glu
            20                  25                  30

Ala Lys Val Trp Val Lys Ser Ile Lys Val His His Asp Thr Ile Asn
        35                  40                  45

Phe Lys Glu
    50
```

<210> SEQ ID NO 235
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 235

```
Ala Lys Glu Gln Trp Pro Trp Gln Asp Val Val Phe Ser Thr Met Tyr
1               5                   10                  15

Tyr Leu Thr Leu Glu Ala Lys Asp Gly Gly Lys Lys Leu Tyr Glu
            20                  25                  30

Ala Lys Val Trp Val Lys Gln Leu Ala Ile Asp Gly Val Trp Met Asn
        35                  40                  45

Phe Lys Glu
    50
```

<210> SEQ ID NO 236
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 236

```
Ala Lys Glu Gln Pro Glu Ser Arg Thr Gln Ala Trp Gln Thr Met Tyr
1               5                   10                  15
```

```
Tyr Leu Thr Leu Glu Ala Lys Asp Gly Gly Lys Lys Leu Tyr Glu
            20                  25                  30

Ala Lys Val Trp Val Lys Glu Ile Arg Ile Lys Met His Trp Tyr Asn
        35                  40                  45

Phe Lys Glu
    50

<210> SEQ ID NO 237
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 237

Ala Lys Glu Gln Leu Val His Asp Asp Val Pro Trp Gln Thr Met Tyr
1               5                   10                  15

Tyr Leu Thr Leu Glu Ala Lys Asp Gly Gly Lys Lys Leu Tyr Glu
            20                  25                  30

Ala Lys Val Trp Val Lys Ala Leu Asn Tyr Asn Gly Met Trp Asp Asn
        35                  40                  45

Phe Lys Glu
    50

<210> SEQ ID NO 238
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 238

Ala Lys Glu Gln Trp Val Leu Phe Ile Pro Tyr Arg Met Thr Met Tyr
1               5                   10                  15

Tyr Leu Thr Leu Glu Ala Lys Asp Gly Gly Lys Lys Leu Tyr Glu
            20                  25                  30

Ala Lys Val Trp Val Lys His Gln Gly Ile Glu Asn Asn Asn Gly Asn
        35                  40                  45

Phe Lys Glu
    50

<210> SEQ ID NO 239
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 239

Ala Lys Glu Gln Leu His Glu Ser Val Thr Phe Glu Pro Thr Met Tyr
1               5                   10                  15

Tyr Leu Thr Leu Glu Ala Lys Asp Gly Gly Lys Lys Leu Tyr Glu
            20                  25                  30

Ala Lys Val Trp Val Lys Gln Phe Trp Ile Asn His Ala Trp Asp Asn
        35                  40                  45

Phe Lys Glu
```

```
50

<210> SEQ ID NO 240
<211> LENGTH: 51
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 240

Ala Lys Glu Gln Ser His Ala Ser Ser Arg Pro Trp Ala Thr Met Tyr
1               5                   10                  15

Tyr Leu Thr Leu Glu Ala Lys Asp Gly Gly Lys Lys Lys Leu Tyr Glu
                20                  25                  30

Ala Lys Val Trp Val Lys Ala Ile Ile Ala His Gly Phe Pro Ala Asn
            35                  40                  45

Phe Lys Glu
    50

<210> SEQ ID NO 241
<211> LENGTH: 34
<212> TYPE: PRT
<213> ORGANISM: Artificial Sequence
<220> FEATURE:
<223> OTHER INFORMATION: LOOP1 and LOOP2 region of Adherin that binds to
      Signal Transducer and Activator of Transcription 3 (STAT3) Src
      homology domain 2

<400> SEQUENCE: 241

Ala Lys Glu Gln Trp Thr Met Tyr Tyr Leu Thr Leu Glu Ala Lys Asp
1               5                   10                  15

Gly Gly Lys Lys Lys Leu Tyr Glu Ala Lys Val Trp Val Lys Asn Phe
                20                  25                  30

Lys Glu
```

SCAFFOLD PROTEINS DERIVED FROM PLANT CYSTATINS

STATEMENT OF PRIORITY

This application is a 35 USC § 371 national phase application of International Application Serial No. PCT/GB2014/050435, filed Feb. 14, 2014, which claims priority to British Application No. 1302597.8, filed Feb. 14, 2013, the entire contents of each of which are incorporated by reference herein. The above-referenced PCT International Application was published as International Publication No. WO 2014/125290 A1 on Aug. 21, 2014.

STATEMENT REGARDING ELECTRONIC FILING OF A SEQUENCE LISTING

A Sequence Listing in ASCII text format, submitted under 37 C.F.R. § 1.821, entitled 9052-335TS Revised ST25.TXT, 126,466 bytes in size, generated on Oct. 13, 2017, and filed via EFS-Web, is provided in lieu of a paper copy. This Sequence Listing is hereby incorporated by reference into the specification for its disclosures.

The present invention relates to novel proteins, nucleic acids encoding them, and to methods of using them. In particular, the present invention relates to proteins with utility as scaffolds for displaying peptide sequences, and to use of these scaffolds in areas such as therapy, diagnosis, environmental and security monitoring, synthetic biology and research.

BACKGROUND OF THE INVENTION

The use of 'so-called' protein scaffolds is gaining attention in biochemistry as a potential route to generating novel ligand binding proteins for use in research and medicine. Such scaffold proteins, used to display one or more peptide sequences, can potentially provide an alternative to antibodies or antibody fragments.

The term 'protein scaffold' is used to describe a type of polypeptide structure that is observed in differing contexts and with distinct biochemical functions. Because of their intrinsic conformational stability it has been reasoned that such scaffolds might be amenable to protein engineering.

It is conventionally thought that immunoglobulins (antibodies) owe their function to the composition of a conserved framework region and a spatially well-defined antigen-binding site made of hypervariable peptide segments, these segments are variable both in sequence and in conformation. After antibody engineering methods along with library techniques resulted in successes in the selection of functional antibody fragments, interest began to grow in using other protein architectures to synthesise useful binding proteins.

Descriptions of the desirable properties of a suitable protein scaffold taken include the following;

"Candidates for suitable protein scaffolds ought to exhibit a compact and structurally rigid core that is able to present surface loops of varying sequence and length or to otherwise tolerate side chain replacements in a contiguous surface region, including exposed hydrophobic residues, without significant changes in their folding properties." Skerra A: Engineered protein scaffolds for molecular recognition. J Mol Recognit 2000, 13:167-187 and The term 'scaffold', as used in protein engineering, describes a single chain polypeptidic framework typically of reduced size (<200 AA) and containing a highly structured core associated with variable portions of high conformational tolerance allowing insertions, deletions, or other substitutions'. Wurch et al., Trends in Biotechnology, November 2012, 30, 575-582.

However, not all kinds of polypeptide fold which may appear attractive for the engineering of loop regions at a first glance will indeed permit the construction of independent ligand binding sites with high affinities and specificities.

Prior art scaffolds include inactivated staphylococcal nuclease, green fluorescent protein (GFP) and thioredoxin A (TrxA), the fibronectin type III domain ('Fn3'), lipocalin family proteins, bilin binding protein (BBP), as well as isolated protein folds such as the Z domain of staphylococcal protein A, "affibodies", anticafins, and ankyrin repeats, and others.

WO 2006/131749 describes several rational mutations made in Stefin A to improve it as a scaffold. The modified Stefin A scaffold comprises mutations at the following three sites Lys71-Leu73, V48D and G4W and is referred to as STM (Stefin A Triple Mutant).

WO2009/136182 describes further refinements of STM scaffolds.

There remains a need for improved scaffold proteins. In particular, it has been found that prior art scaffolds are often unable to sufficiently stabilise peptide aptamers, and the presence of the aptamers in the scaffold actually causes the scaffold to significantly deform. See for example Woodman et al., 'Design and Validation of a Neutral Protein Scaffold for the Presentation of Peptide Aptamers', J. Mol. Biol. (2005) 352, 1118-1133

Ideally such improved scaffold proteins would provide one or more of the following benefits:
Improved stability to provide a rigid framework that does not deform;
Smaller size;
Improved ability to support high quality and complexity libraries;
Improved affinity of selected binding proteins for their target; and
Simplicity of further manipulation due to accessible N- and C-terminal ends.

STATEMENTS OF THE INVENTION

According to the present invention there is provided a synthetic protein having a sequence derived from or related to a plant cystatin.

Suitably the synthetic protein comprises a consensus sequence of several (e.g. 10 or more, 20 or more, or 50 or more) plant cystatin proteins.

Suitably the synthetic protein is a scaffold protein comprising sites adapted or suitable for insertion of heterologous peptide sequences.

The scaffold protein of the present invention is thus preferably not based on a single naturally occurring protein sequence, but is a novel protein that does not exist in nature, being derived through careful design of consensus sequence from representatives of the class of plant cystatins.

In one embodiment the synthetic protein comprises the amino acid sequence (SEQ ID NO 1)
NSLEIEELARFAVDEHNKKENALLEFVRVVKAKEQVVAGTMYYLTLEAK

DGGKKKLYEAKVWVKPWENFKELQEFKPVGDA, or a variant thereof. Preferably the variant has a sequence at least 50%, more preferably 70%, identical thereto.

It has been found that a synthetic protein comprising such a sequence provides a highly stable and useful scaffold protein.

In another embodiment the synthetic protein comprises the amino acid sequence (SEQ ID NO 2)
GNENSLEIEELARFAVDEHNKKENALLEFVRVVKAKEQVVAGTMYYLTL

EAKDGGKKKLYEAKVWVKPWENFKELQEFKPVGDA, or a variant thereof. Preferably the variant has a sequence at least 50%, more preferably 70%, identical thereto.

In another embodiment the synthetic protein comprises the amino acid sequence (SEQ ID NO 3)
ATGVRAVPGNENSLEIEELARFAVDEHNKKENALLEFVRVVKAKEQ

VVAGTMYYLTLEAKDGGKKKLYEAKVWVKPWENFKELQEFKPVGDA, or a variant thereof. Preferably the variant has a sequence at least 50%, more preferably 70%, identical thereto.

More preferably the synthetic protein of the present invention comprises an amino acid sequence which is at least 75%, 80%, 85%, 90%, 95% or 99% identical to SEQ ID NOS 1, 2 or 3 above. Generally higher levels of identity are preferred.

In some cases the synthetic protein comprises or consists of an amino acid sequence which is identical, or substantially identical, to SEQ ID NO 1, 2 or 3.

In preferred embodiments of the present invention the synthetic protein set out above comprises at least one heterologous peptide sequence inserted therein. The synthetic proteins of the present invention have particular utility as scaffold proteins used to constrain and display peptide sequences. The present invention thus extends to both the 'empty' scaffold protein (i.e. without any heterologous peptide sequences present) and the scaffold protein with one or more heterologous sequences inserted therein.

Accordingly, a preferred embodiment of the present invention is a synthetic scaffold protein having a sequence as described herein, the scaffold protein displaying one or more heterologous peptides inserted at appropriate points in the scaffold. By 'displaying' it is meant that the peptide sequence is inserted into the scaffold protein at a location which allows the peptide to be exposed on the surface of the scaffold under suitable conditions, e.g. non-denaturing conditions, such as in vivo or in an in vitro assay. Such scaffold proteins displaying one or more heterologous peptides are often referred to as peptide aptamers or multiple peptide aptamers, though it should be noted that the term aptamers is used somewhat inconsistently in the art to refer to the peptides themselves or the complete protein.

Preferably the heterologous peptide sequence is from 3 to 30 amino acids in length, more preferably from 4 to 20 amino acids, more preferably from 4 to 16 amino acids. The synthetic proteins of the present invention have been found to be particularly suitable for displaying heterologous sequences from 5 to 13 amino acids in length.

Preferably the heterologous peptide sequence is inserted in a loop region of the synthetic protein or at the N-terminus of the protein. Loop regions can be defined as regions which are not involved with ordered secondary or tertiary structures of the protein when under conventional conditions (i.e. the protein is correctly folded and not under denaturing conditions), but may contribute to function and/or the correct spatial organisation of secondary structure elements in the protein. The position of loop regions within the scaffold protein can of course vary between different protein variants. Loop regions of the synthetic protein can be determined by examining the secondary and tertiary structure of the protein, and methods to achieve this are well known in the art, including X-ray crystallography, NMR, and also in silico methods.

In the present invention it is preferred that the heterologous peptides are inserted in at least one of the following positions in the protein:
  the loop between a first and second region of β-sheet (known as LOOP1); and
  the loop between a third and fourth region of β-sheet (known as LOOP2).

First, second, third and fourth is, of course, intended to be interpreted as relative to the protein sequence, i.e. from the N- to C-terminus of the protein.

Preferably heterologous peptides are inserted at both of these positions, i.e. at LOOP1 and LOOP2.

It is preferred that the loop length between adjacent regions of beta sheet is from 3 to 20 amino acids in length, more preferably from 5 to 13 amino acids in length, and it is believed that a loop length of approximately 9 amino acids in length is optimal.

Exemplary pairs of heterologous peptides for insertion into LOOP1 and LOOP2 are set out in Table 2, i.e. SEQ ID NOS 25 to 72. These examples form preferred embodiments of the present invention.

In addition, a further insertion point for a heterologous peptide is at or near (e.g. within 4 amino acids) the N-terminus of the protein. The peptide sequence at this point is believed to be less critical to binding a target than insertions at the other two positions mentioned above, but nonetheless it would appear to have a role in binding.

Thus in one embodiment of the present invention, the synthetic scaffold protein comprises three heterologous peptides, one in each of the locations discussed above.

In the case of the specific sequences set out above, preferred loop regions within the protein sequence are located as underlined:

(SEQ ID NO 1)
NSLEIEELARFAVDEHNKKENALLEFVRVVKAKEQ<u>VVAG</u>TMYYLTLEAKD

GGKKKLYEAKVWVK<u>PWE</u>NFKELQEFKPVGDA (SEQ ID NO 2)
GNENSLEIEELARFAVDEHNKKENALLEFVRVVKAKEQ<u>VVAG</u>TMYYLTLE

AKDGGKKKLYEAKVWVK<u>PWE</u>NFKELQEFKPVGDA (SEQ ID NO 3)
M<u>AT</u>GVRAVPGNENSLEIEELARFAVDEHNKKENALLEFVRVVKAKEQ<u>VVA</u>

<u>G</u>TMYYLTLEAKDGGKKKLYEAKVWVK<u>PWE</u>NFKELQEFKPVGDA

The underlined regions could be completely or partially replaced by the heterologous peptide, or the heterologous peptide could be inserted within the underlined regions without removal of the loop regions. Additionally, a heterologous peptide can be added to the N terminus of SEQ ID NO 1 or 2.

However, it should be noted that the heterologous peptide could be inserted in other loop regions, for example the loop regions between α-helix and first β-sheet and/or the second and third region of β-sheet (which may be referred to as LOOP 3 and LOOP 4 respectively for convenience). When the scaffold protein is correctly folded, these loop regions are positioned at the opposite side of the scaffold from those mentioned above (LOOP 1 and LOOP 2). By inserting heterologous peptides loop regions on both sides of the scaffold it is possible to produce a divalent moiety, able to bind a first target on one side of the scaffold and a second target at the other (generally opposite) side, and this may be a desirable embodiment in certain situations.

Where the synthetic protein comprises an amino acid sequence as set out above, the sequence can be contiguous or non-contiguous. For example, the sequence will be non-contiguous where a heterologous peptide has been inserted within the synthetic protein, e.g. at one of the loop regions mentioned above, the heterologous peptide thus separating portions of the abovementioned sequences.

It will be noted that calculations of sequence identity should for the present invention, in general, be adapted so as to take account of the situation where a heterologous peptide is inserted into the synthetic protein. When such an insertion has occurred, the inserted peptide sequence should typically be disregarded when calculating sequence identity. This is because the synthetic proteins of the present invention function as scaffolds, in which case the inserted peptides are inserted at points in the synthetic protein where they will be displayed at the surface of the protein. The inserted peptide sequences are by their very nature and purpose highly variable. In such a case it is the sequence of the scaffold portion of the protein which is of concern, as it provides the stable framework for display of the peptides, rather than the intentionally highly variable inserted peptide sequences.

The heterologous peptide can be inserted into the synthetic protein with or without the removal of amino acids normally found in the synthetic protein. That is to say the heterologous peptide can be inserted at an end of the synthetic protein or between two amino acids within the synthetic protein, without any normal amino acids of the synthetic protein being removed. Alternatively, when a peptide is inserted into the synthetic protein one or more amino acids normally present in the synthetic scaffold protein can be removed/replaced. e.g. the 'loop' amino acids WAG (SEQ ID NO 82), PWE and ATG (when present) can be removed in sequences 1, 2 and 3 above, or the corresponding loop sequences in a sequence variant.

Particularly preferred scaffold proteins according to the invention are set out in SEQ ID NOS 74 to 79 below, and the associated description of potential modifications to the scaffolds.

The term "identity" in respect of protein sequence refers to a degree of similarity between proteins in view of differences in amino acids, but which takes into account different amino acids which are functionally similar in view of size, lipophilicity, acidity, etc. A percentage identity can be calculated by optimal alignment of the sequences using a similarity-scoring matrix such as the Blosum62 matrix described in Henikoff S. and Henikoff J. G., P.N.A.S. USA 1992, 89: 10915-10919. Calculation of the percentage identity and optimal alignment of two sequences using the Blosum62 similarity matrix and the algorithm of Needleman and Wunsch (J. Mol. Biol. 1970, 48: 443-453) can be performed using the GAP program of the Genetics Computer Group (GCG, Madison, Wis., USA) using the default parameters of the program. Specific parameters for calculating percentage identity for protein sequences and nucleic acid sequences in respect of the present invention are described below.

Variants of the proteins that also form part of the present invention may contain variations in the amino acid sequence due to deletions, substitutions, insertions, inversions or additions of one or more amino acids in said sequence or due to an alteration to a moiety chemically linked to the protein. For example, a protein variant may comprise a carbohydrate or PEG structure attached to a protein. The proteins of the invention may include one or more such protein modification. The proteins of the invention may include a deletion of 1 or more amino acids, e.g. 1, 2, 3, 4, 5, 6, 7, 8, 9 or 10, amino acids from the N or C terminus, provided the variant retains the desired function.

Substitutional variants of proteins are those in which at least one residue in the amino acid sequence has been removed and a different residue inserted in its place. The proteins of the present invention can contain conservative or non-conservative substitutions.

The term "conservative substitution", relates to the substitution of one or more amino acid substitutions for amino acid residues having similar biochemical properties. Typically, conservative substitutions have little or no impact on the activity of a resulting protein. For example, a conservative substitution in a protein may be an amino acid substitution that does not substantially affect the ability of the protein to fold correctly and otherwise perform its usual biological function. Screening of variants of the proteins of the present invention can be used to identify which amino acid residues can tolerate an amino acid substitution. In one example, the relevant melting temperature or the amount of α-helix and β-sheet of a modified protein is not reduced by more than 25%, preferably not more than 20%, especially not more than 10%, when one or more conservative amino acid substitutions are effected.

One or more conservative substitutions can be included in a protein of the present invention. In a preferred example, 10 or fewer conservative substitutions are included in the protein. A protein of the invention may therefore include 1, 2, 3, 4, 5, 6, 7, 8, 9, 10 or more conservative substitutions. A polypeptide can be produced which contain one or more conservative substitutions by manipulating the nucleotide sequence that encodes that polypeptide using, for example, standard procedures such as site-directed mutagenesis or PCR. Alternatively, a polypeptide can be produced to contain one or more conservative substitutions by using peptide synthesis methods as known in the art.

Examples of amino acids which may be substituted for an original amino acid in a protein and which are regarded as conservative substitutions include: Ser for Ala; Lys for Arg; Gln or His for Asn; Glu for Asp; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val. In one embodiment, the substitutions are among Ala, Val Leu and Ile; among Ser and Thr; among Asp and Glu; among Asn and Gln; among Lys and Arg; and/or among Phe and Tyr. Further information about conservative substitutions can be found in, among other locations, Ben-Bassat et al., (J. Bacteriol. 169:751-7, 1987), O'Regan et al., (Gene 77:237-51, 1989), Sahin-Toth et al., (Protein Sci. 3:240-7, 1994), Hochuli et al., (Bio/Technology 6:1321-5, 1988), WO 00/67796 (Curd et al.) and in standard textbooks of genetics and molecular biology.

Other variants can be, for example, functional variants such as salts, amides, esters, and specifically C-terminal esters, and N-acyl derivatives. Also included are peptides which are modified in vivo or in vitro, for example by glycosylation, amidation, carboxylation or phosphorylation.

Proteins according to the present invention can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable caution or esterified, for example to form a C1-C6 alkyl ester, or converted to an amide, for example of formula $CONR^1R^2$ wherein $R^1$ and $R^2$ are each independently H or C1-C6 alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to C1-C6 alkyl or dialkyl amino or further converted to an amide. Hydroxyl groups of the peptide side chains may be converted to alkoxy or ester groups, for example C1-C6 alkoxy or C1-C6 alkyl ester, using well-recognized techniques. Phenyl and phenolic rings of the peptide side chains may be substituted with one or more halogen atoms, such as F, Cl, Br or I, or with C1-C6 alkyl, C1-C6 alkoxy, carboxylic acids and esters thereof, or amides of such carboxylic acids. Methylene groups of the peptide side chains can be extended to homologous C2-C4 alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability.

In preferred embodiments of the present invention the synthetic protein has a melting temperature (Tm) of at least 90° C., more preferably at least 95° C., and most preferably at least 100° C. Tm in the case of proteins is also known as the denaturation midpoint, and is defined as the temperature at which both the folded and unfolded states are equally populated. Tm is generally determined for the synthetic protein in which no heterologous peptide sequences have been inserted. Insertion of heterologous sequences can, and often does, reduce the Tm and therefore the most meaningful value is obtained when empty scaffold proteins are compared, and this is the basis of the Tm figures mentioned above. It is a surprising advantage of the present invention that such highly stable proteins have been obtained. Melting temperature is a particularly useful indicator of protein stability. The relative proportions of folded and unfolded proteins can be determined by many techniques known to the skilled person, including differential scanning calorimetry, UV difference spectroscopy, fluorescence, circular dichroism (CD), and NMR (see Pace, C. Nick, and J. Martin Scholtz. "Measuring the conformational stability of a protein" 299-321).

The extremely high temperature stability of the synthetic proteins of the present invention is also an indicator of the very high structural stability of the proteins when at normal temperatures (e.g. around 25° C. in vitro and 37° C. in vivo). This means that the synthetic proteins of the present invention are very well suited to act as scaffolds for displaying heterologous peptides. Their structural stability means that such heterologous peptides will be displayed consistently and accurately, without disruption of the scaffold protein structure. Because the synthetic proteins of the present invention are so stable, it is an indication that they will perform better than known scaffolds which do not have the same level of stability.

It is surprising that such a small scaffold protein would have a thermal transition temperature of, for example, 101° C., based on the source of the parental protein sequences of land plants that were used as a basis for its design. The land plant parents commonly grow at ambient external temperatures and so only a few crops such as rice might be expected to grow in tropical temperatures whilst the majority grow in moderate to cold northern climates.

As mentioned above, addition of heterologous peptides can, and typically does, reduce the stability of the synthetic scaffold proteins of the present invention. However, it has been found that the stability of the scaffolds of the present invention remains higher than prior art scaffolds. Accordingly, in a preferred embodiment the synthetic scaffold proteins having at least one heterologous peptide inserted therein have a Tm of 60° C. or higher, more preferably 70° C. or higher, and especially 80° C. or higher. This indicates that the scaffold proteins having at least one heterologous peptide inserted therein are highly stable.

Preferably the synthetic protein of the present invention comprises a linker or tag. The linker or tag can be an amino acid linker or tag, or another type of linker or tag. The tag can be any tag which provides a desired functionality to the synthetic protein, e.g. one which allows easy isolation or purification of the protein. An exemplary tag is a polyhistidine tag (also known as a His-tag), and other well-known tags include Myc-tag, SBP tag, S-tag, calmodulin tag, etc.

In a further embodiment of the present invention there is provided a synthetic protein as set out above connected to a substrate or moiety. The moiety can be a label, carrier, protein or the like. The synthetic protein can be connected directly to the substrate or moiety, or it can be connected via a linker. The synthetic protein can be connected covalently or non-covalently to the substrate or moiety. Non-covalent systems for linking proteins to a substrate or moiety include, but are not restricted to, the biotin-avidin system.

Where the moiety is a label, it can be a fluorescent label, radioactive label, enzymatic label or any other label known to the skilled person.

Examples of fluorescent labels include, but are not restricted to, organic dyes (e.g. cyanine, fluorescein, rhodamine, Alexa Fluors, Dylight fluors, ATTO Dyes, BODIPY Dyes, etc.), biological fluorophores (e.g. green fluorescent protein (GFP), R-Phycoerythrin, etc.), and quantum dots.

Examples of enzymatic labels include, but are not restricted to, horseradish peroxidase (HRP), alkaline phosphatase (AP), glucose oxidase and β-galactosidase.

Another well-known label is biotin. Biotin labels are typically composed of the biotinyl group, a spacer arm and a reactive group that is responsible for attachment to target functional groups on proteins. Biotin can be useful for attaching the labelled protein to other moieties which comprise an avidin moiety.

Various strategies for labelling proteins are well known to the skilled person, and they could be readily applied to the synthetic proteins of the present invention.

The substrate to which the protein is bound can be any suitable surface, e.g. the surface of a container such as a 96 well plate.

Where the moiety is a carrier, it can, for example, be a bead (e.g. a magnetic bead) or other particle.

Typically labels, linkers or tags are added on the C- and/or N-termini of the protein. However can also be added via any region of the protein which is sufficiently spaced from the loops in which heterologous peptides are inserted so as not to interfere with target binding, most preferably on the opposite side from the loops with insertions.

In an embodiment of the present invention there is provided a fusion protein comprising a synthetic protein as set out above connected to a second protein. The second protein may be a protein having a desired activity. In certain embodiments of the invention the second protein may be a phage coat protein or another protein useful in a surface display system, and uses for such fusion proteins in scanning methods are described in more detail below. The second protein could of course be another synthetic protein, thus providing a homo- or hetero-multimeric scaffold protein.

In a further aspect of the present invention there is provided a library comprising a population of synthetic proteins, as described above, wherein various members of the population comprise a variety of heterologous peptides having different sequences. Suitable libraries of heterologous peptides can be created using combinatorial techniques known to the skilled person, and nucleic acid sequences encoding a suitable set of heterologous peptide sequences can be obtained through numerous commercial sources. Preferably such a library will have a complexity of $10^8$ or higher, more preferably $10^9$ or higher, and most preferably $10^{10}$ or higher.

Such a library has utility in selecting particular synthetic scaffold proteins which bind to a target entity. The target entity may be any entity to which it is desirable to have a protein bind specifically. Exemplary targets include, but are not limited to, proteins/peptides (e.g. receptors or ligands), small molecules (e.g. pharmaceutical molecules), nucleic acids (e.g. DNA or RNA) and inorganic compounds.

The library can comprise a population of the synthetic proteins of the present invention adapted for display in a suitable display system, e.g. a surface display system. The surface display system can suitably be a phage display. Alternatively, the surface display system can be a mRNA display, ribosome display, CIS-display or other non-covalent or covalent protein display system, bacterial display or yeast display. The yeast two-hybrid system or expression in bacterial or mammalian cell systems are commonly used in vivo systems for screening for aptamers which bind to target. Collectively these display systems are often referred to as biopanning systems.

For example, a phage display can be a filamentous phage (e.g. M13) display system. The synthetic protein can therefore be fused with pIII, pVIII, pVI, pVII or pIX proteins. Other phage display systems which can be used in the present invention include T4, T7 and λ phage display. It should be noted that the synthetic proteins of the present invention are versatile and can be used with any suitable display system, and various suitable systems are well known to the skilled person. Phage display is commonly used in the selection of antibodies, but the techniques are directly applicable to the proteins of the present invention. Summaries of phage display technologies can be found in, for example, Lowman H. B., Clackson T. (2004) Phage display: a practical approach. Oxford University Press. pp. 10-11.

In a particularly preferred embodiment of the present invention the synthetic protein of the present invention, especially when used in construction of a library, comprises the sequence:

(SEQ ID NO 4)
NSLEIEELARFAVDEHNKKENALLEFVRVVKAKEQ(X$_n$)TMYYLTLEAKD

GGKKKLYEAKVWVK(X$_n$)NFKELQEFKPVGDA wherein X is any amino acid and n is the number of amino acids in the sequence, and
wherein n is preferably from 3 to 30, more preferably from 4 to 20, and yet more preferably from 4 to 15.

Preferably the synthetic protein comprises the sequence:

(SEQ ID NO 5)
NSLEIEELARFAVDEHNKKENALLEFVRVVKAKEQ(X$_{5-13}$)TMYYLTLEA

KDGGKKKLYEAKVWVK(X$_{5-13}$)NFKELQEFKPVGDA

More preferably the synthetic protein comprises the sequence:

(SEQ ID NO 6)
NSLEIEELARFAVDEHNKKENALLEFVRVVKAKEQ(X$_9$)TMYYLTLEA

KDGGKKKLYEAKVVVVK(X$_9$)NFKELQEFKPVGDA

As discussed above, proteins comprising a sequence which is 50%, more preferably 70%, identical to SEQ ID NO 4, 5 or 6 are within the scope of the invention. More preferably the synthetic protein of the present invention comprises an amino acid sequence which is at least 75%, 80%, 85%, 90%, 95% or 99% identical to SEQ ID NO 4, 5 or 6. Generally higher levels of identity are preferred.

In any of the above examples, the protein may contain an additional amino acid sequence at the N-terminus. This can comprise some or all of the sequence MATGVRAVPGNE (SEQ ID NO 80). Alternatively or additionally it can comprise a further heterologous peptide sequence, e.g. of from 3 to 20 amino acids in length.

In embodiments of the present invention it may be preferred that the N terminal amino acid is a methionine. This can be achieved, for example, by adding on an additional methionine or by replacing the normal N-terminal amino acid with a methionine.

Particularly preferred scaffold proteins of the present invention are set out in SEQ ID NOS 74 to 79. Variants of these proteins according to the criteria set out above are also embodiments of the present invention.

In another aspect the present invention provides a polynucleotide which encodes a synthetic protein according to the present invention. The polynucleotide may be DNA or RNA. If the polynucleotide is DNA, it may be in single stranded or double stranded form. The single strand might be the coding strand or the non-coding (anti-sense) strand.

A polynucleotide according to the present invention may comprise a sequence encoding a protein having a sequence according to SEQ ID NO 1, 2, 3, 4, 5 or 6, or any one of SEQ ID NO 74 to 79, or a variant thereof, as discussed above.

In one embodiment the polynucleotide comprises the sequence:

(SEQ ID NO 7)
aacgctctgctggaattcgttcgtgttgttaaagctaaagaacaggttgt tgctggtaccatgtactacctgacctggaagctaaagacggtggtaaaa agaaactgtacgaagctaaagtttgggttaaaccgtgggaaaacttcaaa gaactgcaggagttcaaaccggttggtgacgct, which encodes the amino acid set out in SEQ ID NO 1.

In another embodiment the polynucleotide comprises the sequence:

(SEQ ID NO 8)
ggtaacgaaaactccctggaaatcgaagaactggctcgtttcgctgttga cgaacacaacaaaaaagaaaacgctctgctggaattcgttcgtgttgtta -continued

```
aagctaaagaacaggttgttgctggtaccatgtactacctgaccctggaa gctaaagacggtggtaaaaagaaactgtacgaagctaaagtttgggttaa accgtgggaaaacttcaaagaactgcaggagttcaaaccggttggtgacg ct, which encodes the amino acid set out in
SEQ ID NO 2.
```

In another embodiment the polynucleotide comprises the sequence:

```
                                            (SEQ ID NO 9)
gctaccggtgttcgtgcagttccgggtaacgaaaactccctggaaatcga agaactggctcgtttcgctgttgacgaacacaacaaaaaagaaaacgctc tgctggaattcgttcgtgttgttaaagctaaagaacaggttgttgctggt accatgtactacctgaccctggaagctaaagacggtggtaaaaagaaact gtacgaagctaaagtttgggttaaaccgtgggaaaacttcaaagaactgc aggagttcaaaccggttggtgacgct, which encodes the
amino acid set out in SEQ ID NO 3.
```

Polynucleotides that have a nucleic acid sequence that is a variant of the identified nucleic acid sequences may be isolated by a method comprising the steps of: a) hybridizing a DNA comprising all or part of the identified sequence as reflected in any one of SEQ ID NOs 7, 8 or 9, under stringent conditions against nucleic acids of interest; and b) isolating said nucleic acids by methods known to a person skilled in the art. The hybridization conditions are preferably highly stringent.

According to the present invention the term 'stringent' means washing conditions of 1×SSC, 0.1% SDS at a temperature of 65° C.; 'highly stringent' conditions refer to a reduction in SSC towards 0.3×SSC, more preferably to 0.1×SSC. Preferably the first two washings are subsequently carried out twice each during 15-30 minutes. If there is a need to wash under highly stringent conditions an additional wash with 0.1×SSC is performed once during 15 minutes. Hybridization can be performed overnight in 0.5 M phosphate buffer pH 7.5 with 7% SDS at 65° C. Such hybridization methods are disclosed in any standard textbook on molecular cloning, for example: Molecular Cloning: a laboratory manual, 3rd ed.; editors: Sambrook et al., CSHL press, 2001.

Variants of the sequences depicted in SEQ ID NOs 7, 8 or 9 may also be identified by comparing the sequence in silico to other sequences that may be comprised in a computer database. Sequences may be compared with sequences in databases using a BLAST program (BLASTF 2.1. 2 [Oct. 19, 2000]) (Altschul, S F, T L Madden, A A Schaffer, J Zhang, Z Zhang, W Miller, and D J Lipman, "Gapped BLAST and PSI-BLAST: a new generation of protein database search programs", Nucleic Acids Res. 1997, 25: 3389-3402).

Preferred embodiments of the invention are polynucleotides encoding proteins having at least 50%, more preferably 70%, more preferably 80%, more preferably 95% identity with SEQ ID NOS 1-6, and yet more preferred are those polynucleotides encoding proteins having at least 97% identity with SEQ ID NOS 1, 2, 3, 4, 5 or 6, or any one of SEQ ID NO 74 to 79, with those encoding proteins having at least 98 or 99% identity being more preferred. Most preferred are polynucleotides encoding the protein of SEQ ID NO 1, 2, 3, 4, 5 or 6, or any one of SEQ ID NO 74 to 79.

Due to the degeneracy of the genetic code, polynucleotides encoding an identical or substantially identical amino acid sequence may utilize different specific codons. All polynucleotides encoding the proteins as defined above are considered to be part of the invention.

In this regard it should be noted that the sequences discussed above have been optimised for expression in the bacterial host *Escherichia coli*, as this is a convenient system and is typically used for the techniques such as phage display and for subsequent production of selected binding proteins. However, anyone skilled in the art could choose to express the proteins in an alternative hosts system, and in that case a change in the nucleotide sequence that encodes the selected protein (i.e. codon optimisation) may be beneficial, and are thus part of the present invention. Optimising codon use for any particular host is routine for the skilled person.

In particular preferred embodiments the polynucleotides according to the invention are isolated polynucleotides comprising a sequence having at least 80% identity to the nucleic acid sequence of SEQ ID NOs 7, 8, or 9 (excluding sequences encoding heterologous peptides, where relevant).

Polynucleotides according to the present invention can, of course, contain additional sequences, such as sequences encoding heterologous peptides, expression control sequences or sequences encoding other proteins or protein subunits.

More preferred are those polynucleotides comprising a sequence having at least 90% identity, and yet more preferred at least 95% identity, preferably 99% identity, most preferred 100% identity to the entire sequence of SEQ ID NOs 7, 8 or 9 (excluding sequences encoding heterologous peptides, where relevant).

Also included within the definition of polynucleotides are modified RNAs or DNAs. Modifications in the bases of the nucleic acid may be made, and bases such as inosine may be incorporated. Other modifications may involve, for example, modifications of the backbone.

"% identity" defines the relation between two or more polynucleotides or polypeptides on the basis of a comparison between their aligned sequences.

Identity can be calculated by known methods. Identity, or homology, percentages as mentioned herein in respect of the present invention are those that can be calculated with the GAP program, running under GCG (Genetics Computer Group Inc., Madison, Wis., USA).

For polypeptide sequence comparison:
  Alignment algorithm: Needleman and Wunsch, J. Mol. Biol. 1970, 48: 443-453.
  As a comparison matrix for amino acid similarity the Blosum62 matrix is used (Henikoff and Henikoff, supra).
  The following gap scoring parameters are used:
    Gap penalty: 12
    Gap length penalty: 2
    No penalty for end gaps.
For nucleotide sequence comparison:
  Alignment algorithm: Needleman and Wunsch (supra).
  Comparison matrix:
    match=+10, mismatch=0.
    Gap penalty: 50.
    Gap length penalty: 3.
  Approaches to developing consensus stabilised proteins that include the incorporation of other parameters, such as phylogenetically unbiased methods as described by Jaeckel, Bloom et al. 2010, can also be used.

However, as discussed above, it will be noted that the various sequence identity calculations should be amended to take account of the situation where one or more heterologous peptides are optionally inserted into the synthetic protein. When such an insertion has occurred, the inserted sequence which encodes the peptide(s) should generally be disregarded when calculating sequence identity for the reasons set out above.

Nucleic acids, especially DNA, according to the invention will be useful for in vivo or in vitro expression of the encoded protein. When the polynucleotides according to the invention are used for expression of the encoded proteins, the polynucleotides may include, in addition to the coding sequence for the protein, other coding or non-coding sequences, for example, leader sequences or fusion portions, linker sequences, marker sequences, promoters, enhancers and the like.

The polynucleotides according to the invention may be used in the production of recombinant proteins according to the invention. This can be achieved through expression of the proteins in a suitable host cell or multicellular organism. When used for expression of an encoded polypeptide, the polynucleotides may advantageously include, in addition to the coding sequence for the polypeptide, other coding sequences, for example, signal sequences, leader sequences, targeting sequences, fusion portions, marker sequences, sequences to assist in purification and the like.

A wide variety of host cell and cloning vehicle combinations can be used for cloning and expression. Polynucleotides of the present invention may be cloned into any appropriate expression system. Suitable expression systems include bacterial expression system (e. g. *Escherichia coli* DH5α and BL21(DE3)), a viral expression system (e.g. Baculovirus), a yeast system (e.g. *Saccharomyces cerevisiae*) or eukaryotic cells (e.g. COS-7, CHO, BHK, HeLa, HD11, DT40, CEF, or HEK-293T cells). A wide range of suitable expression systems are available commercially. Typically the polynucleotide is cloned into an appropriate vector under control of a suitable constitutive or inducible promoter and then introduced into the host cell for expression.

In another aspect the present invention therefore provides a recombinant vector comprising a polynucleotide according to the invention. Suitable vectors include bacterial or yeast plasmids, cosmids, phagemids, fosmids, wide host range plasmids and vectors derived from combinations of plasmid and phage or virus DNA. An origin of replication and/or a dominant selection marker can suitably be present in the vector.

The vectors according to the invention are suitable for transforming a host cell. Examples of suitable cloning vectors are plasmid vectors such as pBR322, the various pUC, pET, pEMBL and Bluescript plasmids, or viral vectors such as retroviruses, lentiviruses, adenoviruses, adeno-associated viruses. pcDNA3.1 is a particularly preferred vector for expression in animal cells.

Particularly useful for the cloning and expression of the libraries of scaffold proteins are phage or phagemid vectors such as those derived from filamentous phage such as M13 or fd or caspid phage such as bacteriophage T7.

When used in the expression of the proteins of the present invention, a vector according to the present invention typically comprises an expression control sequence operably linked to the nucleic acid sequence coding for the protein to control expression of the relevant polynucleotide. Such expression control sequences generally comprise a promoter sequence and additional sequences which regulate transcription and translation and/or enhance expression levels. Suitable expression control sequences are well known in the art and include eukaryotic, prokaryotic, or viral promoter or poly-A signal. Expression control and other sequences will, of course, vary depending on the host cell selected or can be made inducible. Examples of useful promoters are the tac promoter (Deboer, Comstock et al. 1983), T7 promoter (Studier and Moffatt 1986), SV-40 promoter (Science 1983, 222: 524-527), the metallothionein promoter (Nature 1982, 296: 39-42), the heat shock promoter (Voellmy et al., P.N.A.S. USA 1985, 82: 4949-4953), the PRV gX promoter (Mettenleiter and Rauh, J. Virol. Methods 1990, 30: 55-66), the human CMV IE promoter (U.S. Pat. No. 5,168,062), the Rous Sarcoma virus LTR promoter (Gorman et al., P.N.A.S. USA 1982, 79: 6777-6781), or human elongation factor 1 alpha or ubiquitin promoter. Prokaryotic control sequences include, for example, lac, tac T7, ara, and other known promoters. Prokaryotic promoters in general which can be used in the present invention are discussed in Goldstein M A, Doi R H, 'Prokaryotic promoters in biotechnology'. Biotechnol Annu Rev. 1995; 1:105-28. Many other suitable control sequences are known in the art, and it would be routine for the skilled person to select suitable sequences for the expression system being used.

After the polynucleotide has been cloned into an appropriate vector, the construct may be transferred into the cell (e.g. bacterium or yeast) by means of an appropriate method, such as electroporation, $CaCl_2$ transfection or lipofectins. When a baculovirus expression system is used, the transfer vector containing the polynucleotide may be transfected together with a complete baculo genome.

These techniques are well known in the art and the manufacturers of molecular biological materials (such as Clontech, Agilent, Promega, and/or Invitrogen Life Technologies) provide suitable reagents and instructions on how to use them. Furthermore, there are a number of standard reference text books providing further information on this, e.g. Rodriguez, R. L. and D. T. Denhardt, ed., "Vectors: A survey of molecular cloning vectors and their uses", Butterworths, 1988; Current protocols in Molecular Biology, eds.: F. M. Ausubel et al., Wiley N. Y., 1995; Molecular Cloning: a laboratory manual, supra; and DNA Cloning, Vol. 1-4, 2nd edition 1995, eds.: Glover and Hames, Oxford University Press).

In a further aspect the present invention also provides a cell capable of expressing a recombinant protein, characterised in that the cell comprises a polynucleotide according to the invention encoding the recombinant protein to be expressed. Suitably the cell is a host cell transformed with a polynucleotide or vector as described above. The polynucleotide or vector according to the invention can be stably integrated into the genomic material of the cell or can be part of an autonomously replicating vector. "Recombinant" in this context refers to a protein that is not expressed in the cell in nature.

Host cells can be cultured in conventional nutrient media which can be modified, e.g. for appropriate selection, amplification or induction of transcription and thus expression of the recombinant protein. The host cells can be prokaryotic or eukaryotic. Mammalian, e.g. human, cell lines may be preferred, especially where the expressed proteins are intended for in vivo use in human or mammalian subjects. Suitable exemplary cell lines are mentioned above, and appropriate culture conditions for the various suitable cell types are well known to the person skilled in the art.

In a further aspect the present invention provides a cell culture comprising cells according to the invention.

In a further aspect the present invention provides a method of screening for a synthetic protein that binds to a target, the method comprising:
a) Providing a library comprising a population of synthetic scaffold proteins comprising one or more heterologous peptide sequences as described above;
b) Exposing said library to a target; and
c) Selecting synthetic scaffold proteins which bind to said target.

The target may suitably be a protein/peptide, a nucleic acid, or a small molecule or any other target of interest. The target can suitably be immobilised on a substrate, e.g. to the wells of a microtiter plate or on magnetic beads or other appropriate particles.

The method of screening may suitably be a display system, e.g. a surface display system. For example, a suitable surface display system could be a phage display, mRNA display, ribosome display, CIS (Odegrip, Coomber et al. 2004) or other non-covalent or covalent protein display (FitzGerald 2000), bacterial display (Lofblom 2011) and yeast display (Traxlmayr and Obinger 2012) or display on another eukaryotic cell (Makela and Oker-Blom 2008) I (Ho and Pastan 2009).

In certain embodiments of the present invention the proteins used in the screening method are thus fusions of the scaffold protein with a bacteriophage coat protein, so that the scaffold proteins are displayed on the surface of the viral particle. The protein displayed on the viral particle thus corresponds to the genetic sequence within the phage particle. Of course, where the surface display system is other than a phage display system the other suitable fusion proteins can be provided.

Where the target is immobilised on a substrate the surface displayed library is exposed to the substrate with the target immobilised thereon and, after a suitable period to allow the phage time to bind to the target, the substrate is rinsed. Proteins that bind to the target remain attached to the substrate, while others are washed away.

Suitably proteins which bind to the target are thereafter eluted or the associated phage cleaved from the target and, in the case of phage display, used to create more phage by infection of suitable bacterial hosts. This results in a new library which comprises an enriched mixture, containing considerably less irrelevant phage (i.e. phage which contains non-binding scaffold proteins) than were present in the initial library.

The steps of exposing the library to the target, rinsing, elution and infection are optionally repeated one or more times, further enriching the phage library in binding proteins. This is generally referred to as panning. Thus the method may involve performing multiple panning steps.

Once a desired number of panning steps have been performed the nucleic acid linked to the surface displayed protein can be sequenced to identify the scaffold proteins which bind to the target.

It has been found that scaffold proteins according to the present invention can be obtained which bind with high affinity and high specificity to targets. For example scaffold proteins which bind with an affinity of $1 \times 10^{-9}$ M have been obtained. Unexpectedly the libraries formed from scaffold proteins according to the present invention have revealed scaffold proteins that bind to proteins against which it has proved impossible to raise antibodies or antibodies with the desired specificity. For example, artificial binding proteins based on the scaffold have been selected proteins that specifically bind to Human Papilloma Virus (HPV) 16 E5, an understudied protein due to the repeated failure of ability to select lack of suitable antibodies against this target. HPV is a causative agent of cervical carcinoma. Artificial binding proteins have also been selected that discriminate between the two forms of the human Small Ubiquitin-like Modifier (SUMO), hSUMO1 and hSUMO2 whereas previously selected antibodies proved incapable of such discrimination. It is reasonable to expect that other useful binding proteins could be raised against other targets where antibody-based techniques have failed to provide a suitable solution.

In a further aspect the present invention provides a synthetic scaffold protein obtained by a screening method described above.

In a further aspect the present invention provides the use of synthetic protein as set out above, or a nucleic acid encoding such a synthetic protein, in research. For example, such proteins can be used in any area of research where antibodies or antibody fragments are typically used. Such methods may include interfering with protein/protein interactions, labelling targets (e.g. fluorescently), etc.

In a further aspect the present invention provides the use of synthetic protein as set out above, or a nucleic acid encoding such a synthetic protein, in environmental and security monitoring, or in synthetic biology.

In a further aspect the present invention provides the use of synthetic protein as set out above, or a nucleic acid encoding such a synthetic protein, in target detection.

In a further aspect the present invention provides the use of a synthetic scaffold protein as set out above, or a nucleic acid encoding such a synthetic protein, in therapy or diagnosis. For example, such proteins can be used in any area of diagnosis or therapy where antibodies or antibody fragments are typically used.

In a further aspect the present invention provides a pharmaceutical preparation comprising a synthetic protein as set out above and a pharmaceutically acceptable carrier or excipient.

In a further aspect the present invention provides a method for validating drug targets and identifying druggable domains on target proteins using synthetic protein as set out above.

In a further aspect the present invention provides a suitable method for selecting synthetic proteins that bind to small molecules including organic compounds and including drug compounds.

Suitably the synthetic proteins of the present invention can be linked to a suitable therapeutic agent. In such a situation the synthetic protein can provide a targeting function to deliver the therapeutic 'payload' to a desired target.

Preparation of pharmaceutical preparations according to the present invention is carried out by means conventional for the skilled person. Methods for preparing administrable compositions, whether for intravenous or subcutaneous administration or otherwise, will be known or apparent to those skilled in the art and are described in more detail in such publications as Remington: The Science and Practice of Pharmacy, Lippincott Williams and Wilkins; 21st Revised edition (1 May 2005).

'Synthetic protein' refers to a protein which is not found in nature and which has been formed through recombinant techniques.

The term 'protein' is generally used interchangeably with 'peptide' or 'polypeptide', and means at least two covalently attached amino acids linked by a peptidyl bond. The term protein encompasses purified natural products, or products which may be produced partially or wholly using recombinant or synthetic techniques. The term protein may refer to an aggregate of a protein, such as a dimer or other multimer, a fusion protein, a protein variant, or derivative thereof. The term also includes modified proteins, for example, a protein modified by glycosylation, acetylation, phosphorylation, pegylation, ubiquitination, and so forth.

A protein may comprise amino acids not encoded by a nucleic acid codon. Unnatural amino acids can be introduced by post-translational modification, for example through the introduction of a cysteine or other appropriate residue at a specific position and then the conversion of this following protein purification to a dehydroalanine and then chemical reaction with a suitably modified unnatural amino acid. Alternatively, an unnatural amino acid could be incorporated into the sequence during translation either in vitro or in vivo through the suppression of a stop codon, normally UAG via an appropriate heterologous tRNA/tRNA synthetase couple that charges a suppressing tRNA with an unnatural amino acid that can then be incorporated into the protein at the position of the UAG codon.

The protein of the present invention can be a single subunit protein or a multi-subunit protein wherein at least one subunit comprises the said sequence.

In certain embodiments the protein can comprise two or more synthetic proteins as set out above, e.g. in the form of a fusion protein. In such a case each of the synthetic proteins can bind to the same target or they can bind to different targets. Binding the same can be increase avidity and apparent binding affinity, whilst those binding distinct targets can be useful for the development of cross-linking or dual recognition modules.

'Heterologous peptide' or 'Heterologous peptide sequence' in the context of the present invention refers to a peptide sequence which is not normally found in the relevant location, e.g. in the loop region of the scaffold protein. Typically such peptides are relatively short, i.e. containing fewer than 30 amino acids, typically 20 or fewer. Such a peptide can have essentially any sequence. Indeed it is desirable that libraries containing a vast number of heterologous peptide sequences will be displayed in scaffold proteins.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are mentioned in this application, and which are open to public inspection, and the contents of all such papers and documents are incorporated herein by reference.

SPECIFIC EMBODIMENTS OF THE INVENTION

Embodiments of the invention will now be described, by way of example only, with reference to the accompanying drawings in which:

FIG. 1 shows a consensus phytocystatin PHYTC57 derived from 57 phytocystatin amino acid sequences (A) PHYTC57 synthetic gene shown as a double strand sequence together (SEQ ID NOS 91 and 92) with the overlapping oligonucleotides (P1 to P6, SEQ ID NOS 85-90, respectively) used to generate the gene by recursive PCR. The coding sequence is also shown as single letter amino acid code (SEQ ID NO 94). The positions of the two restriction sites SfiI and NotI are shown. (B) Schematic representation of the cloning region of pDHisII which is based on pHEN1. The positions of the relevant regions encoding the pelB signal sequence, hexhistidine tag and N-terminal section of the M13 phage PIII protein are shown. The positions of the standard M13 primer binding sites for M13R and P10 are indicated as are the unique SfiI and NotI restriction sites.

FIG. 2 shows graph of the results of papain inhibition assays for a modified oryzacystatin lacking residue Asp86 (OSA-IΔD86) and PHYTC57 at varying concentrations of phytocystatins, showing the enhanced efficacy of PHYTC57.

FIG. 3 shows surface plasmon resonance measurement of the interaction between cystatins immobilized on an NTA sensorchip, and papain. The experiments were performed at several concentrations of papain and data were analysed using the Biaevaluation3 software package (BIACORE) with global fitting of the data to the Langmuir 1:1 binding model. OSA-IΔD86, a modified rice cystatin I; CPA, *papaya* cystain; CUN, orange cystatin; CEWC, chicken egg white cystatin; PHYTC57, consensus cystatin.

FIG. 4 shows (A) Thermal stability of OSA-IΔD86 (grey square) and PHYTC57 (black triangle) shown as residual enzyme activity assayed at 25° C. following incubation at 100° C. for the times shown. PHYTC57 displays greater thermal stability than does OSA-IΔD86), B) Effect of simulated gastric fluid treatment on the inhibitory properties of OSA-IΔD86 (grey square) and PHYTC57 (black triangle) showing that PHYTC57 retains activity over a longer period of time than does OSA-IΔD86. (C) SDS-PAGE analysis of the stability of PHYTC57 and OSA-IΔD86 to incubation with simulated gastric fluid. The time of incubation is shown in seconds and the positions of marker proteins (M) are indicated on the left in kDa with the position of pepsin from the assay and the cystatin indicated. (D) Western blot analysis of PHYTC57 following simulated gastric fluid treatment for the times indicated (seconds) using an anti-His tag antibody. The positions of marker proteins (M) are indicated in kDa.

FIG. 5 PHYTC57 and OSA-IΔD86 comparison showing amino acid differences between the proteins PHYTC57 (SEQ ID NO 94) and OSA-IΔD86 (SEQ ID NO 93. (A) Alignment of protein sequences. (B) Representation of the position of the amino acid changes from (A) on the 3D structure of OSAI with residues changes labeled. The binding region is also shown with the N-terminal, QWAG (SEQ ID NO 83) and PW loops labeled.

FIG. 6 shows a crystal structure of an Adhiron isolated from the library and sequence of an Adhiron scaffold derived from PHYTC57. (A) The Adhiron scaffold is shown and the inserted loops are indicated. (B) Codon optimised nucleic acid sequence (SEQ ID NO 96) and amino acid sequence (SEQ ID NO 97) for the Adhiron 81 amino acid scaffold. The alpha helix, beta sheets and the insertion regions for loop1 and loop2 are highlighted.

FIG. 7 shows biochemical characterisation of Adhiron scaffold and sequencing of the library. (A) Differential scanning calorimetry was performed to determine the melting temperature of the Adhiron scaffold (Tm 101° C.). (B) Circular dichroism was used to examine the structure of the Adhiron scaffold and of three selected Adhiron proteins containing loop insertions and all show very high 13 structure. (C) The Adhiron phage library was used to infected *E. coli* ER2738 cells. 96 random clones were isolated and sequenced. The graph represents the percentage of each amino acid within the loop regions. An ideal library would contain 5.26% of each amino acid; cysteine was not included in the library.

FIG. 8 shows a comparison of the stability of (A) the Adhiron scaffold compared with (B) a representative small soluble well characterised protein, lysozyme, by differential scanning calorimetry. (C) shows that for an Adhiron selected to bind to a myc antibody, the addition of the loops into the scaffold reduces the Tm to 85° C. but this still represents a higher melting temperature than most scaffold proteins. This Adhiron protein can undergo repeated cycles of denaturation and renaturation as shown by the series of scans.

FIG. 9 shows phage ELISA results for yeast SUMO (ySUMO). (A) Phage ELISA using 24 clones isolated from the third pan round. Phage produced by each clone were incubated in wells containing ySUMO or control. The image was recorded three minutes after addition of 3,3',5,5'-Tetramethylbenzidine (TMB) substrate. (B) Graph showing the absorbance at 560 nm of the phage ELISA for ySUMO (hatched) and control (white) wells.

FIG. 10 shows purification and characterisation of an Adhiron specific for yeast SUMO (Ad-ySUMO). (A) Ad-ySUMO was expressed in BL21 cells and cell lysates were heated to 50° C., 60° C., 70° C., 80° C., 90° C. and 100° C. for 20 minutes and the precipitate was removed by centrifugation at 15,000×g. Aliquots of 5 µl of cleared lysates for each temperature were separated on a 15% SDS-PAGE gel, and stained with coomassie to visualise the proteins. (B) Lysates were incubated with Ni-NTA beads for 1 hr. Post incubated lysate (5 µl) and purified Ad-ySUMO (10 µl) were run on a 15% SDS-PAGE gel and stained with coomassie for visualisation. (C) Biotinylated Ad-ySUMOs were used to detect ySUMO (hatched bars) and did not detect human SUMO (white bars) by ELISA. (D) Western blots using biotinylated Ad-ySUMO clones 10, 15, 20, and 22 against 0.5 µg of yeast SUMO (upper panel) and mixed with 20 µg of HEK293 cell lysate (lower panel).

FIG. 11 shows phage ELISA results for Adhirons identified in screens against a series of targets, i.e. growth factor protein FGF1 (A), a cell surface receptor CD31 (B), and a peptide (C). Graphs represent the absorbance readings of each well after the addition of TMB. The wells containing the target are shown as hatched bars whilst the control wells are shown as white bars.

FIG. 12 shows immunofluorescence images of HPV16 E5 GFP (target) and HPV16 E5 GFP without epitope for Adhiron (control). Adhiron E5 was conjugated to quantum dots and used to detect E5 protein in the mammalian cells. Cells were stained with DAPI (DNA stain), GFP, and E5 (with the Adhiron-Quantum dots).

FIG. 13 shows an Adhiron targeting hSUMO2. (A) An ABP raised against hSUMO2 was tested to determine specificity for hSUMO1 and hSUMO2 by ELISA. The hSUMO2 ABP specifically bound to hSUMO2, which was reflected in the binding affinity. (B) Blot showing the ability of the hSUMO2 ABP to inhibit RNF4's SUMO-targeted ubiquitin ligase activity. (C) A control vector or hSUMO2 binder was expressed in cells and analysed using an anti-FLAG antibody and cultured with arsenic to induce nuclear bodies, PML (green). RNF4 promotes degradation of PML. Blocking the interaction between hSUMO2 and RNF4 alters PML degradation. This is the first description of a hSUMO2 binding protein that specifically binds to and inhibits hSUMO2 without interacting with hSUMO1. The hSUMO2 Adhiron also specifically blocks the domain that it's interacting with and does not affect other functions of the hSUMO2, as demonstrated in (C).

FIG. 14 shows a graph that represents a blood clot formation and lysis turbidity assay. The solid line represents the normal formation and lysis. The dashed lines represent the effect of five different Adhirons on this process. The five different Adhirons contain different epitopes and are having different effects on clot formation and lysis. Some are prolonging clotting time, some are prolonging lysis time and some are prolonging clotting and lysis time. One of the Adhirons is completing inhibiting clot formation. This demonstrates that the different Adhirons are binding to and inhibiting different regions of fibrinogen and therefore represent a really novel way of studying protein function.

Figure 17A:
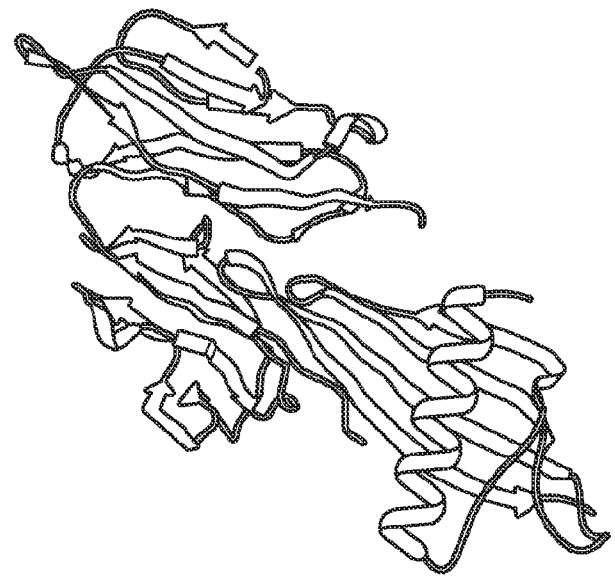
Figure 17B:
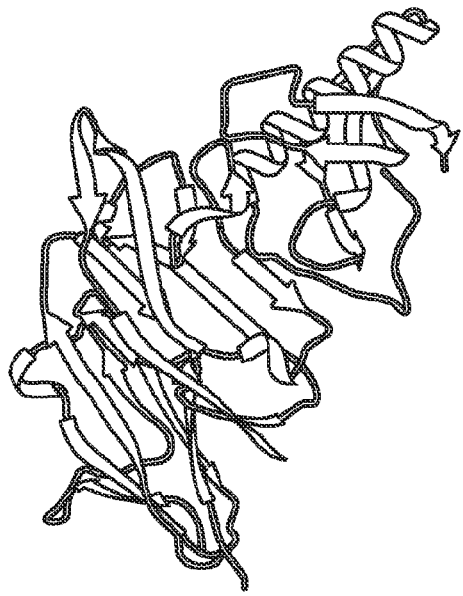

FIG. 17 shows the co-crystal structure of FcγRIIIa and bound Adhiron. (A) The Adhiron binds to an allosteric site that affects receptor binding to IgG. This site has also been identified as a target for small molecule drug design providing evidence that Adhirons can provide important information about druggable sites. (B) Adhirons have also been found to target the direct binding site of IgG on FcγRIIIa. The Adhiron contained two loops and a 4 amino acid unstructured N-terminal sequence. The N-terminus peptides are also contributing to the interaction between Adhiron and FcγRIIIa. The information gained by understanding the binding interaction between the Adhiron and FcγRIIIa will help identify small molecules via in silico screening. This provides an intriguing novel approach for future drug discovery methodologies. In addition the crystal structures demonstrate the ability of the scaffold to present loops that can either extend the beta sheets of the core scaffold or more flexible loops that create alternative conformational interaction surfaces. This is facilitated by the inherent core stability of the scaffold, which potentially makes this scaffold unique.

Figure 18A:
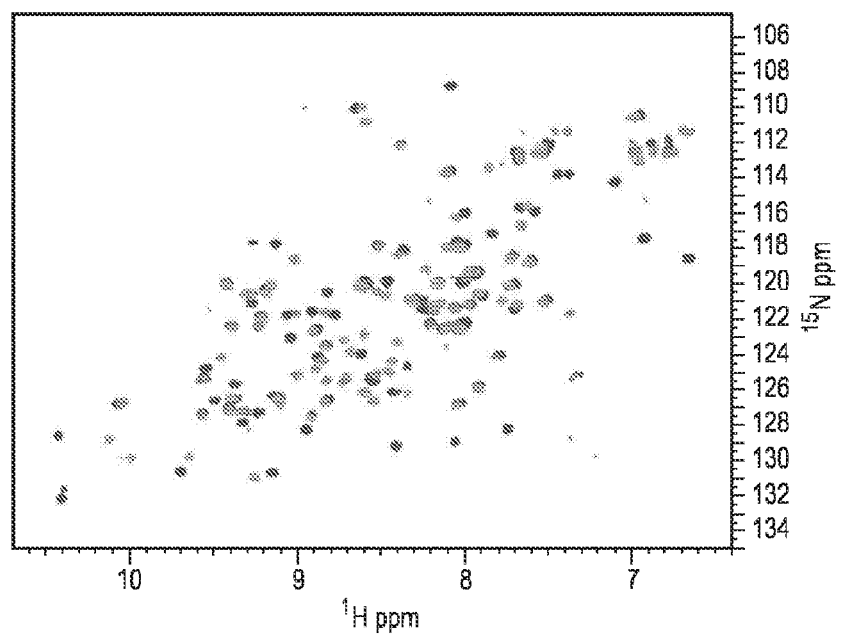
Figure 18B:
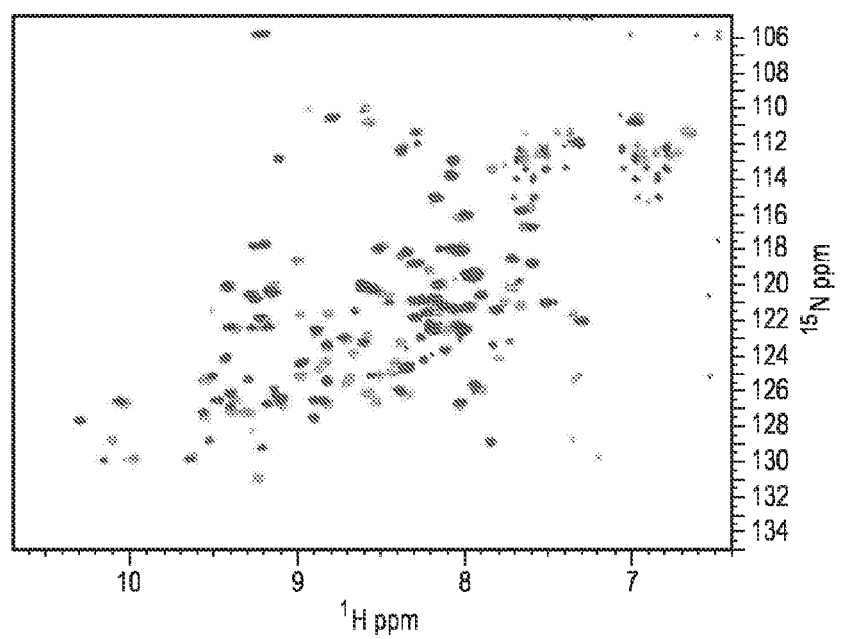

FIG. 18. NMR spectra. (A) Overlay of 1H-15N HSQC fingerprint spectra for the ABP scaffold (light grey) and Yeast Sumo Adhiron 15 (dark grey). (B) Overlay of 1H-15N HSQC fingerprint spectrum for Yeast SUMO Adhiron 15 (dark grey) and 1H-15N TROSY HSQC spectrum for the Yeast SUMO protein and Yeast SUMO-Adhiron 15 complex (light grey).

Figure 19:
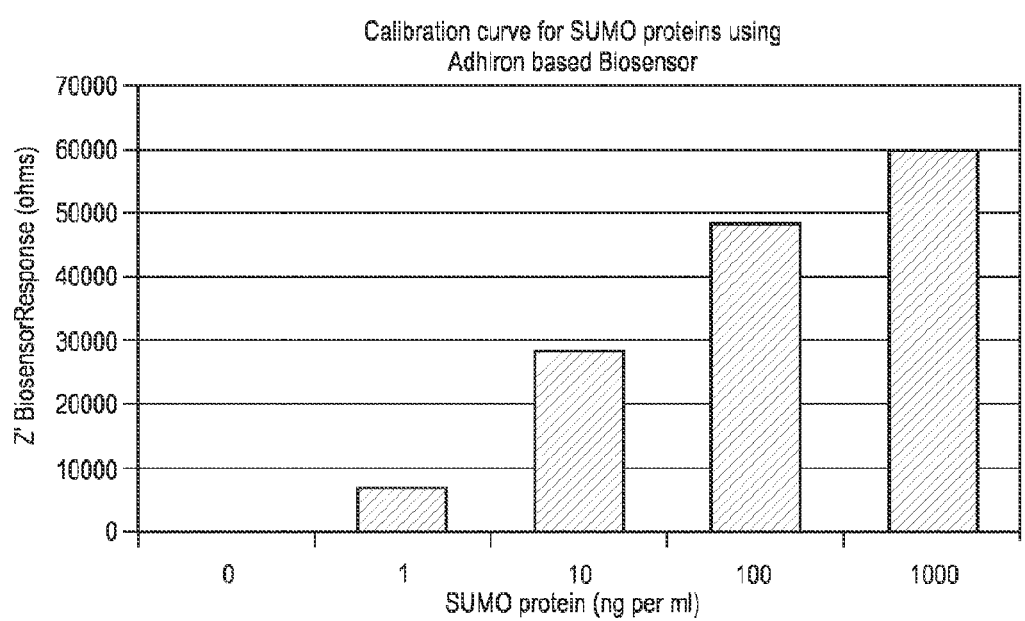

FIG. 19 shows a graph of the change of impedance versus concentration of SUMO binding Adhiron. This provides an example of the potential use of Adhirons in impedance based biosensor devices and shows that Adhirons bound to a surface have a larger dynamic range compared to antibodies.

FIGS. 20 to 24 show sequence alignments of the LOOP 1 and LOOP2 regions of Adhirons selected against a range of targets. This analysis allows identification of the range of binders against a given target and facilitates the development of potential consensus binding regions in some cases.

Figure 20:
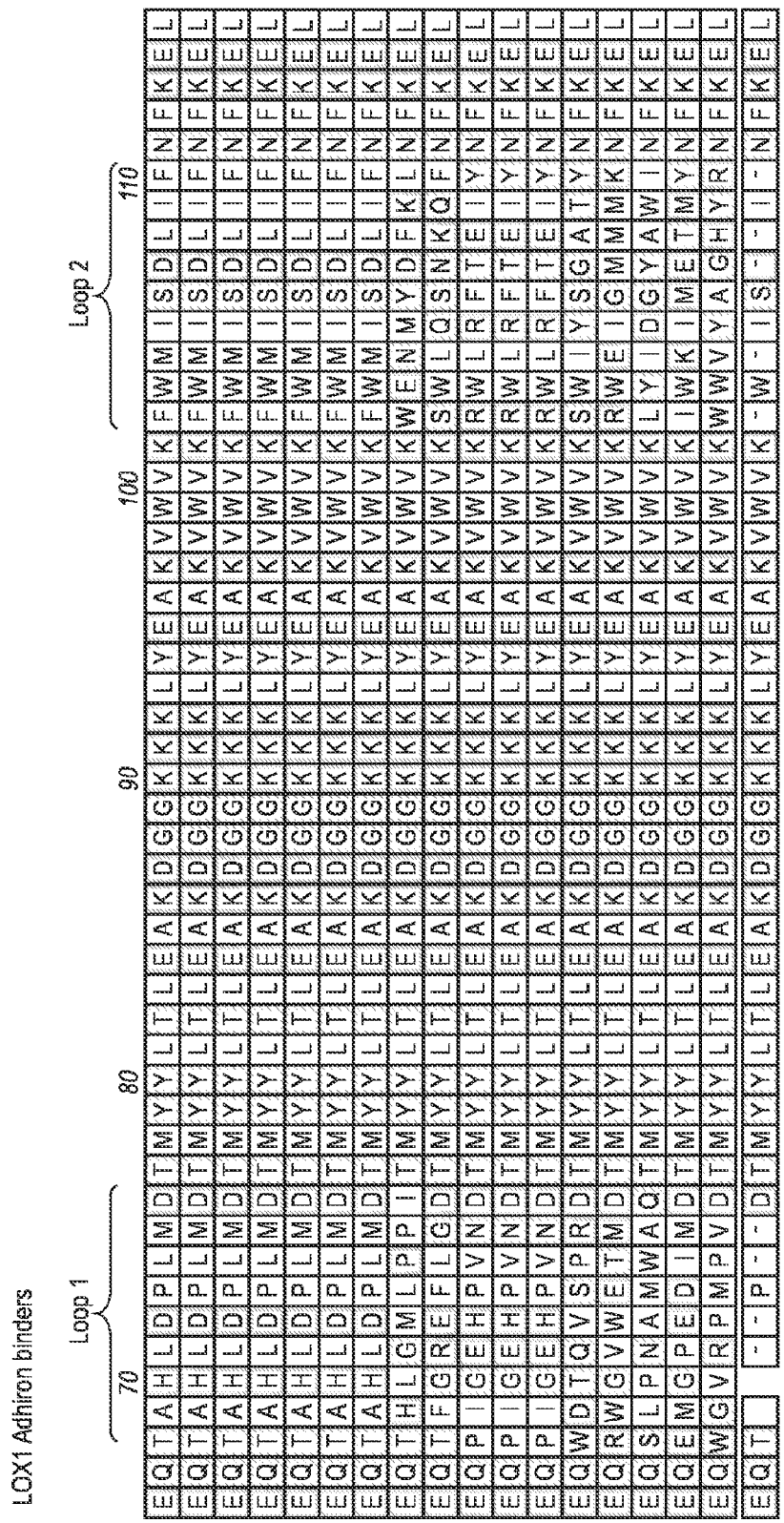

FIG. 20 shows a sequence alignment of LOOP1 and LOOP2 regions of several Adhirons (SEQ ID NOS 98-115) that bind to Lectin-like oxidized LDL receptor-1 (LOX1).

Figure 21:
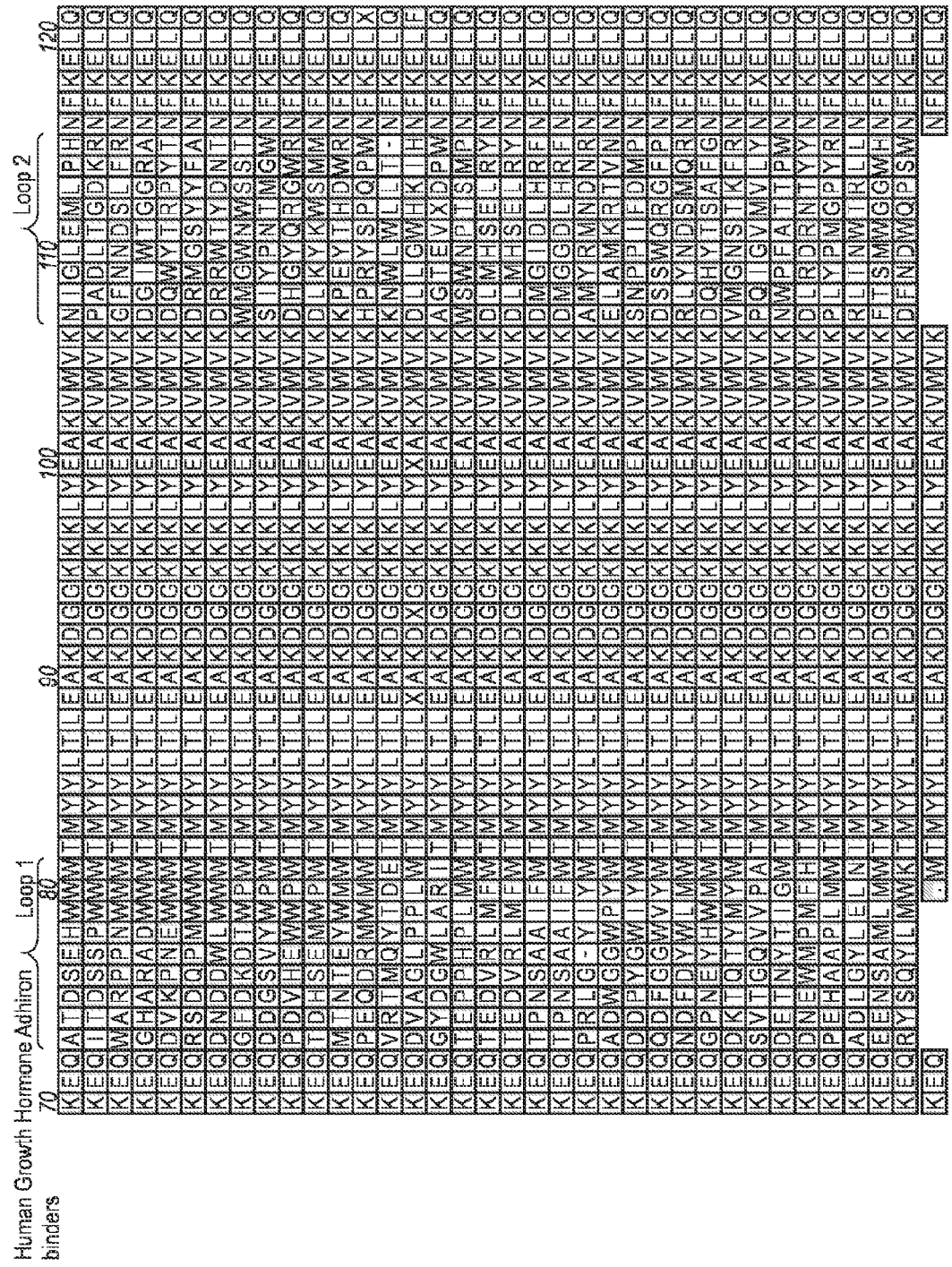

FIG. 21 shows a sequence alignment of LOOP1 and LOOP2 regions of several Adhirons (SEQ ID NOS 116-151) that bind to Human Growth Hormone (HGH).

Figure 22:
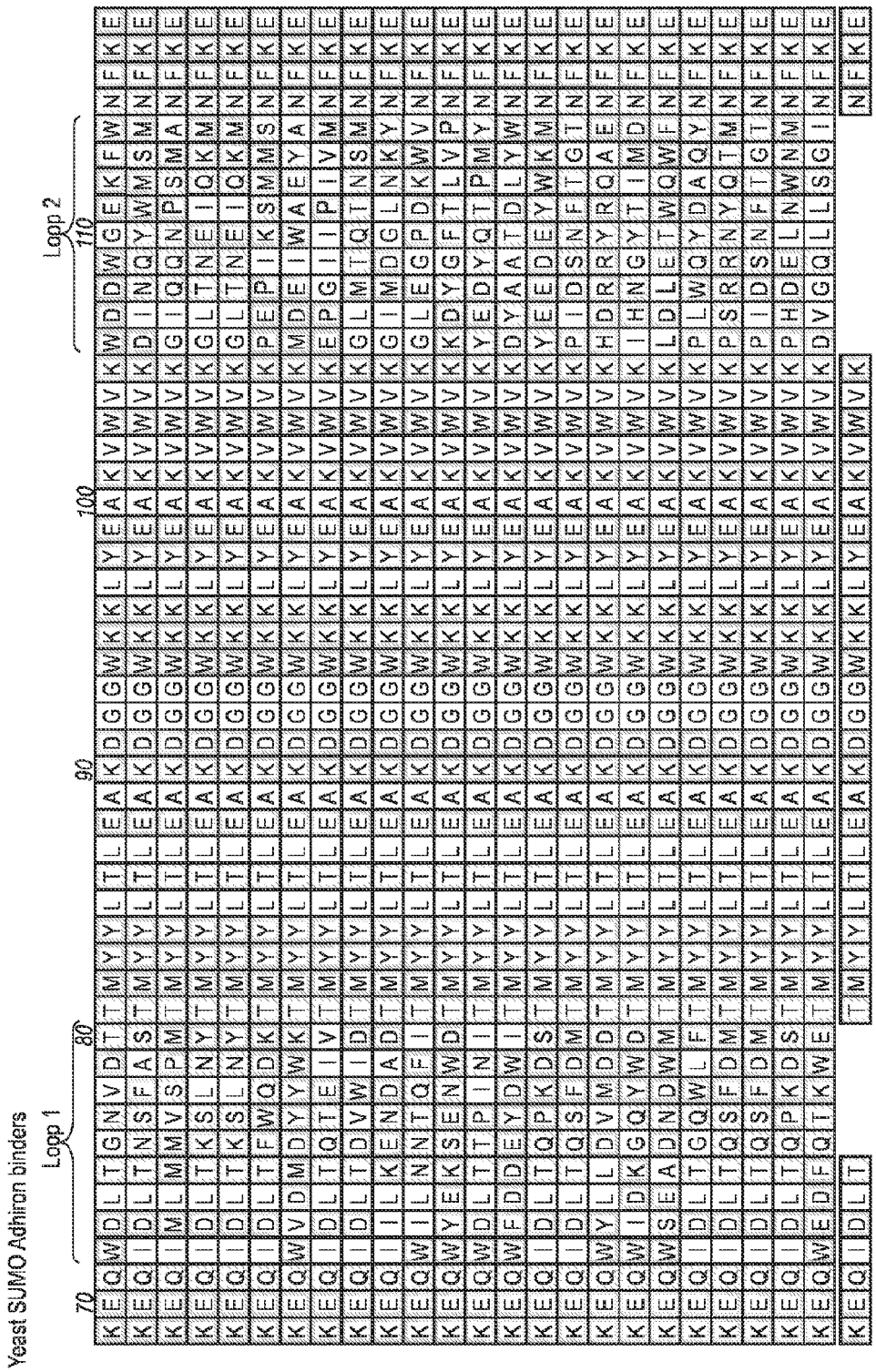

FIG. 22 shows a sequence alignment of LOOP1 and LOOP2 regions of several Adhirons (SEQ ID NOS 152-176) that bind to yeast small ubiquitin-like modifier (SUMO).

Figures 23, 24:
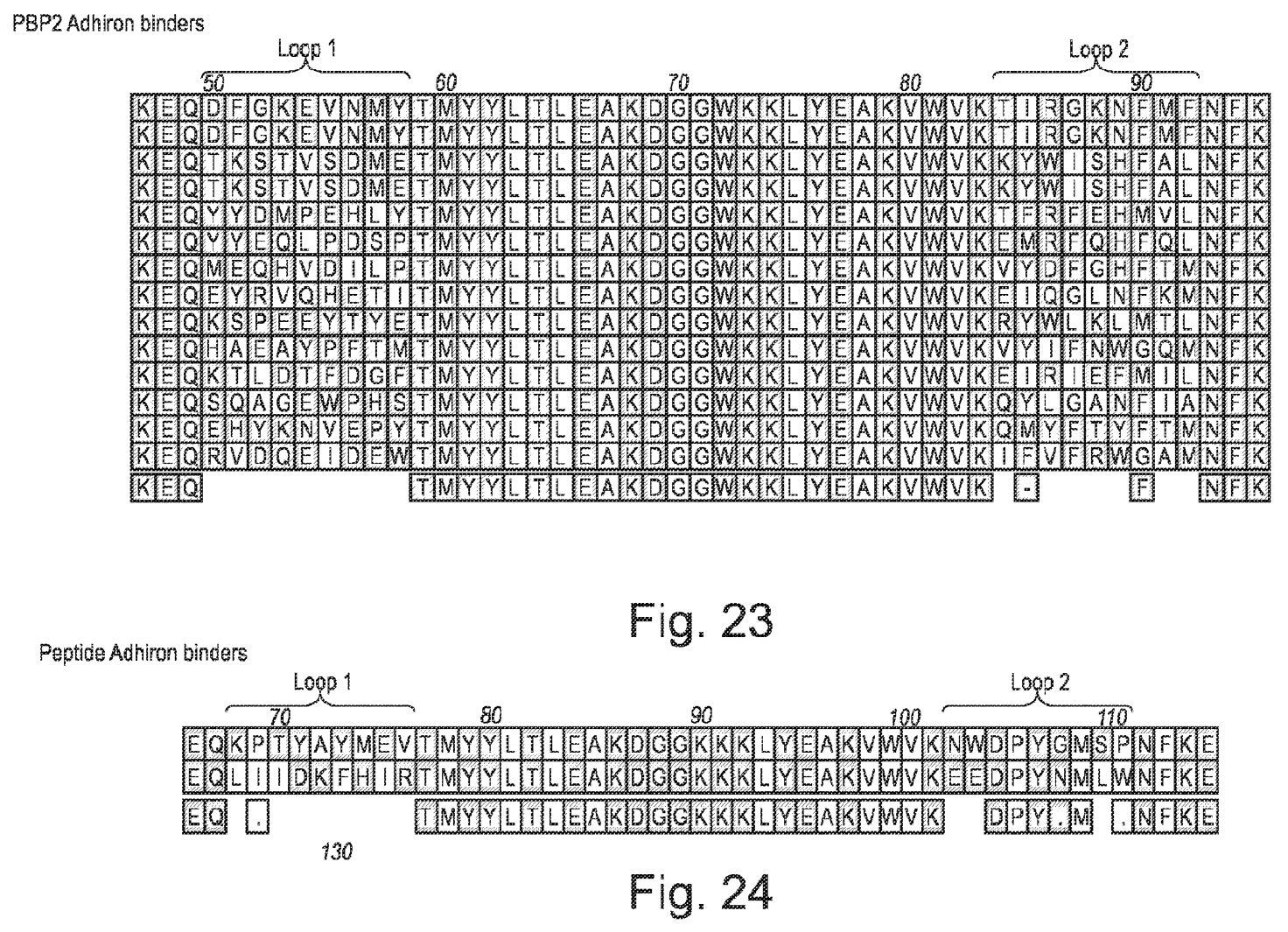

FIG. 23 shows a sequence alignment of LOOP1 and LOOP2 regions of several Adhirons (SEQ ID NOS 177-191) that bind to penicillin binding protein 2a (PBP2a).

FIG. 24 shows a sequence alignment of LOOP1 and LOOP2 regions of several Adhirons SEQ ID NOS 192-194) that bind to a peptide target.

Figure 25:
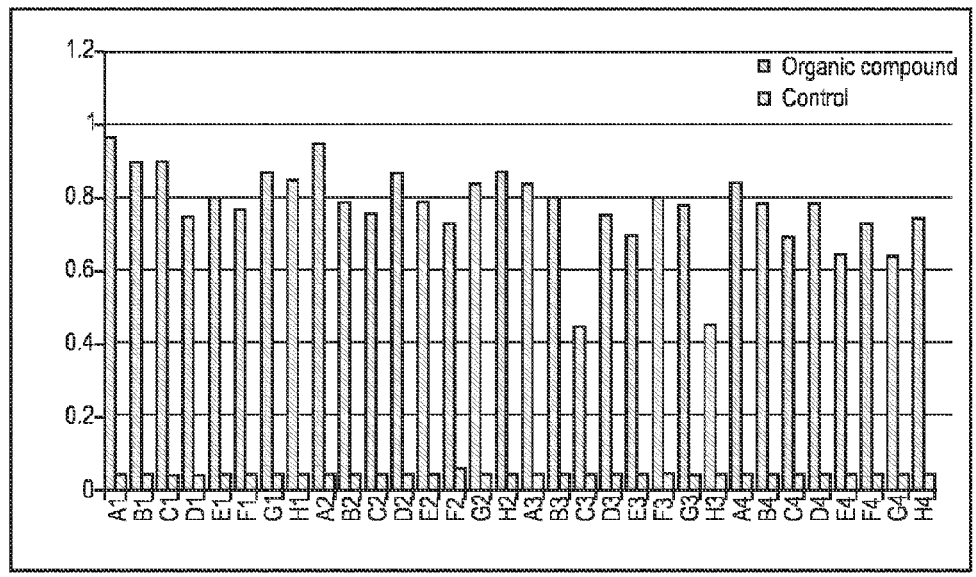

A FIG. 25 shows phage ELISA results for Adhirons identified in screens against an organic compound, posaconazole. Graphs represent the absorbance readings of each well after the addition of TMB. The wells containing the target are shown as hatched bars whilst the control wells are shown as white bars.

Figure 26:
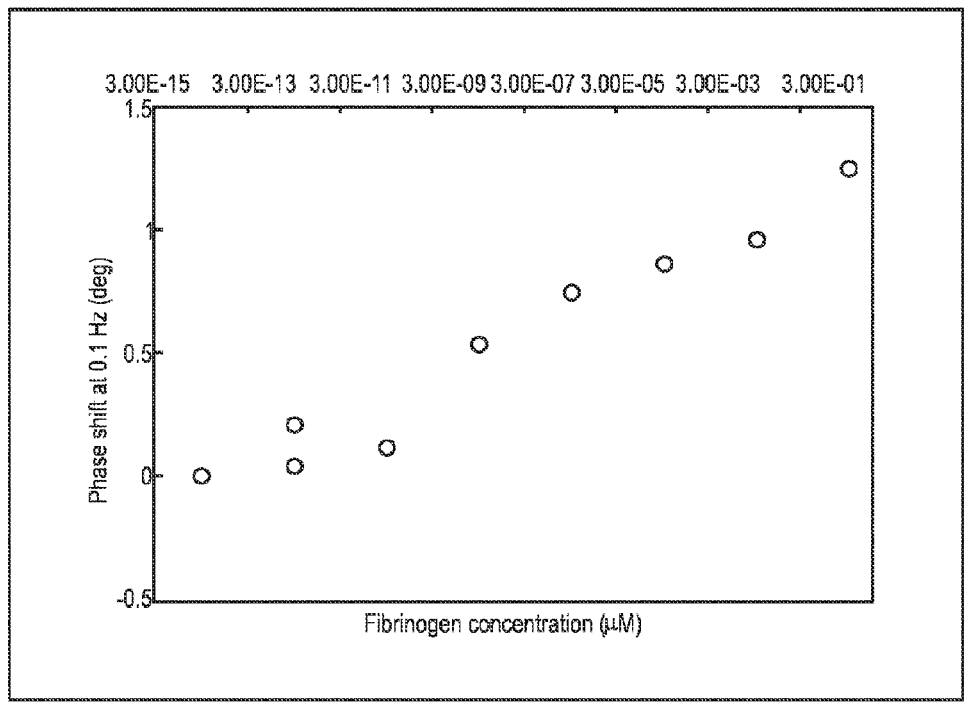

FIG. 26. A graph of the change of impedance based detection of various concentrations of fibrinogen from micromolar to attomolar by a fibrinogen binding Adhiron. This provides an example of the potential use of Adhirons in impedance based biosensor devices and shows that Adhirons bound to a surface can detect low concentrations of target protein within a 15 minute incubation and display a large linear dynamic range. The two data points at $3 \times 10^{-12}$ micromolar were measured immediately after adding the analyte (lower data point) and after a 15 minute incubation (upper data point).

Figure 27:
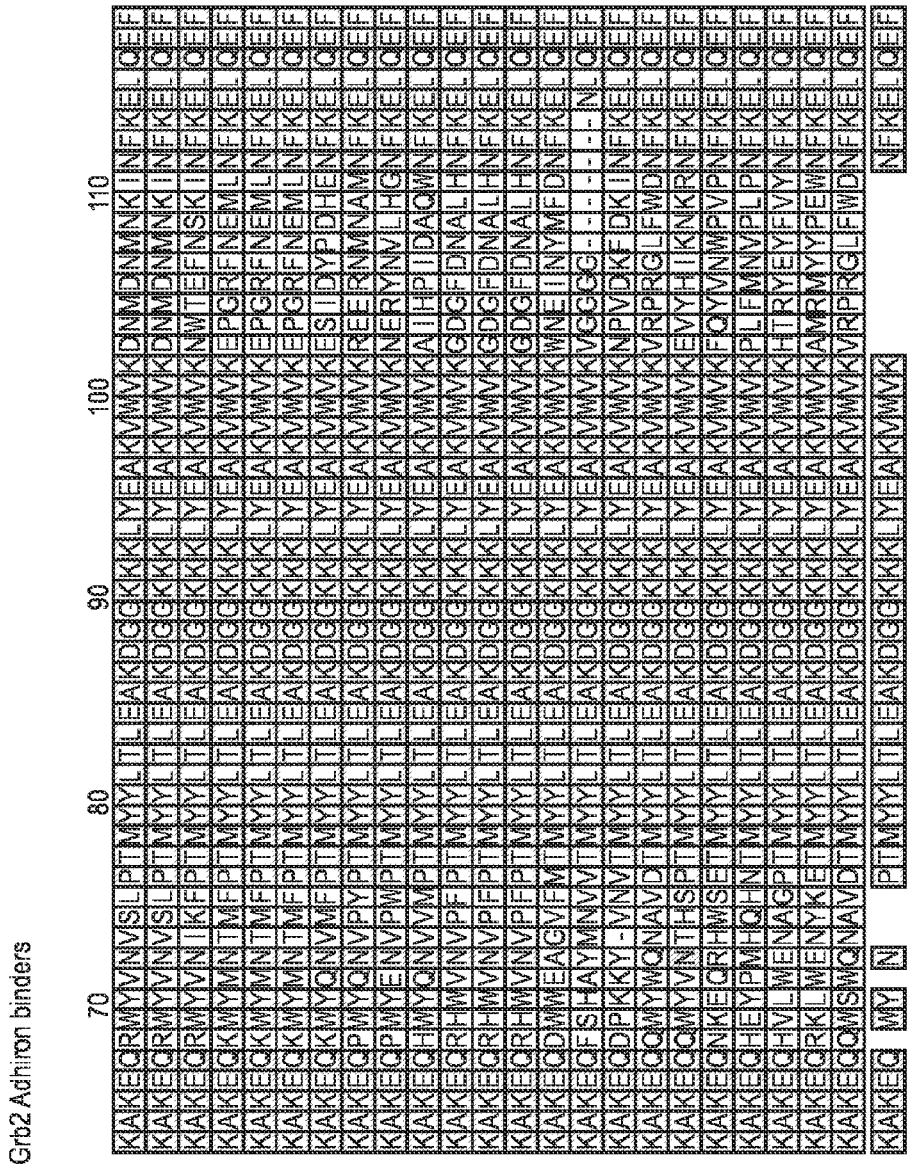

FIG. 27 shows a sequence alignment of LOOP1 and LOOP2 regions of several Adhirons (SEQ ID NOS 195-218) that bind to Growth factor receptor-bound protein 2 (Grb2) Src homology 2 domain.

Figure 28:
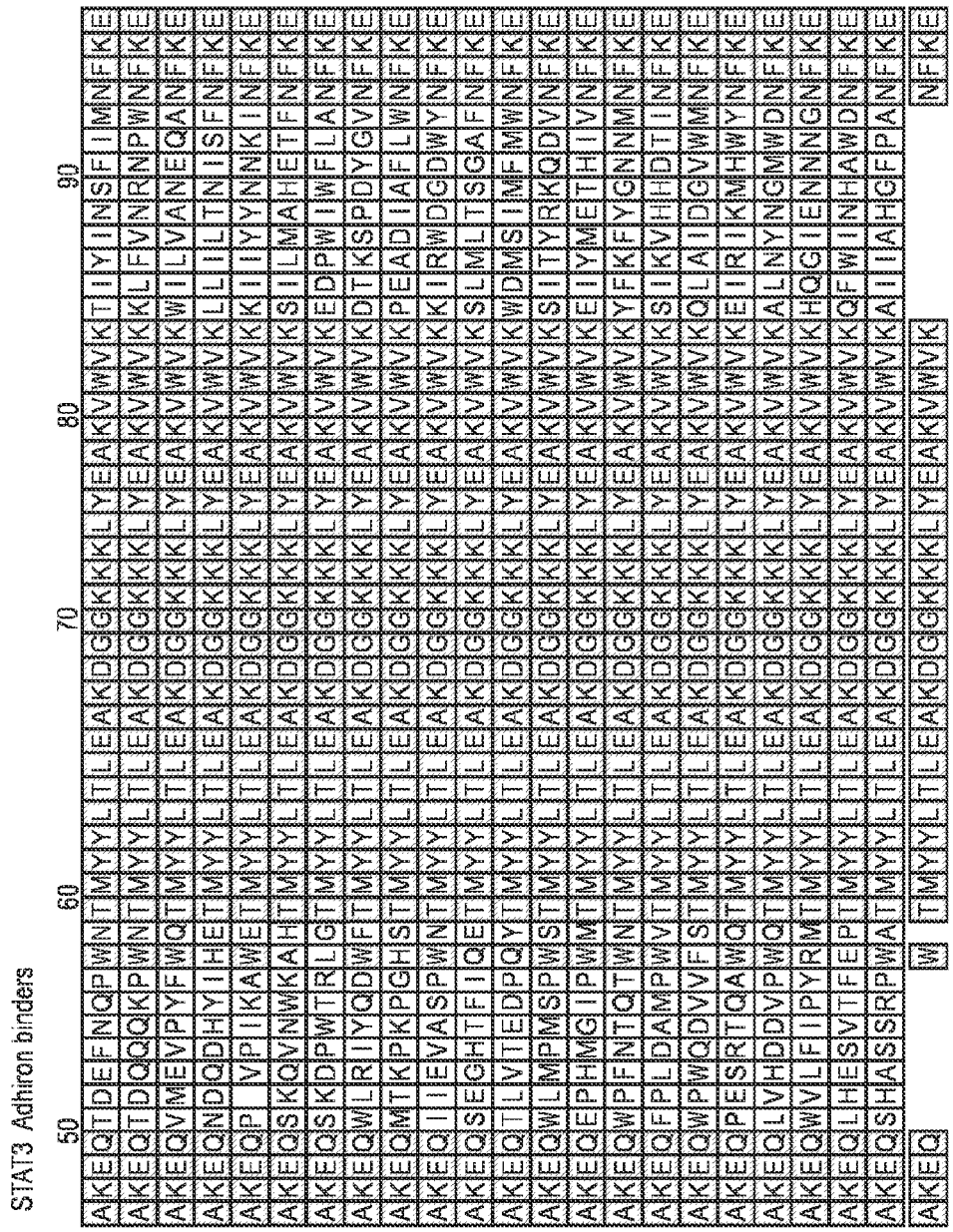

FIG. 28 shows a sequence alignment of LOOP1 and LOOP2 regions of several Adhirons (SEQ ID NOS 219-241) that bind to Signal Transducer and Activator of Transcription 3 (STAT3) Src homology 2 domain.

It has been stated that "To prompt wider interest in a particular protein scaffold, it is necessary to demonstrate that specificities for different kinds of relevant ligands can be generated, that the derived binding proteins are practically useful, and that they offer at least some benefits over conventional antibody fragments. These criteria are not met by many of the protein scaffolds proposed so far and for most of them merely initial engineering efforts have been described." (Skerra 2007). The present invention is therefore of clear value in providing a useful, versatile and attractive protein scaffold, as demonstrated below.

The high level of success in terms of identifying important bioactive binding proteins attributable to the novel Adhiron scaffold and derived library is due in large part to the very high stability of the core scaffold which provides a highly rigid framework upon which variable loop regions can be displayed. These loop regions have sufficient flexibility to adopt a range of conformations and can thus interact with a wide range of conformational features on target molecules allowing selection of binding reagents against a wide range of molecular targets, including notable small organic molecules. These structural aspects of this unique scaffold lead to functional outcomes that have not been achieved with other scaffold proteins.

There may also be benefits in the use of a plant-based protein for many applications, particularly those involving humans since the protein is not derived from a human protein and therefore will not be involved in natural interactions with human proteins. The only potential interactions would be against cysteine proteases but the active binding regions that could interact with such proteins are typically replaced or removed in the Adhiron scaffolds. However, humans come into contact with and tolerate plant-derived proteins constantly through for example, food, cosmetic products, and medicinal compositions.

Creation of an Exemplary Scaffold Protein (Termed PHYTC57)

Introduction

A consensus approach to protein design starts with a multiple sequence alignment of members of a protein family to derive a single consensus sequence in which each position is normally occupied by the residue that occurs most frequently. Residues that define the structure, folding pathway, and stability of the folded protein will tend to be conserved, while those required for a common biological function such as catalytic residues in an enzyme, or residues that interact with a conserved target protein, are also likely to be conserved. A natural protein will not usually contain all the conserved consensus residues because proteins only evolve to be sufficiently stable to perform their biological role in vivo, and in many cases this may include a degree of instability to facilitate turnover and regulation of biological processes (Steipe, Schiller et al. 1994).

We were interested to explore whether a consensus approach could be applied to enhance the inhibitory properties and stability of phytocystatins. Phytocystatins are small (~100aa) protein inhibitors of cysteine proteases (Kondo et al. 1991). A detailed phylogenomic analysis of the cystatin superfamily reveals the relationships between the different classes of cystatins (Kordis and Turk 2009). Phytocystatins comprise three regions that are involved in binding to cysteine proteases, the N-terminal region, a QVVAG (SEQ ID NO 83) loop and a PW loop (Margis et al. 1998). Previously, based on a structural model and sequence alignments, we generated a variant of rice cystatin, oryzacystatin I (OSA-I or OC-I), that lacks residue Asp 86, close to the conserved PW loop and named OSA-IΔD86. This variant displayed a 13-fold improvement in $K_i$ against both papain and the *Caenorhabditis elegans* gut-specific cysteine protease GCP-1 (Urwin et al. 1995; McPherson et al. 1997; Urwin et al. 1997; Urwin et al. 1998; Urwin et al. 2000; UnNin et al. 2001; Urwin et al. 2003; Lilley et al. 2004). We then demonstrated good levels of transgenic resistance, against plant nematodes, conferred by OSA-IΔD86 and other cystatins when expressed in the specialised feeding cells that develop within a nematode parasitized plant (Urwin et al. 1995; McPherson et al. 1997; Urwin et al. 1997; Urwin et al. 1998; Urwin et al. 2000; Urwin et al. 2001; Urwin et al. 2003; Lilley et al. 2004).

Here we describe the design, construction and characterisation of a consensus phytocystatin based on multiple sequence alignment of the amino acid sequences of 57 phytocystatins. We show that this consensus phytocystatin displays efficient inhibition of the cysteine protease papain and enhanced stability in thermostability and digestibility assays.

Materials and Methods

Design of the Consensus Phytocystatin Hereinbelow Referred to as PHYTC57

Following a tBLAST search of the GenBank data base a multiple alignment of phytocystatin sequences was performed using CLUSTALW (<http://clustalw.genome.ad.jp/>; BLOSUM62; Gap opening penalty=12; Gap extension penalty=2) with further manual alignment using the program CINEMA (<http://www.bioinf.manchester.ac.uk/dbbrowser/CINEMA2.1/>) (Parry-Smith et al. 1998; Lord et al. 2002). The most commonly used amino acid at each position was determined and the variable N- and C-terminal ends were truncated to give a consensus protein of 95 amino acids in length. A synthetic coding region was designed to encode the consensus phytocystatin (phytc57) with codon usage optimised for expression in *E. coli* by using the appropriate codon frequency table (<http://www.kazusa.or.jp/codon/>). The coding region was constructed from six oligonucleotides (P1-P6; see FIG. 1) each of approximately 70 nt in length that included regions of at least 10 nt overlap between adjacent oligonucleotides. The flanking oligonucleotides P1 and P6 also contained an SfiI site and a NotI site, respectively, for cloning into the vector pDHisII where the coding sequence was fused to the vector-derived pelB signal sequence coding region. Retention of a signal peptidase cleavage site was checked by submitting the N-terminal sequence of the PELB/PHYTC57 protein to the automatic signal sequence prediction programme Signal P (Bendtsen et al. 2004; <http://www.cbs.dtu.dk/services/SignalP/>). Pairs of oligonucleotides (P1+P2), (P3+P4) and (P5+P6) were annealed and converted to double stranded fragments by self-priming. The reactions (10 µl) contained 25 pmole of each primer, 0.2 mM of each dNTP, 1× Pwo Buffer (10 mM Tris-HCl pH 8.85, 25 mM KCl, 5 mM $(NH_4)_2SO_4$, 2 mM $MgSO_4$) and 5 units Pwo DNA polymerase (Boehringher) and were subjected to one cycle of 95° C. for 2 min, 25° C. for 4 min and then 72° C. for 5 min. The subsequent joining of the products (P1/P2) to (P3/P4) and then (P1/P2/P3/P4) to (P5/P6) was performed in an identical manner, to generate full-length product. A 5 µL aliquot of the final reaction was used as template in a 50 µL PCR together with 50 pmole each of the flanking primers P1 and P6, 0.2 mM each dNTP, 1× Pwo buffer and 5 units Pwo. The reaction was subjected to 95° C. for 1 min, then 30 cycles of 95° C., 30 sec, 55° C., 30 sec and 72° C., 30 sec. The product was digested with SfiI and NotI, recovered from an agarose gel and cloned into SfiI and NotI restricted pDHisII. The newly constructed gene region was sequenced to confirm correct primer assembly and the expected DNA sequence. The sequence of the consensus coding region is shown in FIG. 1A.

Synthesis of Other Phytocystatin Genes

Synthetic DNA sequences optimised for *E. coli* expression were similarly designed, constructed and cloned for phytocystatins from rice (*Oryza sativa*l; osa-IΔD86 a modified form of oc-I GenBank accession number U54702 lacking the codon for Asp 86 (Urwin et al. 1995), satsuma orange (*Citrus unshiu*; cun, GenBank accession number C95263) and papaya (*Carcia papaya*; cpa, GenBank accession number X71124 (Song et al. 1995). The chicken egg white cystatin gene (cewc) sequence was amplified from a pQE30-derived recombinant plasmid using the gene specific primers:

cewcF
(SEQ ID NO 10)
5'ATTAGCGGCCCAGCCGGCCATGGCCAGCGAGGACCGCTCCCGGC3' cewcR
(SEQ ID NO 11)
5'CGCTGTACTTGCGGCCGCCCTGGCACTTGCTTTCCAGC3' that introduced an SfiI site and NotI site (underscored) respectively.

PCR reactions were carried out with 50 pmole of each primer, a final concentration of 0.2 mM of each dNTP (Promega) and approximately 10 ng template in a volume of 50 µl containing 1× SuperTaq buffer (10 mM Tris-HCl pH 9.0, 1.5 mM $MgCl_2$, 50 mM KCl, 0.1% (v/v) Triton X-100). To ensure high fidelity amplification during the PCR a 10:1 mix of SuperTaq (HT Biotechnology):Pfu (Boehringer Mannheim) DNA polymerases were used with 1 unit of polymerase mix per reaction. The reactions were subjected to 1 cycle of 95° C. for 1 min then 20 cycles of 95° C. for 30 sec, 55° C. for 30 sec and 72° C. for 30 sec. A final step of 72° C. for 30 sec was used to ensure that all products were full length.

pDHisII Construction

Phytocystatin coding regions were initially cloned into a modified version of the phagemid vector pHEN1 (Hoogenboom et al. 1991) as gene III fusions. The pHEN vector was modified by addition of a hexa-histidine region encoded by complementary oligonucleotides that were phosphorylated and annealed to create a linker with appropriate single strand ends for ligation with the NotI cleaved vector. The oligonucleotide sequences were;

(SEQ ID NO 12)
HisF: 5'-GGCCGCAGAGGATCGCATCACCATCACCATCACGG-3'

(SEQ ID NO 13)
HisR: 5'-GGCCCCGTGATGGTGATGGTGATGCGATCCTCTGC-3' and the NotI complementary ends are underscored.

The pHEN1 vector was digested with NotI and dephosphorylated using 5 units of shrimp alkaline phosphatase (NEB) in a 50 µl reaction containing 100 mM NaCl, 50 mM Tris-HCl (pH 7.9), 10 mM $MgCl_2$ and 1 mM DTT for 30 minutes at 37° C. before heating to 65° C. for 15 min. The distal NotI site was destroyed by PCR mutagenesis using the primers (SEQ ID NO 14)
XhoF: 5'ATCACGCTCGAGCAGAACAAAAACTCATCTCAG3'

(SEQ ID NO 15)
XhoR: 5'TGTTCTGCTCGAGCGTGATGGTGATGGTGATGGCG3'

(SEQ ID NO 16)
BamHIR: 5'TGGCCTTGATATTCACAAACG3'

(SEQ ID NO 17)
M13R: 5'AGCGGATAACAATTTCACACAGGA3'

The XhoF primer was used together with BamHIR primer and the XhoR together with the M13R primer to generate two fragments that were annealed and amplified in a second PCR that included primers M13R and BamHIR. The introduced XhoI restriction site is underscored. The resulting product was cloned as an SfiI/BamHI fragment into pHEN1 vector similarly digested. The presence of the XhoI site was screened for by restriction analysis of isolated phagemid DNA and the insert in a positive clone, pDHisII (FIG. 1B), was confirmed by DNA sequence analysis.

Expression of Cystatins in pDHisII

Initially, expression of cystatins were performed using constructs in the vector pDHisII which adds C-terminal $RGS(H)_6$ and myc tags. Expression studies in the *E. coli* host strain HB2151 allow suppression of the amber codon within the cystatin-gene III fusion resulting in accumulation of cystatin in the periplasm. Cultures (1 L) were grown in 2×TY media with 0.1% (v/v) glucose and 100 □g/mL ampicillin then induced by IPTG to 1 mM and grown at 30° C., 16 hours. Cell pellets were resuspended in 20 mL 50 mM Tris pH 8, 20% (w/v) sucrose at 4° C. and periplasmic preparations performed. To the periplasmic fraction 1 mL Ni-NTA resin (GE Healthcare) was added and incubated with mixing for 16 hours at 4° C. The resin was washed 8 times with 1 mL aliquots of wash buffer (50 mM NaHPO$_4$, 500 mM NaCl, pH 6), then 3 times with wash buffer containing 40 mM imadiazole. Cystatin was eluted with 200 μL wash buffer containing 250 mM imadiazole at 4° C. for 1 hour, before dialysis against PBS. Protein was aliquoted and frozen in liquid nitrogen. Samples were analysed by SDS-PAGE and electrospray mass spectrometry.

Expression of Cystatins in pET101

For more efficient expression of soluble protein, the phytocystatin genes were sub-cloned together with the C-terminal 6-His tag from pDHis II into pET101 by directional TOPO cloning (Invitrogen). The primers

```
                                                (SEQ ID NO 18)
cystaSDFWD 5'CACCATGAAATCACTATTGCTTACG3'

(SEQ ID NO 19)
cystaSDREV 5'CTACTAGTGATGGTGATGGTGATGCG3'
``` were used to PCR amplify the phytocystatins genes from the original cloning vector pDHisII using the conditions described above. Positive clones were confirmed by DNA sequence analysis and were introduced into BL21(DE3) Star cells (Invitrogen). Cultures were grown at 30° C. and expression of phytocystatins was induced by addition of IPTG (to 1 mM) for 16 h. The cells were harvested by centrifugation (4,000×g, 10 min), sonicated on ice (3×1 min), the cell debris pelleted by centrifugation (10,000×g, 10 min). The supernatant was loaded onto a metal chelating column (Pharmacia) charged with 0.1 mM NiCl$_2$. After extensive washing the phytocystatins were eluted with 100 mM imidazole and dialysed extensively into HBS buffer (10 mM HEPES pH 7.4, 150 mM NaCl, 0.005% P20) and stored at −70° C.

Papain Assay

The inhibition of papain (Sigma) was assayed using pGlu-Phe-Leu-p-NA (Sigma), a synthetic substrate for cysteine proteinases (Filippova et al. 1984). 100 ng of papain, in 50 μl of incubation buffer (0.15 M MES/OH pH 5.8, 4 mM NaEDTA, 4 mM DTT), was added to 50 μl of sample, either with no cystatin or containing a known concentration of cystatin and pre-incubated for 30 minutes. 50 μl of 1 mM pGlu-Phe-Leu-p-NA (in incubation buffer and 30% DMSO) was added and papain activity monitored by a linear increase in OD at 415 nm, over 15 min at 25° C.

Surface Plasmon Resonance (SPR) Experiments

Papain was obtained from Sigma as a lyophised powder. For the SPR experiments a stock solution of 1 mg/ml was prepared by dissolving in HBS buffer containing 1 mM DTT. This stock was diluted to the required concentrations with the same buffer. All SPR experiments were performed on a BIACORE 3000 instrument using an NTA sensorchip. The running buffer was HBS-EP (10 mM HEPES, 0.15 M NaCl, 0.005% P20, pH 7.4) and all experiments were carried out at 25° C. Phytocystatins were immobilised (approximately 400 response units (RU) on flowcells 2 to 4 with flowcell 1 left blank. To monitor binding of papain to the phytocystatins, 240 μl of HBS buffer was injected over all flow cells at a flow rate of 80 μl/min (association phase) followed by normal buffer flow for 3 min (dissociation phase) to provide a subtraction blank. This injection was repeated with papain. Proteins were stripped from the sensorchip using EDTA and the surface re-charged with nickel before repeating the experiment with a different concentration of papain. At least 5 cycles were performed for each concentration to allow kinetic analysis. The data from these binding experiments were analysed using the Biaevaluation3 software package (BIACORE) and by global fitting the data to the Langmuir 1:1 binding model.

Thermal Stability of Phytocystatins

Aliquots of PHYTC57 and OSA-IΔD86 were prepared at 0.5 μg protein/mL in 50 mM phosphate buffer pH 7.4. The samples were immediately placed in a boiling water bath. Samples were removed at various times and plunged into liquid nitrogen, before storage at −70° C. Residual inhibitory activity, to determine the remaining level of functional cystatin, was determined by the papain inhibition assay.

Digestibility Assay

Simulated gastric fluid was made up as described (Astwood et al. 1996) immediately before use and contained 0.32% (w/v) pepsin (Sigma) in 0.03 M NaCl adjusted to pH 1.2 with concentrated HCl. Four replicates of PHYTC57 and of OSA-IΔD86 at 0.2 mg/ml final concentration, were incubated in SGF at 37° C. At intervals 200 μl aliquots were removed and immediately mixed with 75 μl 0.2M Na$_2$CO$_3$ to terminate digestion. Each sample was divided into three sub-samples and, as previously described (Atkinson et al. 2004), were separated on 15% SDS-PAGE gels. Two gels were stained for total protein with Coomassie blue, one to show the effect of simulated gastric fluid on PHYTC57 and the second to compare digestibility of PHYTC57 with OSA-IΔD86. The third gel was subjected to western blot analysis using a mouse antibody to detect the 6His-tag (Qiagen) of PHYTC57 with visualisation using alkaline phosphatase activity. A final sample from each time point was analysed for residual inhibitory activity against papain by the enzyme assay as outlined above.

Results

Synthesis of Phytocystatin Genes

For the design of the consensus phytocystatin coding region a tBLASTN search of the Genbank database was undertaken using OSA-I (*Oryza sativa*; U54702), ZMA2 (*Zea mays*; D38130) and HAN1 (*Helianthus annuus*; Q10993) protein sequences as search probes. The list of sequences used to derive the consensus sequence is shown in Table 1. Sequences were identified from databases by homology searching. The table shows a systematic name for each cystatin together with the organism name and common name of the plant and the Genebank accession number. Coding sequences were translated and aligned using the program CLUSTALW and the alignment was displayed using the program CINEMA (Parry-Smith et al. 1998; Lord et al. 2002) to allow improvement by manual alignment. A consensus sequence was then derived by identifying the most common amino acid at each position (FIG. 1A). The length of the consensus protein was set at 95 amino acids with the N-terminus positioned four residues before the conserved N-terminal glycine residue, and thus before the first β-strand (β1). The C-terminus was set 15 residues after the conserved PW motif and thus after the last β-strand (β5). These criteria were based on the X-ray structures of CEWC (Bode et al. 1988) and human stefin B (Stubbs et al. 1990) and the NMR structure of OSA-I (Nagata et al. 2000).

TABLE 1

Phytocystatin sequences used to derive the consensus (PHYTC57) sequence.

| Phytocystatin | Organism name | Common name | Accession number |
|---|---|---|---|
| AAR | Ambrosia artemisiifolia | Short ragweed | L16624 |
| ACE | Allium cepa | Onion | AA508918 |
| ATH1 | Arabidopsis thaliana | Arabadopsis | Z17618 |
| ATH2 | Arabidopsis thaliana | Arabadopsis | Z97341 |
| ATH3 | Arabidopsis thaliana | Arabadopsis | Z17675 |
| ATH4 | Arabidopsis thaliana | Arabadopsis | ATAJ110 |
| ATH6 | Arabidopsis thaliana | Arabadopsis | AC002409 |
| ATH8 | Arabidopsis thaliana | Arabadopsis | Z37263 |
| AVU | Artemisia vulgaris | Mugwort | AF143677 |
| BCA1 | Brassica campestris | Chinese cabbage | L41355 |
| BCA2 | Brassica campestris | Chinese cabbage | L48182 |
| BCA3 | Brassica campestris | Chinese cabbage | U51119 |
| CPA | Carcia papaya | Papaya | X71124 |
| CSA | Cucumis sativus | Cucumber | AB014760 |
| CSAT | Castanea sativa | Chestnut | AJ224331 |
| CUN | Citrus unshiu | Satsuma orange | C95263 |
| DCA | Daucus carota | Carrot | D85623 |
| DCAR | Dianthus caryophyllus | Carnation | AF064734 |
| GHI2 | Gossypium hirsutum | Cotton | AI728662 |
| GHI3 | Gossypium hirsutum | Cotton | AI726250 |
| GMA1 | Glycine max | Soybean | D64115 |
| GMA2 | Glycine max | Soybean | U51583 |
| GMA3 | Glycine max | Soybean | U51855 |
| GMA4 | Glycine max | Soybean | U51854 |
| GMA5 | Glycine max | Soybean | AI495568 |
| GMA7 | Glycine max | Soybean | AI938438 |
| HAN1 | Helianthus annuus | Sunflower | Q10993 |
| IBA | Ipomoea batatas | Sweet potato | AF117334 |
| MCR1 | Mesembryanthemum crystallinum | Ice plant | AA856241 |
| MCR2 | Mesembryanthemum crystallinum | Ice plant | AA887617 |
| MDO | Malus domestica | Apple tree | AT000283 |
| OSA1 | Oryza sativa | Rice | U54702 |
| OSA2 | Oryza sativa | Rice | X57658 |
| OSA5 | Oryza sativa | Rice | C25431 |
| PAM | Persea americana | Avacado | JH0269 |
| PBA | Populus balsamifera | Poplar | AI167046 |
| PCO | Pyrus comunis | Pear | U82220 |
| PTA | Pinus taeda | Pine | AI812403 |
| PTR | Populus tremula | Poplar | AI162398 |
| RCO1 | Ricinus communis | Castor bean | Z49697 |
| RCO2 | Ricinus communis | Castor bean | T23262 |
| SBI | Sorghum bicolor | Sorghum | X87168 |
| SLA | Silene latifolia | White campion | Z93053 |
| SLY1 | Lycopersicon esculentum | Tomato | AF083253 |
| SLY2 | Lycopersicon esculentum | Tomato | X73986 |
| SLY5 | Lycopersicon esculentum | Tomato | AI781497 |
| STU1 | Solanum tuberosum | Potato | L16450 |
| STU2 | Solanum tuberosum | Potato | L16450 |
| STU3 | Solanum tuberosum | Potato | L16450 |
| STU4 | Solanum tuberosum | Potato | L16450 |
| STU5 | Solanum tuberosum | Potato | L16450 |
| STU6 | Solanum tuberosum | Potato | L16450 |
| STU7 | Solanum tuberosum | Potato | L16450 |
| STU8 | Solanum tuberosum | Potato | L16450 |
| STU10 | Solanum tuberosum | Potato | X74985 |
| VUN | Vigna unguiculata | Cowpea | Z21954 |
| ZMA1 | Zea mays | Maize | D10622 |
| ZMA2 | Zea mays | Maize | D38130 |
| ZMA4 | Zea mays | Maize | AI001246 |
| ZMA5 | Zea mays | Maize | AI740162 |

The synthetic gene encoding PHYTC57 was generated from six oligonucleotides (P1-P6) each approximately 70 nt, designed to include regions of at least 10 nt overlaps between adjacent oligonucleotides as described in Materials and Methods. For comparative study of naturally occurring phytocystatins we adopted a similar synthetic gene approach using oligonucleotides for the osa-IΔD86, can (*Citrus unshiu*; Satsuma) and cpa (*Carcia papaya*; Papaya) phytocystatin coding regions designed from the unique sequence of the appropriate protein with codon changes to reflect *E. coli* codon usage. The chicken egg white cystatin (cewc) coding region was PCR amplified from a pQE-derived plasmid. The genes were initially cloned into the phage display vector pDHisII by exploiting the SfiI and NotI sites (FIG. 1B).

Cystatin Expression

Cystatins were initially expressed from pDHisII constructs and purified by Ni-NTA affinity chromatography. Analysis of the purified cystatins by electrospray ionisation mass spectrometry indicated that, unexpectedly, in each case there was a C-terminal truncation of the expressed protein. Table 2 shows the expected masses of the full-length cystatins and those with a 16 amino acid C-terminal truncation calculated using the Protein Calculator program (<www.scripps.edu/~cdputnam/protcalc.html>) together with the determined molecular masses. The sequence of the C-terminal end of the proteins is shown with the major truncation site indicated by an arrow. With the exception of CUN, the determined molecular mass is in excellent agreement with forms of the fusion proteins that had lost the C-terminal 16 amino acids, but which retain the His tag (Table 2). In the case of CUN there is truncation of fewer than 16 residues, but this was not characterised further. To ensure expression of defined protein sequences the cystatin coding regions plus His-tag were therefore sub-cloned into pET101 by PCR and TOPO-facilitated cloning and expressed in BL21 (DE3) Star cells (Stratagene). Protein expression was induced by addition of IPTG to 1 mM for 16 hours and the cystatins purified under native conditions by Ni-NTA affinity chromatography by virtue of their C-terminal hexahisitdine tag. The cystatins were separated by SDS-PAGE to examine their purity which was estimated to be >98%, their masses were in excellent agreement with the expected values by ESI-MS (data not shown) and so these proteins were used for further analyses.

TABLE 2

Electrospray mass spectrometry results for cystatins expressed from HB2151.

| Phytocystatin | Predicted mass (Da) Full length | Predicted mass (Da) Truncated | Experimental mass (Da) |
|---|---|---|---|
| OSA1ΔD86 | 14329 | 12603 | 12603.3 ± 0.8 |
| CPA | 14321 | 12596 | 12593.5 ± 6.8 |
| PHYTC57 | 13855 | 12129 | 12128.3 ± 0.8 |
| CEWC | 16399 | 14608 | 14607.4 ± 1.5 |
| CUN | 14222 | 12496 | 12728.0 ± 1.1 |

↓
. . .RGSHHHHHHARAEQKLISEEDLNGAA (SEQ ID NO 20)

Cystatin Binding Activity

Figure 3:
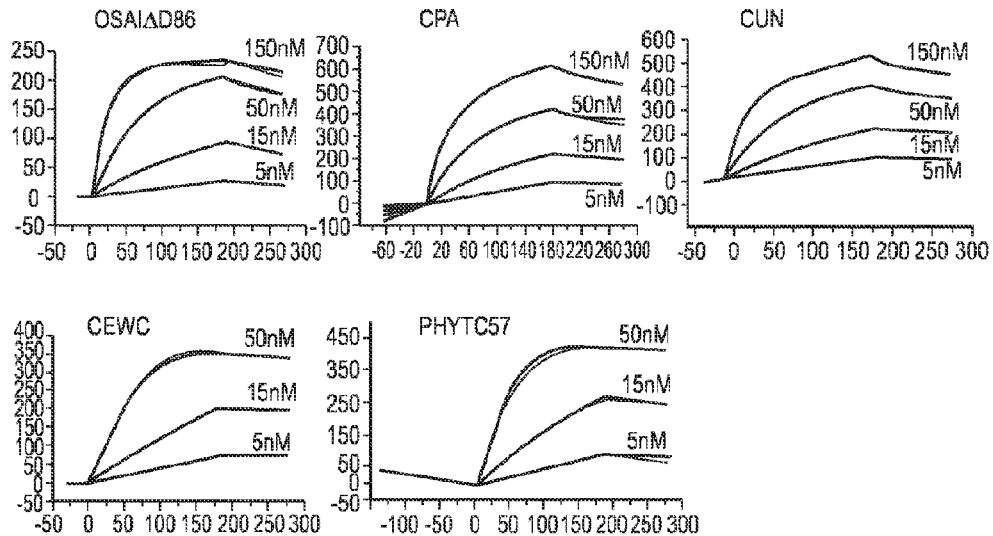

Enzyme assays with papain using the artificial substrate pGlu-Phe-Leu-p-nitroanilide confirmed that PHYTC57 was an active cysteine protease inhibitor. Ki values were not determined, but from the IC50 values for PHTYC57 and OSA-IΔD86 ($4.6 \times 10^{-8}$ M and $1.8 \times 10^{-7}$ M respectively) it is clear that PHYTC57 is a more potent inhibitor than OSA-IΔD86. To directly measure the interaction between the cystatins and protease we measured the binding kinetics using BIAcore surface plasmon resonance analysis. The cystatins were immobilised onto nickel coated sensor chips by the C-terminal His-tags. Papain was then allowed to bind to the immobilised cystatin and measurements were made at several papain concentrations. Sensorgrams for the binding of OSA-IΔD86, CPA, CUN, CEWC and PHYTC57 to papain are shown in FIG. 3. The data at each concentration were fitted to the Langmuir 1:1 binding model and the kinetic constants were determined. The data showed a good fit to the model consistent with the known 1:1 stoichiometry of cystatin inhibition of cysteine proteases. A summary of the kinetic constants for these cystatins is shown in Table 3. PHYTC57 displays higher association and lower dissociation kinetics compared with the naturally occurring cystatins tested, with an equilibrium constant $K_D$ of $6.3 \times 10^{-12}$ M, indicating a tight binding complex with papain. This value is two orders of magnitude lower than the $K_D$ value measured for chicken egg white cystatin ($3.9 \times 10^{-10}$ M), three orders of magnitude lower than the improved phytocystatin OSA-IΔD86 ($4.7 \times 10^{-9}$ M) and four orders of magnitude lower than the phytocystatins CUN ($1.4 \times 10^{-8}$ M) and CPA ($2 \times 10^{-8}$ M).

TABLE 3

Kinetic parameters determined by surface plasmon resonance. Association and dissociation rate constants ($K_a$ and $K_d$) and equilibrium constants ($K_A$ and $K_D$) are shown.

| | $K_a$ (1/M.s) | $K_d$ (1/s) | Chi$^2$ | $K_A$ (1/M) | $K_D$ (M) |
|---|---|---|---|---|---|
| OSAIΔD86 | $2.6 \times 10^5$ | $1.2 \times 10^3$ | 0.98 | $2.1 \times 10^8$ | $4.7 \times 10^{-9}$ |
| CUN | $2.6 \times 10^5$ | $3.5 \times 10^3$ | 2.3 | $7.3 \times 10^7$ | $1.4 \times 10^{-8}$ |
| CPA | $2.6 \times 10^5$ | $5.2 \times 10^3$ | 3.2 | $5.0 \times 10^7$ | $2.0 \times 20^{-8}$ |
| CEWC | $1.3 \times 10^6$ | $4.9 \times 10^4$ | 5.3 | $2.6 \times 10^9$ | $3.9 \times 10^{-10}$ |
| PHYTC57 | $3.5 \times 10^5$ | $2.2. \times 10^6$ | 13.9 | $1.6 \times 10^{11}$ | $6.3 \times 10^{-12}$ |

Phytocystatin Stability

Figure 4:
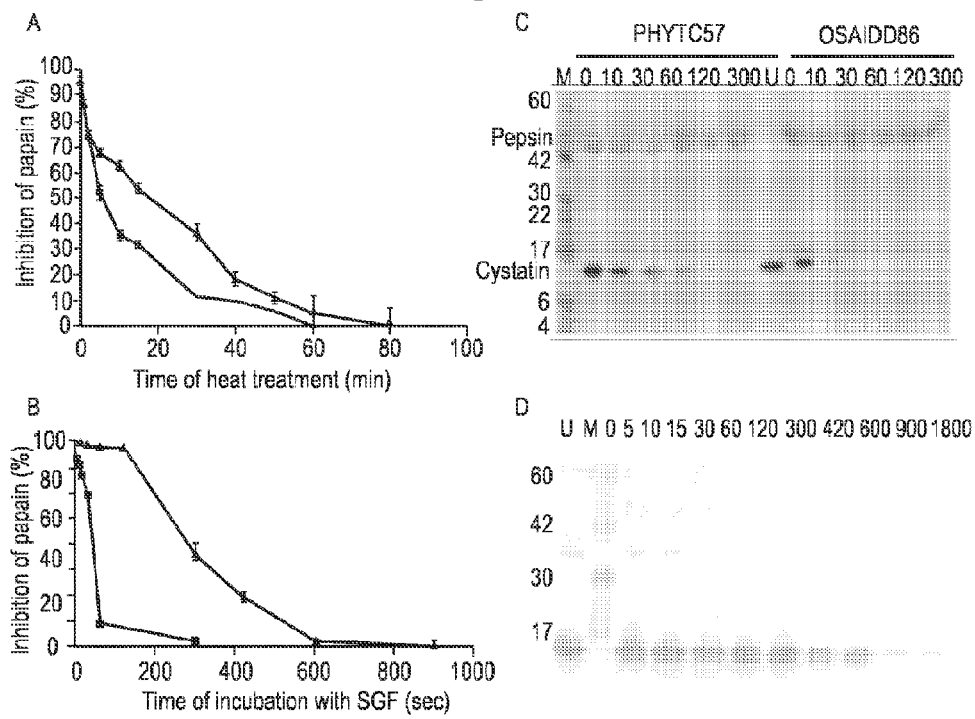

We were interested to explore whether PHYTC57 displayed greater stability when compared with a well-characterised parental phytocystain, OSA-IΔD86. Samples of these phytocystatins were incubated for various times in a boiling water bath, chilled and then tested for residual inhibitory activity in the papain assay (FIG. 4A). The consensus protein PHYTC57 displays greater thermostability (t½=17 min) than OSA-IΔD86 (t½=6 min) while inhibitory activity can still be detected at 80 min with PHYTC57 compared with only 58 min for OSA-IΔD86.

We also tested the stability of OSA-IΔD86 and PHYTC57 using a simulated gastric fluid (SGF) digestibility assay. The proteins were incubated for various times in freshly prepared SGF before neutralising the reaction. Samples were then analysed in two ways, by enzyme assays to determine the residual inhibitory activity (FIG. 4B) and by SDS-PAGE (FIG. 4C) to determine whether the protein was digested and. Enhanced stability of PHYTC57 was observed in the digestion studies with the PHYTC57 and OSA-IΔD86 displaying t % values of 260 sec and 30 sec respectively in enzyme assays. These assay data indicate that some 99% of OSA-IΔD86 is destroyed in the simulated gastric fluid between 30 and 60 seconds after incubation. For PHYTC57 this level of inactivation does not occur until between 2 and 5 minutes demonstrating that PHYTC57 is more resistant to the digestion conditions. The Coomassie stained SDS-PAGE results (FIG. 4C), which identify full-length protein, support these data with only trace OSA-IΔD86 present at 30 sec whereas for PHYTC57 some protein is still present at 120 sec. To confirm these results for PHYTC57 we analysed the SGF digestion products by western blot analysis using an anti-6His tag antibody. As shown in FIG. 4D this reveals that the majority of the protein has indeed been destroyed by 300 sec SGF treatment, although, trace amounts of intact PHYTC57 remain at 300 and even 420 sec treatment. If PHYTC57 was to be used for transgenic plant expression, the fact that the majority of full-length PHYTC57 protein and all inhibitory activity has been lost following a 10 min incubation in SGF would mean that PHYTC57 should be readily destroyed during the digestive process following any inadvertent host digestion.

DISCUSSION

The consensus approach to protein design provides a method to generate a sequence that does not exist in nature. Such a sequence should optimise the conserved functional sequence parameters of a family of homologous proteins. In particular critical residues that are involved in the structure and folding of the family are likely to be highly conserved (Lehmann and Wyss 2001; Main et al. 2003a; Main et al. 2003b; Main et al. 2005) (Forrer et al. 2004) (Steipe 2004). Depending upon the biological roles of individual members of the family, functional residues may or may not be conserved. In the case of the phytocystatins which show functional conservation in the form of cysteine protease binding and inhibition, there is a reinforcement of the highly conserved sequence motifs that are involved in interaction with the cysteine protease active site. The consensus approach should therefore give rise to an optimised protein in which the biological function, cysteine protease binding, as well as general stability are enhanced.

Plants contain a class of cystatins that have distinctive characteristics from animal cystatins and stefins, and plants do not contain stefins. In particular for the animal cystatins and stefins the N-terminal Gly sequence, is important for inhibition of cysteine proteases whilst this is not the case for plant cystatins [Abe, K. et al. (1988) J. Biol. Chem 263, 7655-7659]. In addition the plant cystatins contain a typical sequence [LVI][AGT][RKE][FY][AS][VI]X[EDQV] [HYFQ]N (SEQ ID NO 81) that is not found in other cystatins or in stefins.

SPR analysis of immobilised cystatins with papain revealed that PHYTC57 is more effective at forming and maintaining a protein:protein interaction complex with papain than are the 3 parental phytocystatins tested here. In particular the dissociation rate constant is reduced indicating that once bound, the PHYTC57:papain complex is more stable than those formed by the other cystatins tested. It has previously been reported that the animal-derived cystatins, which contain disulphide bonds are more efficient cystatins than characterised phytocystatins whose efficacy ranges from around 10 nM for OSA-I (Urwin et al. 1995) to pM for soybean cystatins (Koiwa et al. 2001) against papain. In our studies we observe that PHYTC57 is more effective at binding papain than the animal cystatin chicken egg white cystatin. In addition PHYTC57 displays enhanced thermal stability as well as greater stability in a simulated digestibility assay.

The fact that PHYTC57 displays enhanced properties does not mean that it could not be enhanced further. The reinforcement of the conserved motifs that comprise the binding region may represent the biologically optimal binding sequence, but perhaps not the most effective. For example, Koiwa demonstrated that alteration of the third loop region in soybean cystatins enhanced efficacy of the resulting variants (Koiwa et al. 2001). There has been a report that novel sequences within the QWAG (SEQ ID NO 83) region confer enhanced inhibitory activity (Melo et al. 2003). In terms of potential use in transgenic plant systems it is unlikely that further enhancements in stability would be beneficial due to the need to ensure that transgenic products do not accumulate in the environment.

Figure 5:
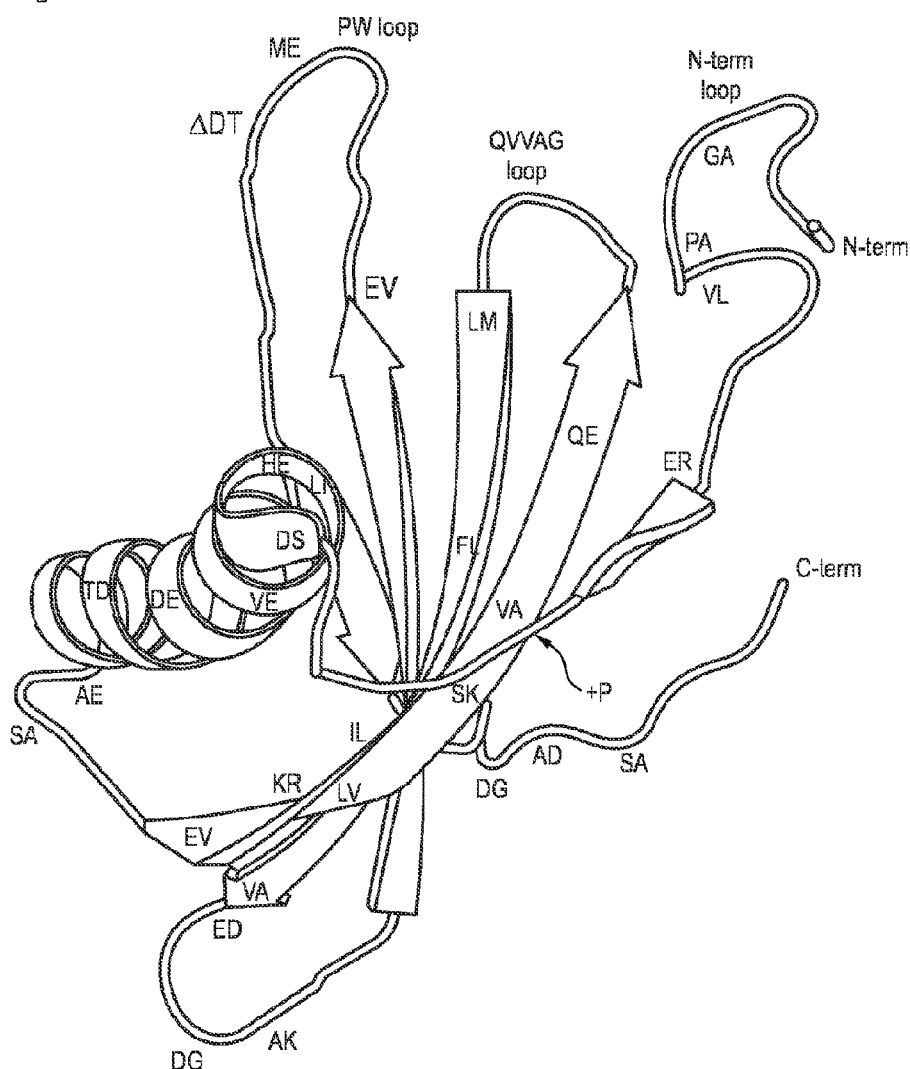

We have focussed here on the relative binding efficiency of PHYTC57 compared with OSA-IΔD86. This rice cystatin variant was the first enhanced phytocystatin generated and it has been subjected to a wide range of studies leading to transgenic plant expression and plant nematode resistance trials (Urwin et al. 1995; McPherson et al. 1997; Urwin et al. 1997; Urwin et al. 1998; Urwin et al. 2000; Urwin et al. 2001; Urwin et al. 2003; Lilley et al. 2004). PHYTC57 displays 34 amino acid differences from OSA-IΔD186. A comparison of the positions of these amino acids differences between OSA-IΔD86 and PHYTC57 is shown in FIG. 5 in which the substitutions are colour coded and represented upon the structural model for OSA-I (pdb code 1EQK) (Nagata et al. 2000). The differences are dispersed throughout the structural scaffold and include both conservative changes and non-conservative changes. It is interesting that 6 of the changes involve the introduction of negatively charged amino acids. Detailed comparative biochemical, sequence analysis and mutagenesis studies of individual parental cystatin molecules with the consensus protein could be undertaken to define the most critical "consensus" substitutions leading to enhanced properties, thus enhancing our understanding of protein structure-function relationships.

The surprisingly significant enhanced stability of PHTC57 led us to consider the potential for this small consensus protein as a new scaffold. Protein scaffolds for the selection of new binding functions are proving to be useful in a wide range of applications as replacements for antibodies (Skerra 2007) including in medical applications (Wurch, Pierre et al. 2012). An example of the development of a cystatin as a scaffold for peptide aptamer selection based on human stefin A has been reported (Woodman, Yeh et al. 2005). There has been a recent report of the development of an Fn3-like consensus protein from 15 fibronectin or tenascin Fn3-like domain sequences which is proposed as a potential scaffold (Jacobs, Diem et al. 2012). The naturally occurring Fn3 domain 10 is a well-studied scaffold developed by Koide and colleagues (Koide, Bailey et al. 1998; Karatan, Merguerian et al. 2004; Koide, Gilbreth et al. 2007). Due to its enhanced thermostability, small size and lack of cysteines we anticipate that the consensus PHYTC57 will prove useful as a binding protein scaffold for displaying variable peptide loop libraries for screening against a range of target molecules to identify novel artificial binding proteins.

PHYTC57 therefore offers potential benefits for transgenic plant defence schemes as an improved cysteine protease inhibitor targeted at pathogens such as plant nematodes, and for development as a scaffold protein for selecting new binding functionalities.

Creation of Scaffold Protein Library, Screening and Testing Function of 'Adhirons'

Introduction

The present inventors designed a novel artificial binding (scaffold) protein based on the consensus sequence of 57 plant-derived phytocystatins described above (termed PHYTC57 above, but referred to below as 'Adhiron'). This artificial protein meets all the requirements (small, monomeric, high solubility and high stability and the lack of disulphide bonds and glycosylation sites) to be a good scaffold for peptide presentation. We chose the WAG (SEQ ID NO 82) and the PWE regions of the Adhiron scaffold for peptide presentation with nine randomized positions in each loop.

Based on high yields of Adhiron scaffold expressed in *E. coli* we hypothesised that protein alterations within the two loops have a tolerable effect on the protein expression level and stability of the scaffold. Therefore our scaffold seems to be amenable for use in generating combinatorial libraries for screening with the phage display technology (Smith 1985). The success of phage displays system relies on the quality of the initial DNA library, which is mainly derived by its diversity. Improved library diversity can be achieved by using trinucleotide (trimer)-synthesized oligos (Kayushin, Korosteleva et al. 1996) which provide theoretically equal levels of introduction of the different amino acids as well as avoidance of stop codons and cysteine (Virnekas, Ge et al. 1994; Krumpe, Schumacher et al. 2007). Furthermore, trimer insertions or deletions will not lead to a shift in reading frame mutation thereby still producing potentially functional proteins. Therefore we have chosen a trimer mixture encoding the 19 naturally occurring amino acids excluding cysteine for the loop-randomised oligos.

Our work demonstrates that Adhirons have a high potential to play a key role in generating research reagents, diagnostics as well as therapeutics (drug discovery).

The Adhiron scaffold shows remarkably high thermal stability (Tm ca. 101° C.) above that reported for any other non-repeat scaffold protein, and can be expressed at high levels in prokaryotic expression systems to produce recombinant protein reproducibly. We have constructed a phage-display library based on the insertion of randomised amino acid sequences to replace residues at two loop regions within the Adhiron. The library has a complexity of approximately $3 \times 10^{10}$, with greater than 86% full length clones after phage production, indicating the very high quality of the library. As a demonstration of the efficacy of the library, the yeast Small Ubiquitin-like Modifier protein (SUMO) was screened to identify artificial binding protein (Adhiron) reagents capable of binding to this target protein. More than 20 individual Adhirons were identified that bind to yeast SUMO (ySUMO) as assessed by a phage enzyme-linked immunosorbent assay (ELISA). DNA sequencing indicated that the majority show partial sequence homology within one of the two loop regions to the known SUMO interactive motif (Val/Ile-X-Val/Ile-Val/Ile; where X is any amino acid). Four Adhiron coding regions were sub-cloned into the vector pET11 and recombinant protein was expressed, purified and tested in ELISA and Western blot analyses. The four Adhirons had low nanomolar affinities for ySUMO and showed high specificity to ySUMO with low level binding to human SUMO1 protein. Furthermore, we screened the Adhiron library against a number of other targets, namely fibroblast growth factor (FGF1), platelet endothelial cell adhesion molecule (PECAM-1), also known as cluster of differentiation 31 (CD31), and a 10 amino acid peptide with a cysteine on the N-terminus for thiol linkage to biotin (Cys-Thr-His-Asp-Leu-Tyr-Met-Ile-Met-Arg-Glu, SEQ ID NO 84) and also identified Adhirons against these targets as confirmed by phage ELISA. We have, therefore, developed a versatile, highly stable and well expressed scaffold protein, termed Adhiron, that is capable of displaying randomised peptide loops and we have demonstrated the ability to select highly specific, high affinity binding reagents from an Adhiron library against a range of targets for use in multiple applications.

Materials and Methods

Construction of Adhiron Library

A consensus sequence derived from alignment of 57 phyocystatin sequences was identified as described above and a codon-modified gene designed for expression in *E. coli* was synthesised (GenScript). The Adhiron scaffold coding region and Adhiron library coding regions were cloned between NheI and NotI restriction sites to create a fusion coding region with the 3' half of the gene III of bacteriophage M13 in a phagemid vector pBSTG1, a derivative of pDHisII which is derived from pHEN1 (Hoogenboom, Griffiths et al. 1991) and which also contains a DsbA signal peptide (pBSTG1-DsbA-Adhiron). The library was constructed by splice overlap extension (SOE) of two PCR products (Horton, Cai et al. 1990) and all primers were synthesised by Ella Biotech.

The first PCR product extended from the DsbA coding sequence to the first inserted loop and was generated by the primers:

```
                                       (SEQ ID NO 21)
Forward primer 5' - TCTGGCGTTTTCTGCGTC - 3', (SEQ ID NO 22)
Reverse primer 5' - CTGTTCTTTCGCTTTAACAAC - 3'.
```

The second PCR product introduced two nine amino acid loop regions into the scaffold protein at loop 1 and loop 2 by using the following primers. The PstI site used for cloning is underscored:

```
Forward loop                           (SEQ ID NO 23)
5'GTTGTTAAAGCGAAAGAACAGNNNNNNNNNNNNNNNNNNNNNNNNNNN

NACCATGTACCACTTGACCCTG-3',

Reverse loop                           (SEQ ID NO 24)
5'CTGCGGAACTCCTGCAGTTCTTTGAAGTTNNNNNNNNNNNNNNNNNN

NNNNNNNNNCTTAACCCAAACTTTCGCTTCG-3'.
```

The degenerate positions (NNN) were introduced as trimers representing a single codon for each of the 19 amino acids excluding cysteine and there were no termination codons. The primers were also designed to introduce NheI (forward) and PstI (reverse) restriction sites to facilitate cloning into the pBSTG1 phagemid vector that contains an in-frame amber stop codon to allow translational read through to create an Adhiron-truncated pIII fusion protein. PCR was performed using Phusion High Fidelity Polymerase (NEB) at 98° C. for 5 minutes followed by 20 cycles of 98° C., 10 sec; 56° C., 15 sec; 72° C., 15 sec followed by 72° C. for 5 minutes. PCR products were purified by gel extraction (Qiagen), and used for SOEing with 10 cycles using the protocol above. The PCR product was digested with NheI and PstI and was gel extracted then cloned into the pBSTG1-Adhiron phagemid that had also been digested with NheI and PstI to leave the DsbA signal sequence and C-terminal coding region of the Adhiron, to generate the DNA based Adhiron library. Electroporation was used to introduce the ligated library products into *E. coli* ER2738 electrocompetent cells (Lucigen). In total 20 mL of ER2738 cells were electroporated with 50 ng of library DNA per 50 ul of ER2738 cells. Cells were allowed to recover for 1 hr in 2TY medium and were then grown at 37° C., 225 rpm to an $OD_{600}$ of 0.6 in 2 liters of 2TY medium. 1 μl M13KO7 helper phage (NEB) ($10^{14}$/ml) were added and allowed to infect the cells with shaking at 90 rpm for 1 hr, and then the culture was allowed to produce phage particles overnight at 25° C. in the presence of kanamycin (50 μg/ml). The phage were precipitated with 6% polyethylene glycol 8000 and 0.3 M NaCl, and suspended in 50% glycerol for storage. Library size was determined to be ~$3\times10^{10}$ with a minimal vector only background.

Target Preparation and Phage Display

The following protocols are described for yeast SUMO but an identical protocol was used for the screening or other targets. Yeast SUMO (ySUMO) protein was expressed in BL21 (DE3) cells using IPTG induction and purified by Ni-NTA resin (Qiagen) affinity chromatography according to the manufacturer's instructions. Purity was confirmed by SDS-PAGE. Yeast SUMO was biotinylated using EZ-link NHS-SS-biotin (Pierce), according to the manufacturer's instructions. Biotinylation was confirmed using streptavidin conjugated to horse radish peroxidase (HRP) to detect the biotin on ySUMO absorbed onto Immuno 96 Microwell™ Nunc MaxiSorp™ (Nunc) plates. Phage display library biopanning was performed as follows:

5 μl of the phagemid library, containing $10^{12}$ phagemid particles, was mixed with 95 μl phosphate buffer saline, 0.1% Tween-20 (PBST) and pre-panned three times in high binding capacity streptavidin coated wells (Pierce) for a total of 1 hour. 100 μl of 100 nM biotinylated ySUMO was added to the panning well for 1 hour with shaking on a Heidolph VIBRAMAX 100 at speed setting 3 prior to adding the pre-panned phage for 2.5 hours also on the vibrating platform. Panning wells were washed 10 times in 300 μl PBST using a plate washer (Tecan Hydroflex), and eluted with 100 μl of 50 mM glycine-HCl (pH 2.2) for 10 minutes, neutralised with 1 M Tris-HCL (pH 9.1), and further eluted with 100 μl of triethlyamine 100 mM for 6 minutes and neutralised with 50 μl of 1M Tris-HCl (pH 7). Eluted phage were incubated with exponentially growing ER2738 cells ($OD_{600}$=0.6) for 1 hr at 37° C. and 90 rpm. Cells were plated onto Lysogeny Broth agar plates supplemented with 100 μg/ml carbenicillin and grown at room temperature overnight. The next day, the colonies were scraped into 5 ml of 2TY medium and inoculated into 25 ml of 2TY medium supplemented with carbenicillin (100 μg/ml) to reach an $OD_{600}$ of 0.2, incubated at 37° C., 225 rpm for 1 hr and infected with ca.$1\times10^9$ M13KO7 helper phage. After 1 hr incubation at 90 rpm, kanamycin was added to 25 μg/ml, cells were incubated overnight at 25° C. at 170 rpm, and phage were precipitated with 6% polyethylene glycol 8000, 0.3M NaCl and resuspended in 1 ml of 10 mM Tris, pH 8.0, 1 mM EDTA (TE buffer). 2 μl of this phage suspension was used for the second round of selection. This time phage display was performed using streptavidin magnetic beads (Invitrogen). Phage were pre-panned with 10 μl of washed beads for 1 hr on a Stuart SB2 fixed speed rotator (20 rpm), and 10 μl of beads were labelled with 100 μl of 100 nM biotinylated ySUMO for four hours on the same rotator. Yeast SUMO labelled beads were washed three times in PBST prior to adding the pre-panned phage for 1 hr. Beads were washed 5 times in PBST using a magnet to separate beads from solution after each washe, then eluted and amplified as above. The final pan was performed using neutravidin high binding capacity plates (Pierce), as previously described for the first panning round, but this time the phage were eluted using 100 μl 100 mM dithiothreitol (DTT) on a vibrating platform for 20 min prior to infection of ER2738 cells. Phage were recovered from wells containing target protein and controls wells to determine the level of amplification in target wells.

Phage ELISA

Individual ER2738 colonies from the final pan were picked and grown in 100 μl of 2TY with 100 μg/ml of carbenicillin in a 96 deep well plate at 37° C. (900 rpm) for 6 hr. 25 μl of the culture was added to 200 μl of 2TY containing carbenicillin and grown at 37° C. (900 rpm) for 1 hr. M13K07 helper phage (10 μl of $10^{11}$/ml) were added, followed by kanamycin to 25 μg/ml and the bacteria were grown overnight at 25° C. (450 rpm). Streptavidin coated plates (Pierce) were blocked with 2x casein blocking buffer (Sigma) overnight at 37° C. The following day the plates were labelled with 0.4 nM of biotinylated yeast SUMO for 1 hr, the bacteria were collected by centrifugation at 3000 rpm for 5 min and 45 μl of growth medium containing the phage was added to wells containing biotinylated yeast SUMO or a well containing the biotinylated linker and incubated for 1 hr. Wells were washed using a Tecan Hydroflex plate washer 3 times in 300 μl PBST, and a 1:1000 dilution of HRP-conjugated anti-phage antibody (Seramun) in 100 μl PBST was added for 1 hr. Wells were washed 10 times in 300 μl PBST and binding was visualised with 100 μl 3,3',5,5'-Tetramethylbenzidine (TMB) liquid substrate (Seramun) and measured at 560 nm.

Adhiron Protein Production

The DNA coding sequences of Adhirons that bound to yeast SUMO were amplified by PCR, the product was restriction digested with NheI and PstI and cloned into pET11a containing the Adhiron scaffold and digested with the same restriction sites. Colonies were picked and grown overnight in 5 ml LB medium at 37° C., 225 rpm and plasmid DNA was purified as minipreps (Qiagen) and sequenced to confirm the presence of the correct insert. Plasmids were transformed into BL21 (DE3) cells by heat shock and colonies were grown overnight at 37° C. The following day the culture was added to 400 ml of LB medium, grown to an $OD_{600}$ of 0.6 at 250 rpm at 37° C. and isopropyl β-D-1-thiogalactopyranoside (IPTG) was added to 1 mM final concentration. Cells were grown for a further 6 hr, harvested by centrifugation at 3000 g and re-suspended in 25 ml of 1× Bugbuster (Novagen). Benzonase was added according to the manufacturer's instructions and the suspension was mixed at room temperature for 20 minutes, heated to 50° C. for 20 minutes and centrifuged for 20 minutes at 9400×g. The cleared supernatant was mixed with Ni-NTA resin 500 μl of slurry for 1 hr, washed 3 times in 30 ml wash buffer (50 mM PBS, 500 mM NaCl, 20 mM imidazole, pH 7.4) and eluted in 1 ml of elution buffer (50 mM PBS, 500 mM NaCl, 300 mM imidazole, pH 7.4). 100 μg of the SUMO binding Adhirons (Ad-ySUMO) were biotinylated using NHS SS-biotin (Pierce) according the manufacturer's instructions for use in ELISAs and Western blotting.

ELISA Analysis 5 ng (unless otherwise indicated) of target protein in PBS was absorbed on to Immuno 96 Microwell™ Nunc MaxiSorp™ plate wells overnight at 4° C. The next day 200 μl of 3× blocking buffer was added to the wells and incubated at 37° C. for 4 hours with no shaking. Biotinylated yeast SUMO binding Adhirons at 100 μg/ml were diluted 1:1000 in PBST containing 2× blocking buffer and 50 μl aliquots were incubated in target wells for 1 hr with shaking. Wells were washed 3× in 300 μl PBST, and streptavidin conjugated to horse radish peroxidase (HRP) (Invitrogen) diluted 1:1000 in 50 μl PBST was added to the wells for 1 hr. Wells were washed 6× in 300 μl PBST and binding was visualised with 50 μl TMB liquid substrate and the absorbance measured at 560 nm.

Western Blot Analysis

Target protein or target protein mixed with HEK293 cell lysate (20 μg) was mixed with loading buffer (Laemmli, 60 mM Tris-Cl pH 6.8, 2% SDS, 10% glycerol, 5% β-mercaptoethanol, 0.01% bromophenol blue), boiled for 3 min, centrifuged for 1 min at 15,000×g and then resolved in a 15% SDS-polyacrylamide gel. Proteins were transferred to PVDF membranes for 45 minutes at 4 Watts (Amersham Biosciences) and incubated for 1 hr in blocking buffer (5% BSA in PBS 0.1% Tween) followed by incubation for 1 hr with Ad-ySUMO (100 μg/ml diluted 1:1000 PBST). Bound Ad-ySUMOs were detected using streptavidin conjugated HRP and chemiluminescence (ECL Plus kit, Amersham).

Protein-Protein Interaction Affinity Measurement

The BLitz™ (ForteBio) dip and read streptavidin biosensors were used to estimate affinity of binding of the biotinylated Ad-ySUMO binders, according to the manufacturer's instructions. In brief, at least 4 readings at different ySUMO concentrations (0.25 mM-1 mM), were used to measure the affinity of each Ad-ySUMO. A global fit was used to calculate the affinity of each Ad-ySUMO. These readings were comparable to affinities measures made using a Biacore surface plasmon resonance instrument.

Results

Adhiron Design and Phage Display

The Adhiron gene was originally designed to create a more potent protease inhibitor, however, due to its potential as a scaffold protein for presenting constrained peptide regions for molecular recognition (FIG. 6A) we decided to investigate its use as such a scaffold. The gene sequence was codon optimised to enhance expression in an *E. coli* expression system (FIG. 6B). Restriction sites were introduced to facilitate cloning of the gene into the pBSTG1 phagemid vector to allow in-frame translational read through of an amber stop codon to allow an Adhiron-truncated pIII fusion protein to be produced when expressed in non-suppressor cells such as ER2738 cells but to allow production of the Adhiron only in suppressor cells such as JM83. The Adhiron pIII fusion protein was expressed from the phagemid vector pBSTG1, while the other components to allow replication and packaging of the phagemid DNA into M13 phage particles were introduced using M13KO7 helper phage. Expression of the Adhiron-pIII fusion protein was confirmed by Western blot analysis using an anti-pIII antibody. The thermal stability of the Adhiron scaffold was tested by differential scanning calorimetry, which showed a melting temperature of 101° C. (FIG. 7A). The structural integrity of the consensus sequence was examined using circular dichroism, which demonstrated a high ratio of beta sheet to alpha helix and random coil (FIG. 7B).

We then compared the thermal stability by differential scanning calorimetry of the Adhiron scaffold (FIG. 8A) with a representative small soluble well characterised protein, lysozyme (FIG. 8B) which shows that lysozyme is significantly less stable (Tm ca. 65° C.) than the Adhiron. We then tested an Adhiron selected to bind to a myc antibody, the addition of the loops into the scaffold reduces the Tm to 85° C. but this still represents a higher melting temperature than most scaffold proteins. This Adhiron protein can undergo repeated cycles of denaturation and renaturation as shown by the series of scans (FIG. 8C).

Library Design

Figure 6:
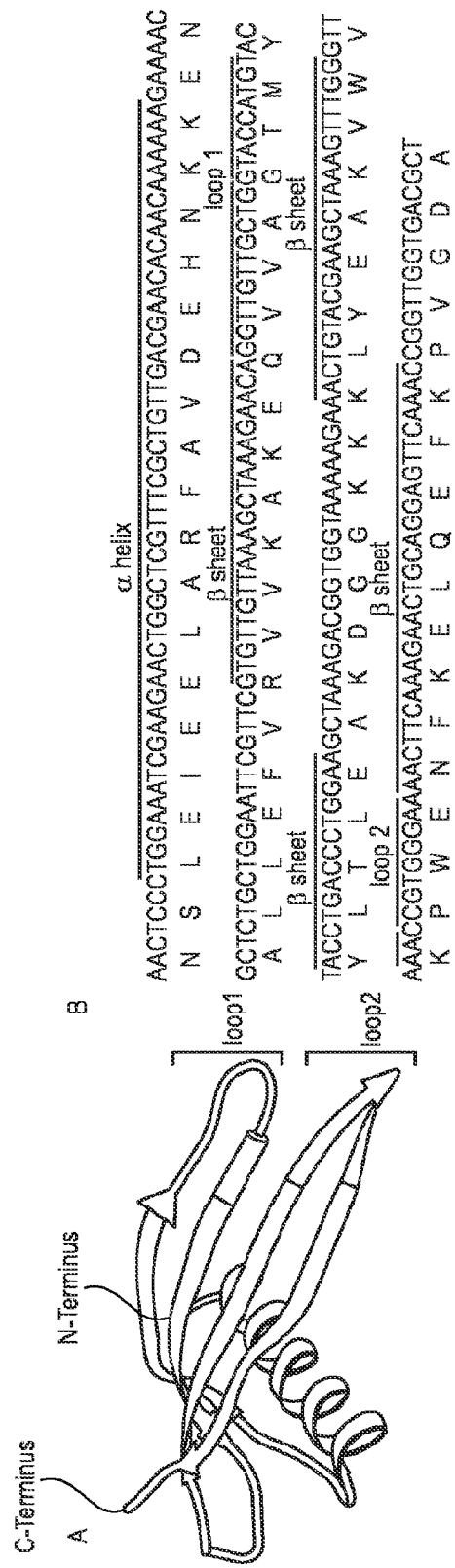
Figure 7:
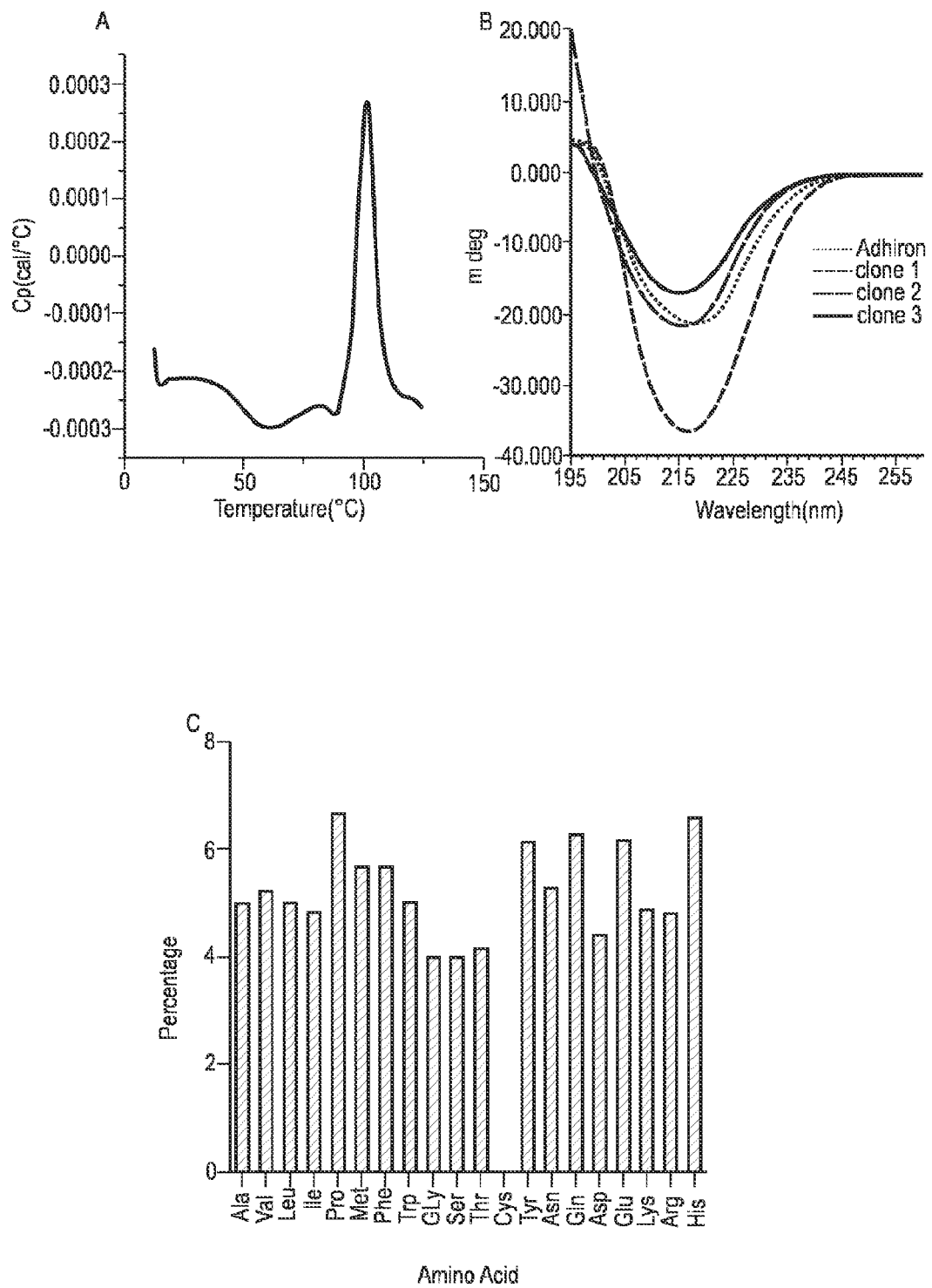

The introduction of peptide encoding sequences suitable for molecular recognition was guided by the predicted loop positions within the structure of the Adhiron (FIG. 6). Loop1 was positioned between the first and second beta strands and loop2 was positioned between the third and fourth beta strands. Sequences comprising nine random amino acids (excluding cysteine) were introduced at both loop positions replacing four and three amino acids in loop1 and loop2, respectively. To determine if extension of these loop regions disrupts the structure of the Adhiron three individual Adhirons with loop insertions were isolated, expressed and examined by circular dichroism (FIG. 7B). All three clones maintained a high proportion of beta structure, with one clone displaying an increase in beta structure content likely indicating extension of the beta strands into the new loop regions. This demonstrates that loop insertion does not affect the structure of the scaffold. We generated a phage display library of complexity approximately $3 \times 10^{10}$. To check the amino acid composition, 96 clones were isolated from ER2738 cells infected with the library. We examined the sequence of phage clones to determine any bias in amino acid composition or other undesirable consequences introduced during phage production (FIG. 7C). No bias in amino acid distribution was observed. 86.5% clones were full-length variants while 3.1% of clones were the Adhiron scaffold with no inserts, and 10.4% of the clones showed frame shifts and so were likely of no value in the library. This very high proportion of full-length coding sequences at the level of the phage genome demonstrates the high quality of the library generated.

Library Screening

Figure 9:
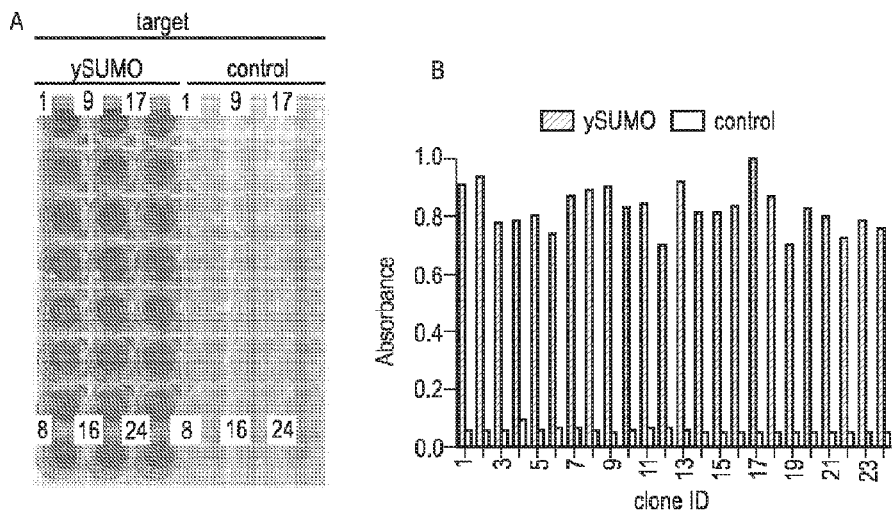

Library screening was performed initially using yeast SUMO as the target. Yeast SUMO was biotinylated to allow immobilisation of the protein via avidin binding proteins and to ensure that the target was not adsorbed directly onto plastic or particle surfaces which can sometimes lead to denaturation of the target protein. This ensures that the target protein maintains its three dimensional structure allowing for the selection of binding proteins that recognise either linear, or conformational epitopes. Over 1000-fold amplification in colony recovery was observed compared to control samples by panning round three. Twenty four clones were isolated and their ability to bind to the SUMO target was confirmed by phage ELISA (FIG. 9). All clones tested showed strong binding to yeast SUMO with little or no binding to the control wells demonstrating the specificity of the Adhirons. The clones were sequenced, which identified 22 distinct Adhirons and the sequences of the loop regions in these clones is shown in Table 4.

TABLE 4

Showing the two loop sequences for the 24 Ad-ySUMO binders identified from the screen.

| Ad-ySUMO | Loop1 (SEQ ID No) | Loop2 (SEQ ID No) |
|---|---|---|
| 1 | WDLTGNVDT (25) | WDDWGERFW (49) |
| 2 | IDLTNSFAS (26) | DINQYWHSM (50) |
| 3 | INLMMVSPM (27) | GIQQNPSHA (51) |
| 4 | IDLTHSLNY (28) | GLTNEIQKM (52) |
| 5 | IDLTHSLNY (29) | GLTNEIQKM (53) |
| 6 | IDLTEWQDR (30) | PEPIHSHHS (54) |
| 7 | WVDMDYYWR (31) | MDEIWAEYA (55) |
| 8 | IDLTQTEIV (32) | EPGIIPIVH (56) |
| 9 | IDLTDVWID (33) | GLMTQTNSM (57) |
| 10 | IIIHENDAD (34) | GIMDGLNKY (58) |
| 11 | WILNNTQFI (35) | VLEGPDRWTV (59) |
| 12 | WYERSENWD (36) | RDYGFTLVP (60) |
| 13 | WDLTTPINI (37) | YEDYQTPMY (61) |
| 14 | WFDDEYDWI (38) | DYAATDLYW (62) |
| 15 | IDLTQPHDS (39) | YEEDEYWRM (63) |
| 16 | IDLTQSFDM (40) | PIDSNFTGT (64) |
| 17 | WYLLDVMDD (41) | HDRRYKQAE (65) |
| 18 | WIDRGQYWD (42) | IHNGYTIMD (66) |
| 19 | WSEADNDWH (43) | LDLETWQHF (67) |
| 20 | IDLTGQWLF (44) | PLWQYDAQY (68) |
| 21 | IDLTQSFDM (45) | PSHHNYQTM (69) |
| 22 | IDLTQSFDM (46) | PIDSNFTGT (70) |
| 23 | IDLTQPHDS (47) | PHDELNWNM (71) |
| 24 | WEDFQTHWE (48) | DVGQLLSGI (72) |

Clones 4 and 5 are identical and clones 16 and 22 are also identical. Interestingly clones 15 and 23, as well as 21 and 22 contain the same amino acid sequence in loop1 but different sequences in loop2. This sequence variation further supports the complex nature of the library. Analysis of the sequences identified a commonly occurring sequence of IDLT in positions 1 to 4 of loop1 in 12 of the clones indicating that this may be an important motif in binding to at least one epitope on the ySUMO. Also either a P or G in position occurs at position 1 of the second loop in 9 distinct clones and a P or G occurs in a position within residues 2 to 5 in another 6 clones potentially indicating that some structural feature may be important in binding. Interestingly the IDLT motif is similar to the human SUMO1 binding site of the MEF2 E3 ligase PIASx (VDV<u>IDLT</u>—SEQ ID NO 73) (Song, Durrin et al. 2004; Song, Zhang et al. 2005). Four clones were selected for further characterisation; clones 15 and 22 as this loop1 sequence occurred more than once, clone 20 as it also contained the IDLT motif and clone 10 as it contained a distinct motif in loop1.

Characterisation of the Adhiron-ySUMO (Ad-YSUMO) Proteins

Figure 10:
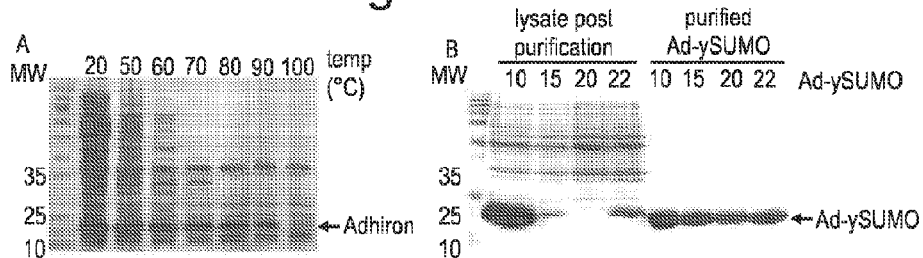
Figure 10:
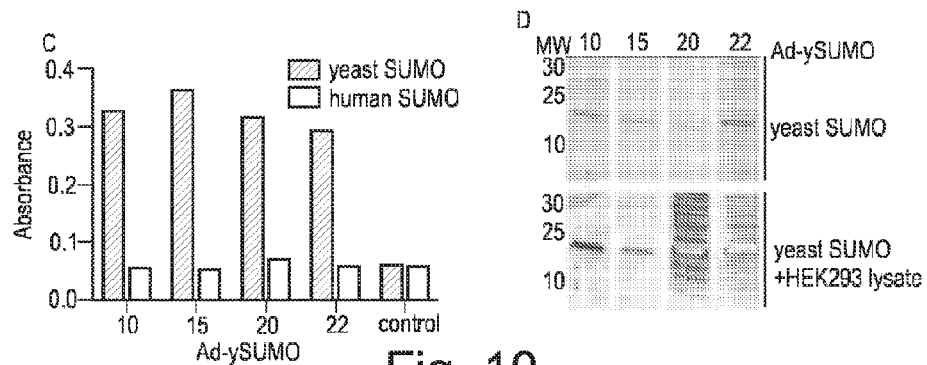

Due to the high thermal stability of the Adhiron scaffold (FIG. 7A) we predicted that to aid purification it should be possible to heat denature and precipitate the majority if *E. coli* proteins without affecting the integrity of the expressed Adhirons. To test this we heated lysates for 20 minutes at 50° C., 60° C., 70° C., 80° C., 90° C. and 100° C. centrifuged to pellet the denatured protein and analysed the supernatants by SDS-PAGE (FIG. 10A). Heating the lysate dramatically decreased the quantity of bacterial protein in the supernatant but did not significantly reduce Adhiron levels. A temperature of 50° C. was suitable to precipitate the majority of bacterial proteins and so was adopted in future studies. FIG. 9B demonstrates that the purified Ad-ySUMOs show high purity using a batch metal affinity purification method and that in some samples such as clone 10, the majority, of the protein was not isolated, potentially due to the limiting amount of the resin used during this purification. The estimated level of protein expressed was approximately 100 mg/L. The affinities of the Adhirons were estimated by using BioLayer Interferometry with BLitz™ (ForteBio) dip and read biosensors. The affinities were 11.5, 2.4, 14.2, and 9.0 nM for Ad-ySUMO10, 15, 20 and 22, respectively. These values are in line with affinities normally seen for good antibodies.

To further evaluate the use of the Adhirons as research reagents the Ad-ySUMOs were biotinylated and used in ELISA (FIG. 10C) and Western blot analysis (FIG. 10D). The Ad-ySUMOs bind to yeast SUMO but not to human SUMO1 (data not shown for SUMO1 Western blots) (n=3). To determine the specificity of the reagents, yeast SUMO was mixed with HEK293 cell lysates. Interestingly, Ad-ySUMO10 and 15 show specific binding to yeast SUMO with no binding to other proteins but Ad-ySUMO20 and 22 bind to many proteins in the lysates by Western blotting (n=3).

Further Example Screens

Figure 11:
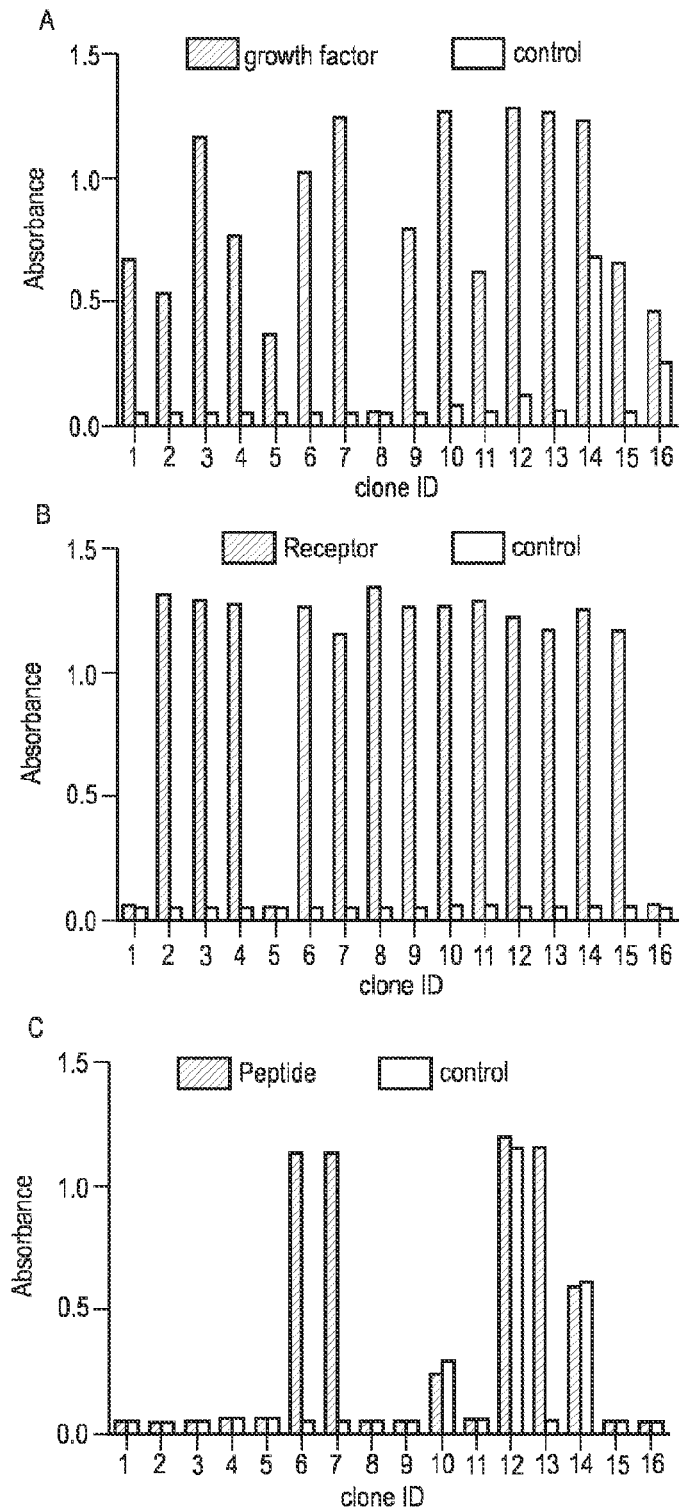

To further evaluate the ability of the Adhiron library to identify specific reagents capable of binding to a range of targets we screened against a growth factor (FGF1), a receptor (CD31), and a peptide sequence. All screens were performed over three panning rounds. Phage ELISA was used to examine the ability of Adhirons to bind to the corresponding target (FIG. 11). Interestingly, the majority of the clones tested for FGF1 and CD31 showed specific binding, whereas only three clones from the peptide screen showed specific binding. Further panning rounds against the peptide increased the ratio of hits to background so that 80% of the clones picked showed binding to target. This result is not unexpected due to the small size and limited likelihood of appropriate epitope presentation of the peptide compared to the larger and therefore potentially multiple epitope sites of the proteins.

To confirm that expressed Adhirons bind to their targets we have used the BlitZ™ to analyse three distinct recombinant Adhirons for both CD31 and the peptide target. The Adhirons were expressed and purified as soluble proteins. The $K_D$ values for CD31 Adhirons ranged from $8.5 \times 10^{-8}$ to $6.8 \times 10^{-9}$ M while those for the peptide ranged from $3.3 \times 10^{-8}$ to $3.5 \times 10^{-8}$.

Additionally, as shown in FIG. 25 we have identified Adhirons that bind to an organic molecule, posaconazole, Adhiron Crystal Structure FIG. 17 shows the crystal structure of an Adhiron complexed with a FcgRIIIa receptor domain. This reveals the 3D structure of the Adhiron showing the key structural elements of 4 beta strands and an alpha helix. The structure is unexpected in terms of a more compact nature and an apparently less twisted structure than is seen for X-ray structures of other cystatins, including for example stefin A. It is interesting that the beta structure extends into the loop regions to varying degrees.

The importance of displaying two randomised loops for selection of binding molecules for at least some targets is highlighted in this structure by the intimate interaction of both loops with the receptor protein. These loops correspond to LOOP1 and LOOP2 described in more detail below.

DISCUSSION

We have developed a new scaffold protein based on a consensus design of plant cystatin proteins, termed Adhiron, and which displays an extremely high thermal stability with a Tm of 101° C. This scaffold has been used to produce libraries by the introduction of two 9 amino acid variable regions. These variable sequences were encoded by oligonucleotides in which the variable positions are a subset of trimers comprising a single codon for each amino acid with the exception of cysteine. This resulted in a very similar distribution of each amino acid within the library. The library was of very high quality with 86.5% of clones representing full length variant clones.

The library was configured in a filamentous phage display format as a truncated gp3 fusion and has been screened against various target proteins. Analysis of Adhirons identified by screening against yeast SUMO revealed a number of proteins with distinct sequences in their variable regions. In some cases there are similarities which implies binding to the same site on the SUMO, whereas other clones do not show sequence conservation. All clones bind to ySUMO and not to a range of control proteins, indicating specificity. We have also identified Adhirons that bind specifically to a growth factor, human FGF1, a human receptor protein domain from CD31, a peptide and an organic compound. The ability to select binders against organic compounds as well as wide range of proteins is an important finding as most scaffolds have structural features that favour particular classes of target molecules.

The Adhirons can be conveniently purified by the inclusion of a temperature step at 50° C. which denatures many of the endogenous E. coli host proteins, thus enhancing the efficiency of affinity purification of the Adhiron. The X-ray structure of a complex of an Adhiron that binds to the human FcgRIII receptor provides useful information not only on the complex but also on the Adhiron protein and reveals a more compact and largely beta structure that supports the CD data. The compact nature of the scaffold, which is more pronounced than seen in other structures of stefins or cystatins seems likely to contribute to its high thermal stability. The interaction interface revealed by the X-ray structure indicates that both loop regions are involved in the interaction with the receptor domain.

The demonstration of successful and high quality libraries based on this highly stable, small and easily purified scaffold coupled with our robust and effective strategy for screening against a range of proteins makes our Adhiron library a valuable and novel resource for the development of reagents for a wide range of scientific, medical and commercial applications.

Variants of Adhirons

Variants of the Adhiron scaffold have been produced. The sequence shown in SEQ ID NO 1 and FIG. 6 is for the shortest version Adhiron examined, and comprises 81 residues in length before addition of further functional sequences such as a linker and His-tag or other sequences. However, two longer scaffold proteins have also been produced (SEQ ID NO 2 and 3), and each may be preferable in certain circumstances. It is possible that further deletion from the scaffold may be possible, but it is believed that SEQ ID NO 1, or variants thereof, are near to the optimum minimal length without stability of the scaffold protein being unduly compromised.

Full length 'Adhiron 92' (92 aa) has the following sequence (which consists of the scaffold sequence SEQ ID NO 3 plus a linker and His-tag, which are underlined):

(SEQ ID NO 74)
ATGVRAVPGN ENSLEIEELA RFAVDEHNKK ENALLEFVRV

VKAKEQVVAG TMYYLTLEAK DGGKKKLYEA KVWVKPWENF

KELQEFKPVG DA AAAHHHHHH

Short Adhiron 84' (84 aa) has the following sequence (which consists of the scaffold sequence SEQ ID No 2 plus a linker and His-tag, which are underlined):

(SEQ ID NO 75)
GNENSLEIEE LARFAVDEHN KKENALLEFV RVVKAKEQVV

AGTMYYLTLE AKDGGKKKLY EAKVWVKPWE NFKELQEFKP

VGDA AAAHHHHHH

Shortest Adhiron 81' (81 aa), which is shown in FIG. 6, has the following sequence (which consists of the scaffold sequence SEQ ID No 1 plus a linker and His-tag, which are underlined):

(SEQ ID NO 76)
NSLEIEELAR FAVDEHNKKE NALLEFVRVV KAKEQVVAGT

MYYLTLEAKD GGKKKLYEAK VWVKPWENFK ELQEFKPVGD

A AAAHHHHHH

The underlined sequence comprises an additional 3 Ala linker and 6 His detection/purification tag. This tag is not part of the scaffold per se, but is a useful addition to the protein for obvious reasons.

Specific Examples of Adhirons for Libraries

Exemplary Adhiron sequences which are useful for preparing scaffold protein libraries, i.e. libraries in which a variety of peptides have been inserted into the scaffold, are as follows:

Adhiron 92 (Sequence Shown Includes and Additional Met, Linker and Tag)

(SEQ ID NO 77)
M*ATG*VRAVPGNENSLEIEELARFAVDEHNKKENALLEFVRVVKAKEQ

*VVAG*TMYYLTLEAKDGGKKKLYEAKVWVK*PWE*NFKELQEFKPVGDA

AAAHHHHHH

One or more of the following modifications can be/have been made:
- An additional methionine residue (in bold) has been added at the N-terminus to facilitate translation.
- An N-terminal portion is located at amino acid residues 2-4 (in bold and italics), and suitably these 3 amino acids are replaced by an insert of typically from 3 up to about 20 amino acids.
- LOOP1 is located at amino acid residues 47-50 (numbered to exclude the N-terminal met) (in bold and italics), and suitably these 4 amino acids can be replaced by an insert of typically from 4 up to about 20 amino acids. A loop length of from 5 to 13 amino acids is preferred, and it is believed that a loop length of 9 amino acids is optimal.
- LOOP2 is located at amino acid residues 76-78 (numbered to exclude the N-terminal met) (in bold and italics), and suitably these 3 amino acids can be replaced by an insert of an insert of typically from 3 up to about 20 amino acids. A loop length of from 5 to 13 amino acids is preferred, and it is believed that a loop length of 9 amino acids is optimal.
- A C-terminal linker and His-tag is present. The length and composition of the linker can be varied, and the tag could of course be adapted to any suitable purification system.

Adhiron 84 (Sequence Shown Includes and Additional Met, Linker and Tag)

(SEQ ID NO 77)
MGNENSLEIEELARFAVDEHNKKENALLEFVRVVKAKEQ*VVAG*TMYYLT

LEAKDGGKKKLYEAKVWVK*PWE*NFKELQEFKPVGDA AAAHHHHHH

One or more of the following modifications can/have be made:
- An additional methionine residue (in bold) has been added at the N-terminus to facilitate translation.
- An N-terminal peptide sequence can be added to the N-terminus of the Adhiron (i.e. between the methionine residue and the first glycine as shown above), and this addition can be typically from 3 up to about 20 amino acids.
- LOOP1 is located at amino acid residues 39-42 (numbered to exclude the N-terminal met) (shown in bold and italics), and suitably these 4 amino acids can be replaced by an insert of typically from 4 up to about 20 amino acids. A loop length of from 5 to 13 amino acids is preferred, and it is believed that a loop length of 9 amino acids is optimal.
- LOOP2 is located at amino acid residues 68-70 (numbered to exclude the N-terminal met) (shown in bold and italics), and suitably these 3 amino acids can be replaced by an insert of typically from 3 up to about 20 amino acids. A loop length of from 5 to 13 amino acids is preferred, and it is believed that a loop length of 9 amino acids is optimal.
- A C-terminal linker and His-tag is present. The length and composition of the linker can be varied, and the tag could of course be adapted to any suitable purification system.

Adhiron 81 (Excludes the Met)

(SEQ ID NO 78)
MNSLEIEELARFAVDEHNKKENALLEFVRVVKAKEQ*VVAG*TMYYLTLEA

KDGGKKKLYEAKVWVK*PWE*NFKELQEFKPVGDA AAAHHHHHH

One or more of the following modifications can/have be made:
- An additional methionine residue (in bold) has been added at the N-terminus to facilitate translation.
- An N-terminal loop can be added to the N-terminus of the Adhiron, and this addition can be typically from 3 up to about 20 amino acids.
- LOOP1 is located at amino acid residues 36-39 (numbered to exclude the N-terminal met) (shown in bold and italics), and suitably these 4 amino acids can be replaced by an insert of typically from 4 up to about 20 amino acids. A loop length of from 5 to 13 amino acids is preferred, and it is believed that a loop length of 9 amino acids is optimal.
- LOOP2 is located at amino acid residues 65-67 (numbered to exclude the N-terminal met) (shown in bold and italics), and suitably these 3 amino acids can be replaced by an insert of typically from 3 up to about 20 amino acids. A loop length of from 5 to 13 amino acids is preferred, and it is believed that a loop length of 9 amino acids is optimal.

A C-terminal linker and His-tag is present. The length and composition of the linker can be varied, and the tag could of course be adapted to any suitable purification system.

Thus, taking Adhiron 92 as an example, a particularly suitable scaffold protein for use in a display system may take the form:

```
N-TERM PEPTIDE                                        LOOP 1
MXXXXXXVRAVPGNENSLEIEELARFAVDEHNKKENALLEFVRVVKAKEQXXXXXXXXXXTM

LOOP2                           linker and tag
YYLTLEAKDGGKKKLYEAKVWVKXXXXXXXXXXNFKELQEFKPVGDA AAAHHHHHH
``` where X is any amino acid. (SEQ ID NO 79)

In general LOOP1 and LOOP2 are believed to be of primary importance in target binding, as supported by the crystal structures (FIG. 17). In certain embodiments of the invention only one of LOOP1 and LOOP2 can be replaced with a peptide sequence, but in general it is preferred that both are replaced. Whilst the N-TERM is not envisaged as being quite as important as LOOPs 1 and 2, in many circumstances inserting a suitable peptide at the N-TERM may result in improved binding affinity and specificity.

FIGS. 20 to 24 show sequence alignments of the LOOP1 and LOOP2 regions of several Adhirons which bind to LOX1, HGH, yeast SUMO, PBP2 and a peptide respectively.

Additionally, FIGS. 27 and 28 show LOOP1 and LOOP2 regions of several Adhirons which bind to Grb2 and STAT3.

It should be noted that peptides can optionally be inserted into the loop regions without removal of the existing amino acids, but this is typically less preferred.

Additional Examples of the Wide Utilities of Adhirons

Immunofluorescence:

Example—Reagents to Detect Viral Proteins

Despite repeated attempts over many years it has not proven possible to raise an antibody that identifies the Human Papilloma Virus E5 protein. (Quantitative measurement of human papillomavirus type 16 E5 oncoprotein levels in epithelial cell lines by mass spectrometry. Sahab et al., J Virol. 2012 September; 86(17):9465-73; Wetherill, L F, Ross, R and Macdonald, A (2012). HPV E5: An enigmatic oncoprotein. Small DNA Tumour Viruses. Ed. K. Gaston. Caister Academic Press. pg 55-70)

Figure 12:
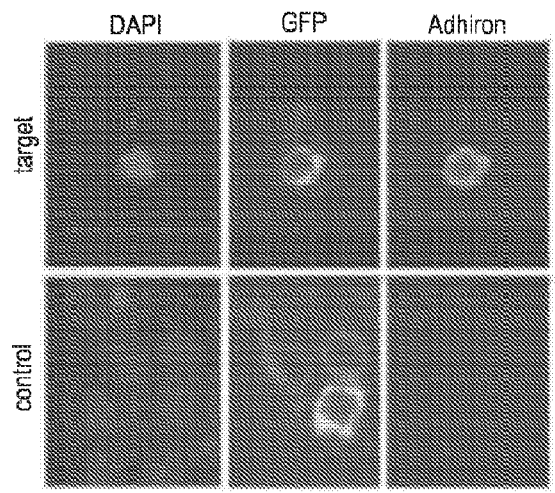

The utility of the Adhiron system is thus demonstrated by the example that Adhirons were raised against HPV16 E5 viral protein using as a target a peptide with identity to a region of the E5 protein. The E5 Adhiron was biotinylated and used in immunofluorescence to detect E5 protein in overexpressed cells. The Adhiron does not cross react with other HPV serotypes. In addition the E5 Adhirons have been conjugated to Quantum Dots and used to detect E5 protein in human samples. Conjugation to Quantum Dots increased the sensitivity of the reagents. See FIG. 12. HPV16 E5 GFP (target) and HPV16 E5 GFP without epitope for Adhiron (control) were expressed in mammalian cells. Adhiron E5 was conjugated to quantum dots and used to detect E5 protein in the mammalian cells. Cells were stained with DAPI (DNA stain), GFP, and E5 (with the Adhiron-Quantum dots). The Adhiron only binds to the target showing specificity to the E5 protein.

Inhibiting and Modifying Protein—Protein Interactions:

Example 1. Reagents that Inhibit Binding to SUMO

Figure 13:
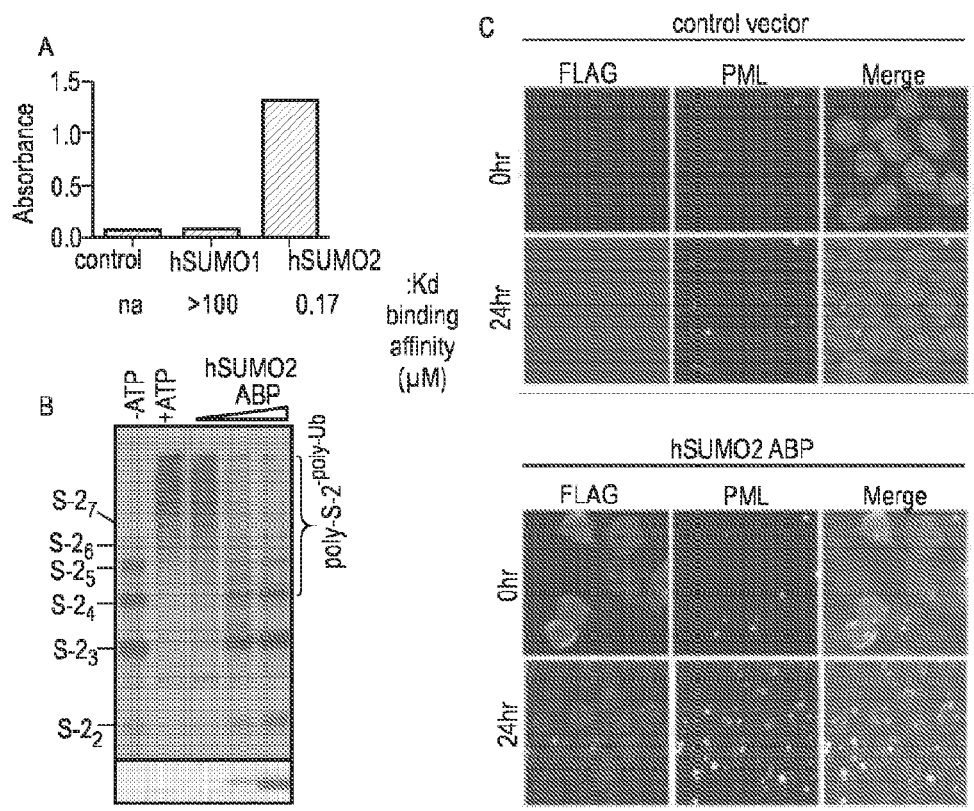

There have been no antibodies raised that are able to specifically and differentially bind to human SUMO 2 (hSUMO2). Adhirons were raised against hSUMO2 and multiple Adhirons that specifically bind to SUMO2 rather than human SUMO1 were identified. FIG. 13 demonstrates that the hSUMO2 Adhirons have a functional effect on a protein-protein interaction by binding to hSUMO2 and preventing RNF4, a polySUMO specific E3 ubiquitin ligase from binding with hSUMO2. The hSUMO2 Adhiron has this effect without affecting ubiquitination of other proteins. In the presence of ATP hSUMO2 normally binds to RNF4 causing ubiquitination of the target proteins (black smear at the top of the gel in lane 2). In the presence of increasing concentrations of the Adhirons (lanes 3 to 9) the level of ubiquitination decreases.

Example 2. Reagents that Alter Fibrin Clot and Lysis

Figure 14:
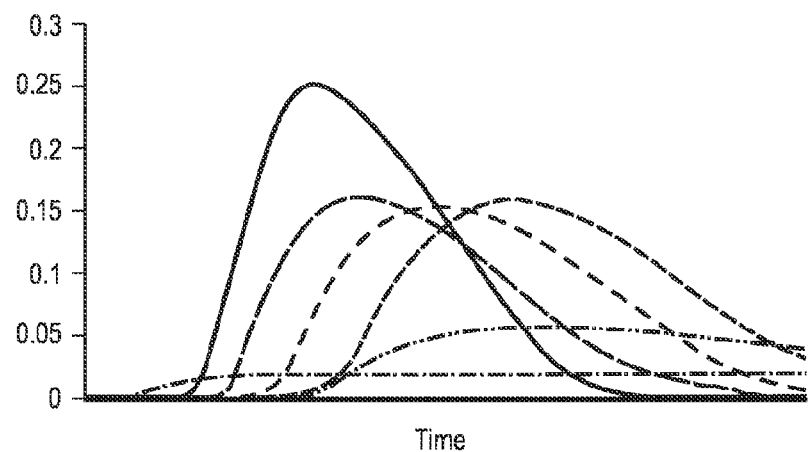
Figure 15:
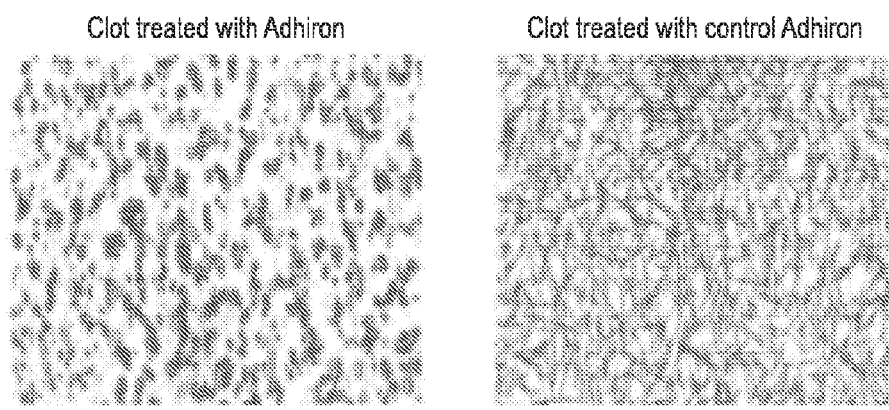
FIG. 15 shows a confocal image of FITC labelled fibrinogen after clot formation with a fibrinogen binding Adhiron and a control Adhiron that does not bind fibrinogen. This demonstrates the ability of the Adhiron to modify the normal clot response.

Fibrinogen was screened to identify Adhirons that could alter clot formation and lysis. Numerous Adhirons have been identified that alter this process in plasma samples. The graph shown in FIG. 14 represents the clot formation and lysis turbidity assay. The black line represents the normal time course of clot formation and lysis. The grey lines represent the effects of five different Adhirons on this process. Control non-fibrinogen binding Adhirons have no effect on this assay. The effects of the Adhirons include, reduced clot formation, increased lysis time, and increased clotting time. This demonstrates an ability of the Adhirons to modulate protein function by inhibiting protein-protein interactions. FIG. 15 shows a confocal image of FITC fluorescently labelled fibrinogen after clot formation in the presence of a fibrinogen binding Adhiron and a control Adhiron.

Figure 16:
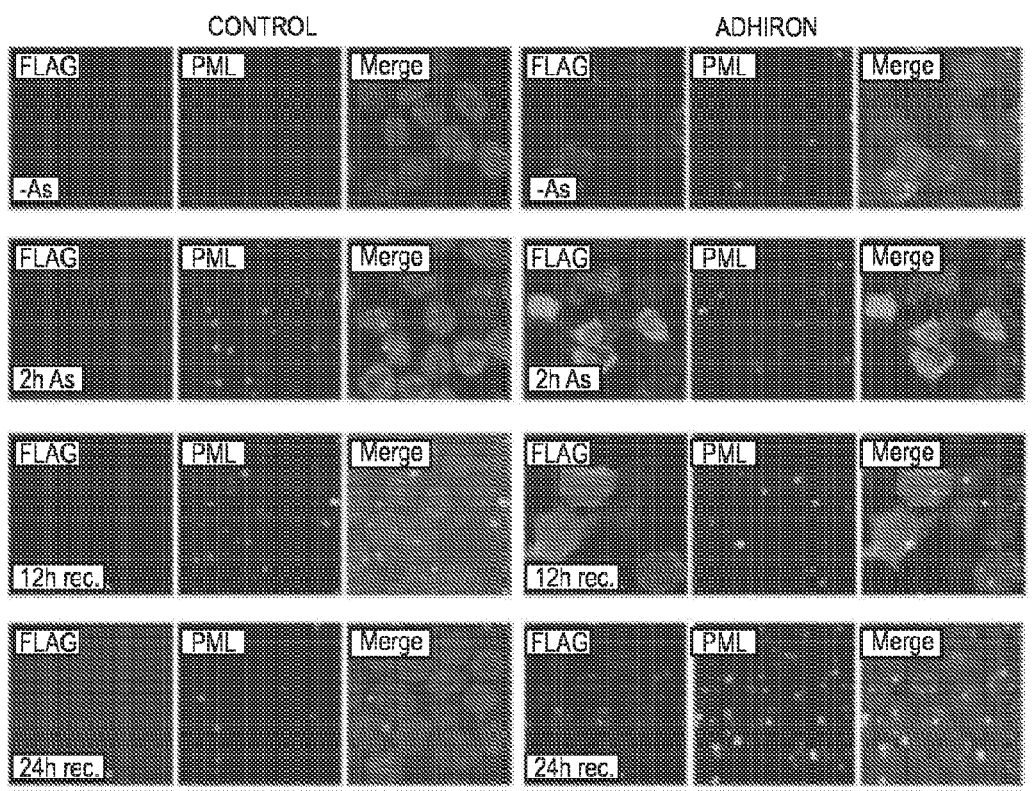
FIG. 16 shows fluoroscopy images that demonstrate the expression of functional Adhirons in mammalian cells. It can be seen that the human SUMO2 binding Adhiron alters the degradation of the nuclear phosphoprotein PML leading to an increase in these PML nuclear bodies.

Expression of Adhirons in Mammalian Cells:

Adhirons were raised against human SUMO2 as described in Example 1 and expressed in mammalian HEK293 cells using the pcDNA3.1 mammalian expression vector. The Adhirons were fused with a FLAG tag and a nuclear localisation signal. Control cells (no Adhiron expressed) and cells expressing a human SUMO2 specific Adhiron were treated with arsenic (As) for 2 hrs then washed and allowed to recover for 12 and 24 hr. Arsenic causes an increase in promyelocytic leukaemia (PML) protein bodies but SUMO regulates the degradation of these bodies. Cells were stained using an anti-FLAG antibody to identify the Adhiron, and for PML (organiser of nuclear bodies). The human SUMO2 Adhiron alters the degradation of PML leading to an increase in these bodies. This demonstrates ability to express functional Adhirons in mammalian cells. The results are shown in FIG. 16.

Co-Crystallisation and Other Structural Biology Methods to Identify Druggable Sites on Proteins:

FIG. 17 shows the co-crystal structure of FcgRIIIa (grey) and bound Adhiron (white). Adhirons were identified that bind to FcgRIIIa then used in a range of assays to show that the inhibit IgG binding, including cell- and SPR-based assays. The Adhirons were then co-crystallised and the structure solved (diagram above). This identified druggable sites, including an allosteric site, on FcgRIIIa. The Adhiron is also suitable for NMR studies and, as an example, FIG. 18 shows 1H-15N HSQC spectra of an anti-yeast SUMO Adhiron and the Adhiron-yeast SUMO complex. The ability to rapidly collect structural data on Adhirons will have many applications including identifying potential drug binding sites.

Incorporation into Electronic Devices for Developing Point of Care Devices:

Site directed mutagenesis of the coding sequence of the human SUMO2 Adhiron (described in Example 1) allowed the introduction of a cysteine at the C-terminal end of the oligohistidine tag. This allowed directional immobilisation of the Adhiron to an electronic device surface such that the molecular recognition loops are accessible to analyte. Upon binding of the target protein to Adhiron on the device a change in impedance can be measured. The change is concentration dependent (as shown in FIG. 19) demonstrating the effective presentation of the Adhiron and the ability of Adhirons to be productively incorporated into electronic devices as a platform for biosensor applications.

This protocol was repeated for another Adhiron, in this case a human fibrinogen Adhiron. The results of this work are shown in FIG. 26. Once again a concentration dependent change was observed, and this was demonstrated over a range from attomolar to micromolar concentrations.

Adhirons have been Identified that Bind to a Range of Targets:

The Adhiron library has been used to screen against a wide range of target molecules by using display methodology described in this document. Table 5 lists examples of targets against which Adhirons have been raised; these include proteins and small molecules. The Adhirons raised against these targets display high affinity and specificity. This demonstrates that that Adhirons provides a versatile scaffold molecule and that the libraries built using this scaffold are effective in identifying artificial binding proteins capable of binding to a broad range of target molecules. Examples of some of the sequences that have been isolated from screens against some of the targets are shown in FIGS. 20-24. We have recently also screened against magnetic particles produced by magnetotropic bacteria and have identified Adhirons that bind to epitopes on these multicomponent bioinorganic complexes.

TABLE 5

Targets against which Adhirons have been successfully raised.

| | |
|---|---|
| FcyRIIIa - protein | Interleukin 8 - protein |
| P7 - peptide | Human serum albumin - protein |
| E5 - peptide | C-reactive protein - protein |
| 3D - protein | Beta 2-microglobulin - protein |
| HSV-1 gB - protein | Serum amyloid P - protein |
| HSV-1gD - protein | Vascular endothelial growth factor receptor 2 - protein |
| HSV-2 gD- protein | Oxidized low-density lipoprotein receptor 1 - protein |
| M2 - protein | Allograft inflammatory factor 1 - protein |
| HE4 - protein | CD30 - protein |
| S100 calcium binding protein B - protein | CD31 - protein |
| Yeast SUMO - protein | Beta secretase1 - protein |
| Human SUMO1 - protein | Proprotein convertase subtilisin/kexin type 9 - protein |
| Human SUMO2 - protein | Myosin e1 - protein |
| GST - protein | Enhance green fluorescent protein - protein |
| Growth Hormone - protein | Fyn - protein |
| Fibroblast growth factor 1 - protein | Lck - protein |
| Fibroblast growth factor receptor 1 - protein | ZAP70 - protein |
| Fibroblast growth factor receptor 3 - protein | TUBA8 - peptide |
| Phospho Fibroblast growth factor receptor 3 | MRP1 - peptide |
| Epidermal growth factor receptor 1 - protein | penicillin-binding protein 2a - protein |
| HER2 - protein | Dog IgE - protein |
| Epiregulin - protein | Horse IgG - protein |
| Amphiregulin - protein | Dog IgG - protein |
| Fibrinogen - protein | Dog CRP - protein |
| Complement C3 - protein | 3 small molecules |
| Myoglobin - protein | Posaconazole - small molecule |
| CK19 - protein | GP-73 - protein |
| HE4 - protein | Thioredoxin - protein |
| CD27 - protein | Signal transducer and activator of transcription 1 - protein |
| Signal transducer and activator of transcription 3 - protein | Signal transducer and activator of transcription 4 - protein |
| Signal transducer and activator of transcription 5 - protein | Phosphoinositide 3-kinase p85 alpha - protein |
| Phosphoinositide 3-kinase p85 beta - protein | Phosphoinositide 3-kinase p55 - protein |
| myeloid leukemia cell differentiation protein - protein | B-cell lymphoma-extra large - protein |
| Nucleoside transporter protein C - membrane protein | Factor XIII - protein |
| Breakpoint cluster region protein - protein | Casein kinase II A1 - protein |

TABLE 5-continued

Targets against which Adhirons have been successfully raised.

| | |
|---|---|
| Casein kinase II A2 - protein | Protein kinase C zeta - protein |
| Protein kinase cGMP dependent type II - protein | vaccinia related kinase 1 - protein |
| Hydrophobin protein 1 - protein | FusB - protein |
| Interleukin 17A - protein | Interleukin 6 - protein |
| Osteocalcin - protein | Osteopontin - protein |
| Parathyroid hormone - protein | Bacterial spores - protein |
| matrix metalloproteinase-3 - protein | Aminotransferase - protein |
| Cytokeratin 8 - protein | S100 - A3 - protein |
| S100 A6 - protein | Transacetylase - protein |
| serine protease inhibitors A1 - protein | serine protease inhibitors A3 - protein |
| GAPDH - protein | p53 - protein |
| Resistin - protein | Lipocalin 2 - protein |
| Procalcitonin - protein | |

REFERENCES

Astwood, J. D., J. N. Leach, et al. (1996). "Stability of food allergens to digestion in vitro." *Nature Biotechnology* 14(10): 1269-1273.

Atkinson, H. J., K. A. Johnston, et al. (2004). "Prima facie evidence that a phytocystatin for transgenic plant resistance to nematodes is not a toxic risk in the human diet." *Journal of Nutrition* 134(2): 431-434.

Bendtsen, J. D., H. Nielsen, et al. (2004). "Improved prediction of signal peptides: SignalP 3.0." *Journal of Molecular Biology* 340(4): 783-795.

Binz, H. K., M. T. Stumpp, et al. (2003). "Designing Repeat Proteins: Well-expressed, Soluble and Stable Proteins from Combinatorial Libraries of Consensus Ankyrin Repeat Proteins." *Journal of Molecular Biology* 332(2): 489-503.

Bode, W., R. Engh, et al. (1988). "The 2.0 a X-Ray Crystal-Structure of Chicken Egg-White Cystatin and Its Possible Mode of Interaction With Cysteine Proteinases." *Embo Journal* 7(8): 2593-2599.

Carter, P. J. (2011). "Introduction to current and future protein therapeutics: A protein engineering perspective." *Experimental Cell Research* 317(9): 1261-1269.

Dai, M. H., H. E. Fisher, et al. (2007). "The creation of a novel fluorescent protein by guided consensus engineering." *Protein Engineering Design & Selection* 20(2): 69-79.

Deboer, H. A., L. J. Comstock, et al. (1983). "THE TAC PROMOTER—A FUNCTIONAL HYBRID DERIVED FROM THE TRP AND LAC PROMOTERS." *Proceedings of the National Academy of Sciences of the United States of America-Biological Sciences* 80(1): 21-25.

Filippova, I. Y., E. N. Lysogorskaya, et al. (1984). "L-Pyroglutamyl-L-Phenylalanyl-L-Leucine-Para-Nitroanilide—a Chromogenic Substrate for Thiol Proteinase Assay." *Analytical Biochemistry* 143(2): 293-297.

FitzGerald, K. (2000). "In vitro display technologies—new tools for drug discovery." *Drug Discovery Today* 5(6): 253-258.

Forrer, P., H. K. Binz, et al. (2004). "Consensus design of repeat proteins." *ChemBioChem* 5: 183-189.

Forrer, P., H. K. Binz, et al. (2004). "Consensus Design of Repeat Proteins." *ChemBioChem* 5(2): 183-189.

Gebauer, M. and A. Skerra (2009). "Engineered protein scaffolds as next-generation antibody therapeutics." *Current Opinion in Chemical Biology* 13(3): 245-255.

Grebien, F., O. Hantschel, et al. (2011). "Targeting the SH2-Kinase Interface in Bcr-Abl Inhibits Leukemogenesis." *Cell* 147(2): 306-319.

Ho, M. and I. Pastan (2009). Mammalian Cell Display for Antibody Engineering. *Methods in Molecular Biology*. A. S. Dimitrov. 525: 337-352.

Hoffmann, T., L. K. Stadler, et al. (2010). "Structure-function studies of an engineered scaffold protein derived from stefin A. I: Development of the SQM variant." *Protein Eng Des Sel* 23(5): 403-413.

Hoogenboom, H. R., A. D. Griffiths, et al. (1991). "Multi-subunit Proteins on the Surface of Filamentous Phage—Methodologies for Displaying Antibody (Fab) Heavy and Light-Chains." *Nucleic Acids Research* 19(15): 4133-4137.

Horton, R., Z. Cai, et al. (1990). "Gene splicing by overlap extension: tailor-made genes using the polymerase chain reaction." *Biotechniques* 8: 528-535.

Hutchison, C. A., S. Phillips, et al. (1978). "Mutagenesis at a specific position in a DNA sequence." *Journal of Biological Chemistry* 253(18): 6551-6560.

Jacobs, S. A., M. D. Diem, et al. (2012). "Design of novel FN3 domains with high stability by a consensus sequence approach." *Protein Engineering Design & Selection* 25(3): 107-117.

Jacobs, S. A., M. D. Diem, et al. (2012). "Design of novel FN3 domains with high stability by a consensus sequence approach." *Protein Enq Des Sel* 25(3): 107-117.

Jaeckel, C., J. D. Bloom, et al. (2010). "Consensus Protein Design without Phylogenetic Bias." *Journal of Molecular Biology* 399(4): 541-546.

Karatan, E., M. Merguerian, et al. (2004). "Molecular recognition properties of FN3 monobodies that bind the Src SH3 domain." *Chemistry & Biology* 11(6): 835-844.

Kayushin, A., M. Korosteleva, et al. (1996). "A convenient approach to the synthesis of trinucleotide phosphoramidites-synthons for the generation of oligonucleotide/peptide libraries." *Nucleic Acids Res* 24: 3748-3755.

Knappik, A., L. Ge, et al. (2000). "Fully synthetic human combinatorial antibody libraries (HuCAL) based on modular consensus frameworks and CDRs randomized with trinucleotides." *Journal of Molecular Biology* 296 (1): 57-86.

Kohler, G. and C. Milstein (1975). "Continuous cultures of fused cells secreting antibody of predefined specificity." *Nature* 256(5517): 495-497.

Koide, A., C. W. Bailey, et al. (1998). "The fibronectin type III domain as a scaffold for novel binding proteins." *Journal of Molecular Biology* 284(4): 1141-1151.

Koide, A., C. W. Bailey, et al. (1998). "The fibronectin type III domain as a scaffold for novel binding proteins." *Journal of Molecular Biology* 284(4): 1141-1151.

Koide, A., R. N. Gilbreth, et al. (2007). "High-affinity single-domain binding proteins with a binary-code interface." *Proceedings of the National Academy of Sciences of the United States of America* 104(16): 6632-6637.

Koiwa, H., M. P. D'Urzo, et al. (2001). "Phage display selection of hairpin loop soyacystatin variants that mediate high affinity inhibition of a cysteine proteinase." *Plant Journal* 27(5): 383-391.

Komor, R. S., P. A. Romero, et al. (2012). "Highly thermostable fungal cellobiohydrolase I (Cel7A) engineered using predictive methods." *Protein engineering, design & selection: PEDS* 25(12): 827-833.

Komor, R. S., P. A. Romero, et al. (2012). "Highly thermostable fungal cellobiohydrolase I (Cel7A) engineered using predictive methods." *Protein Engineering Design and Selection* 25(12): 827-833.

Kondo, H., K. Abe, et al. (1991). "Gene Organization of Oryzacystatin-li, a New Cystatin Superfamily Member of Plant-Origin, Is Closely Related to That of Oryzacystatin-I But Different From Those of Animal Cystatins." *Febs Letters* 278(1): 87-90.

Kordis, D. and V. Turk (2009). "Phylogenomic analysis of the cystatin superfamily in eukaryotes and prokaryotes." *Bmc Evolutionary Biology* 9.

Krumpe, L., K. Schumacher, et al. (2007). "Trinucleotide cassettes increase diversity of T7 phage-displayed peptide library." *BMC Biotechnology* 7(1): 65.

Lee, S.-C., K. Park, et al. (2012). "Design of a binding scaffold based on variable lymphocyte receptors of jawless vertebrates by module engineering." *Proceedings of the National Academy of Sciences* 109(9): 3299-3304.

Lehmann, M., C. Loch, et al. (2002). "The consensus concept for thermostability engineering of proteins: further proof of concept." *Protein Engineering* 15(5): 403-411.

Lehmann, M., R. Lopez-Ulibarri, et al. (2000). "Exchanging the active site between phytases for altering the functional properties of the enzyme." 9(10): 1866-1872.

Lehmann, M. and M. Wyss (2001). "Engineering proteins for thermostability: the use of sequence alignments versus rational design and directed evolution." *Current Opinion in Biotechnology* 12(4): 371-375.

Lilley, C. J., P. E. Urwin, et al. (2004). "Preferential expression of a plant cystatin at nematode feeding sites confers resistance to Meloidogyne incognita and Globodera pallida." *Plant Biotechnology Journal* 2(1): 3-12.

Lofblom, J. (2011). "Bacterial display in combinatorial protein engineering." *Biotechnology Journal* 6(9): 1115-1129.

Lord, P. W., J. N. Selley, et al. (2002). "CINEMA-MX: a modular multiple alignment editor." *Bioinformatics* 18(10): 1402-1403.

Main, E. R. G., S. E. Jackson, et al. (2003). "The folding and design of repeat proteins: reaching a consensus." *Current Opinion in Structural Biology* 13(4): 482-489.

Main, E. R. G., A. R. Lowe, et al. (2005). "A recurring theme in protein engineering: the design, stability and folding of repeat proteins." *Current Opinion in Structural Biology* 15(4): 464-471.

Main, E. R. G., Y. Xiong, et al. (2003). "Design of stable alpha-helical arrays from an idealized TPR motif." *Structure* 11(5): 497-508.

Makela, A. R. and C. Oker-Blom (2008). "The baculovirus display technology—An evolving instrument for molecular screening and drug delivery." *Combinatorial Chemistry & High Throughput Screening* 11(2): 86-98.

Margis, R., E. M. Reis, et al. (1998). "Structural and phylogenetic relationships among plant and animal cystatins." *Archives of Biochemistry and Biophysics* 359(1): 24-30.

McPherson, M. J., P. E. Urwin, et al. (1997). Engineering plant nematode resistance by an anti-feedant approach. *Cellular and Molecular Basis for Plant-Nematode Interactions*. C. Fenoll, S. Ohl and F. Grundler. The Netherlands, Kluwer: 237-249.

Melo, F. R., M. O. Mello, et al. (2003). "Use of phage display to select novel cystatins specific for *Acanthoscelides obtectus* cysteine proteinases." *Biochimica Et Biophysica Acta-Proteins and Proteomics* 1651(1-2): 146-152.

Mosavi, L. K., T. J. Cammett, et al. (2004). "The ankyrin repeat as molecular architecture for protein recognition." *Protein Science* 13(6): 1435-1448.

Mosavi, L. K., D. L. Minor, et al. (2002). "Consensus-derived structural determinants of the ankyrin repeat motif." *Proceedings of the National Academy of Sciences* 99(25): 16029-16034.

Mullis, K., F. Faloona, et al. (1986). "Specific enzymatic amplification of DNA in vitro: the polymerase chain reaction." *Cold Spring Harb Symp Quant Biol* 51 Pt 1: 263-273.

Nagata, K., N. Kudo, et al. (2000). "Three-dimensional solution structure of oryzacystatin-I, a cysteine proteinase inhibitor of the rice, *Oryza sativa L. japonica.*" *Biochemistry* 39(48): 14753-14760.

Nixon A E, W. C. (2006). "Engineered protein inhibitors of proteases." *Curr Opin Drug Discov Devel* 9(2): 261-268.

Nord, K., J. Nilsson, et al. (1995). "A combinatorial library of an α-helical bacterial receptor domain." *Protein Engineering* 8(6): 601-608.

Odegrip, R., D. Coomber, et al. (2004). "CIS display: In vitro selection of peptides from libraries of protein-DNA complexes." *Proceedings of the National Academy of Sciences of the United States of America* 101(9): 2806-2810.

Parizek, P., L. Kummer, et al. (2012). "Designed Ankyrin Repeat Proteins (DARPins) as Novel Isoform-Specific Intracellular Inhibitors of c-Jun N-Terminal Kinases." *ACS Chemical Biology* 7(8): 1356-1366.

Parmeggiani, F., R. Pellarin, et al. (2008). "Designed armadillo repeat proteins as general peptide-binding scaffolds: Consensus design and computational optimization of the hydrophobic core." *Journal of Molecular Biology* 376(5): 1282-1304.

Parry-Smith, D. J., A. W. R. Payne, et al. (1998). "CINEMA—a novel colour interactive editor for multiple alignments (Reprinted from Gene, vol 221, pg GC57-GC63, 1998)." *Gene* 221(1): GC57-GC63.

Polizzi, K. M., J. F. Chaparro-Riggers, et al. (2006). "Structure-guided consensus approach to create a more thermostable penicillin G acylase." *Biotechnology Journal* 1(5): 531-536.

Reichert, J. M. (2010). "Antibodies to watch in 2010." *MAbs.* 2(1): 84-100.

Saiki R K, S. S., Faloona F, Mullis K B, Horn G T, Erlich H A, Arnheim N. (1985). "Enzymatic amplification of beta-globin genomic sequences and restriction site analysis for diagnosis of sickle cell anemia." *Science* 230 (4732): 1350-1354.

Schlehuber, S. and A. Skerra (2005). "Anticalins as an alternative to antibody technology." *Expert Opinion on Biological Therapy* 5(11): 1453-1462.

Skerra, A. (2007). "Alternative non-antibody scaffolds for molecular recognition." *Current Opinion in Biotechnology* 18: 295-304.

Smith, G. (1985). "Filamentous fusion phage: novel expression vectors that display cloned antigens on the virion surface." *Science* 228(4705): 1315-1317.

Song, I., M. Taylor, et al. (1995). "Inhibition of Cysteine Proteinases By *Carica-Papaya* Cystatin Produced in *Escherichia-Coli.*" *Gene* 162(2): 221-224.

Song, J., L. K. Durrin, et al. (2004). "Identification of a SUMO-binding motif that recognizes SUMO-modified proteins." *Proc Natl Acad Sci USA* 101(40): 14373-14378.

Song, J., Z. Zhang, et al. (2005). "Small ubiquitin-like modifier (SUMO) recognition of a SUMO binding motif: a reversal of the bound orientation." *J Biol Chem* 280(48): 40122-40129.

Stadler, L. K., T. Hoffmann, et al. (2011). "Structure-function studies of an engineered scaffold protein derived from Stefin A. II: Development and applications of the SQT variant." *Protein Enq Des Sel* 24(9): 751-763.

Steipe, B. (2004). "Consensus-based engineering of protein stability: From intrabodies to thermostable enzymes." *Protein Engineering* 388: 176-186.

Steipe, B., B. Schiller, et al. (1994). "Sequence Statistics Reliably Predict Stabilizing Mutations in a Protein Domain." *Journal of Molecular Biology* 240(3): 188-192.

Steipe, B., B. Schiller, et al. (1994). "Sequence Statistics Reliably Predict Stabilizing Mutations in a Protein Domain." *Journal of Molecular Biology* 240(3): 188-192.

Stubbs, M. T., B. Laber, et al. (1990). "The Refined 2.4a X-Ray Crystal-Structure of Recombinant Human Stefin-B in Complex With the Cysteine Proteinase Papain—a Novel Type of Proteinase-Inhibitor Interaction." *Embo Journal* 9(6): 1939-1947.

Studier, F. W. and B. A. Moffatt (1986). "Use of bacteriophage T7 RNA polymerase to direct selective high-level expression of cloned genes." *J Mol Biol* 189(1): 113-130.

Theurillat, J.-P., B. Dreier, et al. (2010). "Designed ankyrin repeat proteins: a novel tool for testing epidermal growth factor receptor 2 expression in breast cancer." *Mod Pathol* 23(9): 1289-1297.

Traxlmayr, M. W. and C. Obinger (2012). "Directed evolution of proteins for increased stability and expression using yeast display." *Archives of Biochemistry and Biophysics* 526(2): 174-180.

Urwin, P. E., H. J. Atkinson, et al. (1995). "Engineered Oryzacystatin-I Expressed in Transgenic Hairy Roots Confers Resistance to *Globodera-Pallida.*" *Plant Journal* 8(1): 121-131.

Urwin, P. E., J. Green, et al. (2003). "Expression of a plant cystatin confers partial resistance to *Globodera*, full resistance is achieved by pyramiding a cystatin with natural resistance." *Molecular Breeding* 12(3): 263-269.

Urwin, P. E., A. Levesley, et al. (2000). "Transgenic resistance to the nematode *Rotylenchulus reniformis* conferred by *Arabidopsis thaliana* plants expressing proteinase inhibitors." *Molecular Breeding* 6(3): 257-264.

Urwin, P. E., C. J. Lilley, et al. (1997). "Resistance to both cyst and root-knot nematodes conferred by transgenic *Arabidopsis* expressing a modified plant cystatin." *Plant Journal* 12(2): 455-461.

Urwin, P. E., M. J. McPherson, et al. (1998). "Enhanced transgenic plant resistance to nematodes by dual proteinase inhibitor constructs." *Planta* 204(4): 472-479.

Urwin, P. E., K. M. Troth, et al. (2001). "Effective transgenic resistance to *Globodera pallida* in potato field trials." *Molecular Breeding* 8(1): 95-101.

Virnekas, B., L. Ge, et al. (1994). "Trinucleotide phosphoramidites: ideal reagents for the synthesis of mixed oligonucleotides for random mutagenesis." *Nucleic Acids Res* 22: 5600-5607.

Von Behring, E., Kitasato, S., (1890). "Ober das Zustandekommen der Diphterie-Immunitat und der Tetanus-Immunitat bei Thieren." *Deutsche Medizinische Wochenzeitschrift* 16: 1113-1114.

Wojcik, J., O. Hantschel, et al. (2010). "A potent and highly specific FN3 monobody inhibitor of the Abl SH2 domain." *Nat Struct Mol Biol* 17(4): 519-527.

Woodman, R., J. T. H. Yeh, et al. (2005). "Design and validation of a neutral protein scaffold for the presentation of peptide aptamers." *Journal of Molecular Biology* 352(5): 1118-1133.

Wurch, T., A. Pierre, et al. (2012). "Novel protein scaffolds as emerging therapeutic proteins: from discovery to clinical proof-of-concept." *Trends in Biotechnology* 30(11): 575-582.

The invention claimed is:

1. A synthetic scaffold protein comprising an amino acid sequence which is at least 85% identical to NSLEIEELAR-FAVDEHNKKENALLEFVRVVKAKEQVVAGT-MYYLTLEAKDGGKKKLYEAKVWVKPWENF KELQEFKPVGDA (SEQ ID NO:1), wherein the synthetic scaffold protein further comprises at least one heterologous peptide of from 3 to 20 amino acids in length, wherein the heterologous peptide is inserted: (a) adjacent to any of amino acid residues VVAG (SEQ ID NO:82); (b) in replacement of amino acid residues VVAG (SEQ ID NO:82); (c) adjacent to any of amino acid residues PWE; (d) in replacement of amino acid residues PWE; or (e) any combination of (a)-(d) thereof, wherein said amino acid residues VVAG (SEQ ID NO:82) or PWE are present as a contiguous sequence in the amino acid sequence of SEQ ID NO:1, wherein the heterologous peptide is heterologous to the amino acid sequence of SEQ ID NO:1, and wherein the at least one heterologous peptide inserted into the synthetic scaffold protein is disregarded when calculating sequence identity of the synthetic scaffold protein.

2. The synthetic scaffold protein of claim 1, wherein the synthetic scaffold protein further comprises a heterologous peptide inserted at the N-terminus of the protein.

3. The synthetic scaffold protein of claim 1, wherein the synthetic scaffold protein comprises an additional amino acid sequence at the N-terminus.

4. The synthetic scaffold protein of claim 3, wherein the additional amino acid sequence at the N-terminus comprises the sequence MATGVRAVPGNE (SEQ ID NO:80).

5. The synthetic scaffold protein of claim 3, wherein the additional amino acid sequence at the N-terminus comprises a heterologous peptide sequence.

6. The synthetic scaffold protein of claim 1, wherein the synthetic scaffold protein has a melting temperature (Tm) of at least 70° C.

7. The synthetic scaffold protein of claim 1, wherein the synthetic scaffold protein further comprises a linker or tag.

8. The synthetic scaffold protein of claim 1, wherein the synthetic scaffold protein is connected to a substrate or moiety.

9. The synthetic scaffold protein of claim 8, wherein the moiety is a label, carrier, or protein.

10. The synthetic scaffold protein of claim 8, wherein the moiety or substrate is attached to one terminus or both termini of the synthetic scaffold protein.

11. The synthetic scaffold protein of claim 1, wherein the synthetic scaffold protein is a fusion protein.

12. A pharmaceutical preparation comprising the synthetic scaffold protein according to claim 1 and a pharmaceutically acceptable carrier or excipient.

13. A synthetic scaffold protein comprising the amino acid sequence: NSLEIEELARFAVDEHNKKENALLEFVRV- VKAKEQ($X_n$)TMYYLTLEAKDG GKKKLYEAKVWVK ($X_n$)NFKELQEFKPVGDA (SEQ ID NO:4) or an amino acid sequence which is at least 85% identical to the amino acid sequence of SEQ ID NO:4, wherein X is any amino acid and n is the number of amino acids in the sequence, and wherein n is from 3 to 20.

14. The synthetic scaffold protein according to claim 13, wherein the synthetic scaffold protein comprises the amino acid sequence:

```
                                         (SEQ ID NO: 5)
NSLEIEELARFAVDEHNKKENALLEFVRVVKAKEQ(X5-13)TMYYLTLEA

KDGGKKKLYEAKVWVK(X5-13)NEKELQEFKPVGDA.
```

15. The synthetic scaffold protein according to claim 13, wherein the synthetic scaffold protein comprises the amino acid sequence:

```
                                         (SEQ ID NO: 6)
NSLEIEELARFAVDEHNKKENALLEFVRVVKAKEQ(X9)TMYYLTLEA

KDGGKKKLYEAKVWVK(X9)NFKELQEFKPVGDA.
```

16. The synthetic scaffold protein of claim 13, wherein the synthetic scaffold protein has a melting temperature (Tm) of at least 70° C.

17. A pharmaceutical preparation comprising the synthetic scaffold protein of claim 13 and a pharmaceutically acceptable carrier or excipient.

18. A synthetic scaffold protein comprising the amino acid sequence NSLEIEELARFAVDEHNKKENALLEFVRVVKAKEQVVAGTMYYLTLEAKDGGKKKLY EAKVWVKPWENFKELQEFKPVGDA (SEQ ID NO:1) or an amino acid sequence which is at least 85% identical to the amino acid sequence of SEQ ID NO:1.

19. The synthetic scaffold protein of claim 18, wherein the synthetic scaffold protein further comprises at least one heterologous peptide of from 3 to 20 amino acids in length, wherein the heterologous peptide is inserted: (a) adjacent to any of amino acid residues VVAG (SEQ ID NO:82); (b) in replacement of amino acid residues VVAG (SEQ ID NO:82); (c) adjacent to any of amino acid residues PWE; (d) in replacement of amino acid residues PWE; or (e) any combination of (a)-(d) thereof; wherein said amino acid residues VVAG (SEQ ID NO:82) or PWE are present as a contiguous sequence in the amino acid sequence of SEQ ID NO:1, wherein the heterologous peptide is heterologous to the amino acid sequence of SEQ ID NO:1.

20. The synthetic scaffold protein of claim 19, wherein the synthetic scaffold protein has a melting temperature (Tm) of at least 70° C.

21. A pharmaceutical preparation comprising the synthetic scaffold protein of claim 18 and a pharmaceutically acceptable carrier or excipient.

22. A pharmaceutical preparation comprising the synthetic scaffold protein of claim 19 and a pharmaceutically acceptable carrier or excipient.

* * * * *

UNITED STATES PATENT AND TRADEMARK OFFICE
CERTIFICATE OF CORRECTION

PATENT NO. : 9,932,575 B2
APPLICATION NO. : 14/768032
DATED : April 3, 2018
INVENTOR(S) : McPherson et al.

It is certified that error appears in the above-identified patent and that said Letters Patent is hereby corrected as shown below:

In the Specification

Column 5, Line 40: Please correct "WAG" to read -- VVAG --

Column 10, Line 12, SEQ ID NO: 6: Please correct "VVVVK($X_9$)" to read -- VWVK($X_9$) --

Column 18, Line 55: Please correct "QWAG" to read -- QVVAG --

Column 19, Line 5: Please correct "high 13" to read -- high β --

Column 22, Line 45: Please correct "UnNin" to read -- Urwin --

Column 28, Line 1: Please correct "can" to read -- cun --

Column 29, Line 56: Please correct "t%" to read -- t½ --

Column 30, Line 67: Please correct "QWAG" to read -- QVVAG --

Column 31, Line 67: Please correct "WAG" to read -- VVAG --

Column 46, Table 5, Line 1: Please correct "FcyRIIIa" to read -- FcγRIIIa --

Column 52, Line 29, Von Behring cite: Please correct "Ober" to read -- Über --

Column 52, Line 30, Von Behring cite: Please correct "Immunitat" to read -- Immunität --

Column 52, Line 31, Von Behring cite: Please correct "Immunitat" to read -- Immunität --

Signed and Sealed this
Twenty-fourth Day of July, 2018

Andrei Iancu
*Director of the United States Patent and Trademark Office*

CERTIFICATE OF CORRECTION (continued)
U.S. Pat. No. 9,932,575 B2

In the Claims

Column 179, Claim 14, SEQ ID NO: 5, Line 14: Please correct "($X_{5-13}$)NEKE" to read -- ($X_{5-13}$)NFKE --